(12) United States Patent
Yamada et al.

(10) Patent No.: US 11,400,342 B2
(45) Date of Patent: Aug. 2, 2022

(54) MOVING BODY INFORMATION PROVIDING SYSTEM AND PROGRAM

(71) Applicant: ASIA AIR SURVEY CO., LTD., Tokyo (JP)

(72) Inventors: Takayuki Yamada, Tokyo (JP); Yuichi Fujimoto, Tokyo (JP); Toshihiko Koyama, Tokyo (JP); Yukihiro Minami, Tokyo (JP)

(73) Assignee: ASIA AIR SURVEY CO., LTD., Tokyo (JP)

( * ) Notice: Subject to any disclaimer, the term of this patent is extended or adjusted under 35 U.S.C. 154(b) by 694 days.

(21) Appl. No.: 16/338,326

(22) PCT Filed: Sep. 29, 2017

(86) PCT No.: PCT/JP2017/035649
§ 371 (c)(1),
(2) Date: Mar. 29, 2019

(87) PCT Pub. No.: WO2018/062535
PCT Pub. Date: Apr. 5, 2018

(65) Prior Publication Data
US 2020/0023237 A1    Jan. 23, 2020

(30) Foreign Application Priority Data

Sep. 30, 2016 (JP) .............................. JP2016-193864
Aug. 14, 2017 (JP) .............................. JP2017-156477

(51) Int. Cl.
*A63B 24/00* (2006.01)
*A61B 5/11* (2006.01)
(Continued)

(52) U.S. Cl.
CPC ........ *A63B 24/0062* (2013.01); *A61B 5/1112* (2013.01); *A61B 5/681* (2013.01);
(Continued)

(58) Field of Classification Search
CPC ................................................ A63B 24/0062
(Continued)

(56) References Cited

U.S. PATENT DOCUMENTS

2001/0049470 A1    12/2001   Mault et al.
2006/0003777 A1    1/2006    Nonoyama et al.
(Continued)

FOREIGN PATENT DOCUMENTS

CN          1716818 A     1/2006
CN          103170105 A   6/2013
(Continued)

OTHER PUBLICATIONS

English translation of the First Office Action issued for corresponding Chinese Patent Application No. 2017800608589, dated Mar. 9, 2021.
(Continued)

*Primary Examiner* — Kesha Frisby
(74) *Attorney, Agent, or Firm* — Greenblum & Bernstein, P.L.C.

(57) ABSTRACT

A moving body information providing system constituted by a moving body information analysis device and wearable devices 1 mounted to soccer players for detecting the status of the soccer players, wherein the wearable devices are each provided with a storage unit, an internal timer, a position sensor, a moving body information detection sensor having a plurality of types of sensors, an initial-time setting unit, a position data calculation unit, an output control unit, a communication module, and other components, and the moving body information analysis device has a tablet provided with a moving body information transmission/reception unit, an analysis result display processing unit, and other components, and an analysis result providing device of an analysis center provided with a storage unit for fine position data, a position calculation unit, or the like.

19 Claims, 46 Drawing Sheets

(51) Int. Cl.
*A61B 5/00* (2006.01)
*G01C 22/00* (2006.01)
*G01S 19/19* (2010.01)
*G06Q 10/06* (2012.01)
*G06V 40/20* (2022.01)

(52) U.S. Cl.
CPC ............ *G01C 22/006* (2013.01); *G01S 19/19* (2013.01); *G06Q 10/0639* (2013.01); *G06V 40/25* (2022.01); *A63B 2243/0025* (2013.01)

(58) Field of Classification Search
USPC .......................................................... 701/469
See application file for complete search history.

(56) References Cited

U.S. PATENT DOCUMENTS

| | | |
|---|---|---|
| 2008/0046179 A1 | 2/2008 | Mackintosh |
| 2008/0284650 A1 | 11/2008 | MacIntosh |
| 2013/0106603 A1 | 5/2013 | Weast et al. |
| 2013/0166049 A1 | 6/2013 | Werner et al. |
| 2014/0037138 A1 | 2/2014 | Sato et al. |
| 2014/0046588 A1 | 2/2014 | Maezawa et al. |
| 2014/0324300 A1* | 10/2014 | Halder ............... G01S 19/49 701/50 |
| 2015/0204983 A1 | 7/2015 | Georgy |
| 2016/0121163 A1 | 5/2016 | Case, Jr. |

FOREIGN PATENT DOCUMENTS

| | | |
|---|---|---|
| CN | 103578115 A | 2/2014 |
| DE | 20 2016 100 594 U1 | 2/2016 |
| JP | 2004-509652 | 4/2004 |
| JP | 2008-272163 | 11/2008 |
| JP | 2009-297057 | 12/2009 |

OTHER PUBLICATIONS

Official Communication issued in International Bureau of WIPO Patent Application No. PCT/JP2017/035649, dated Dec. 26, 2017.
Supplementary European Search Report in corresponding EPO Application No. EP 17856482.9, dated May 20, 2020.

* cited by examiner

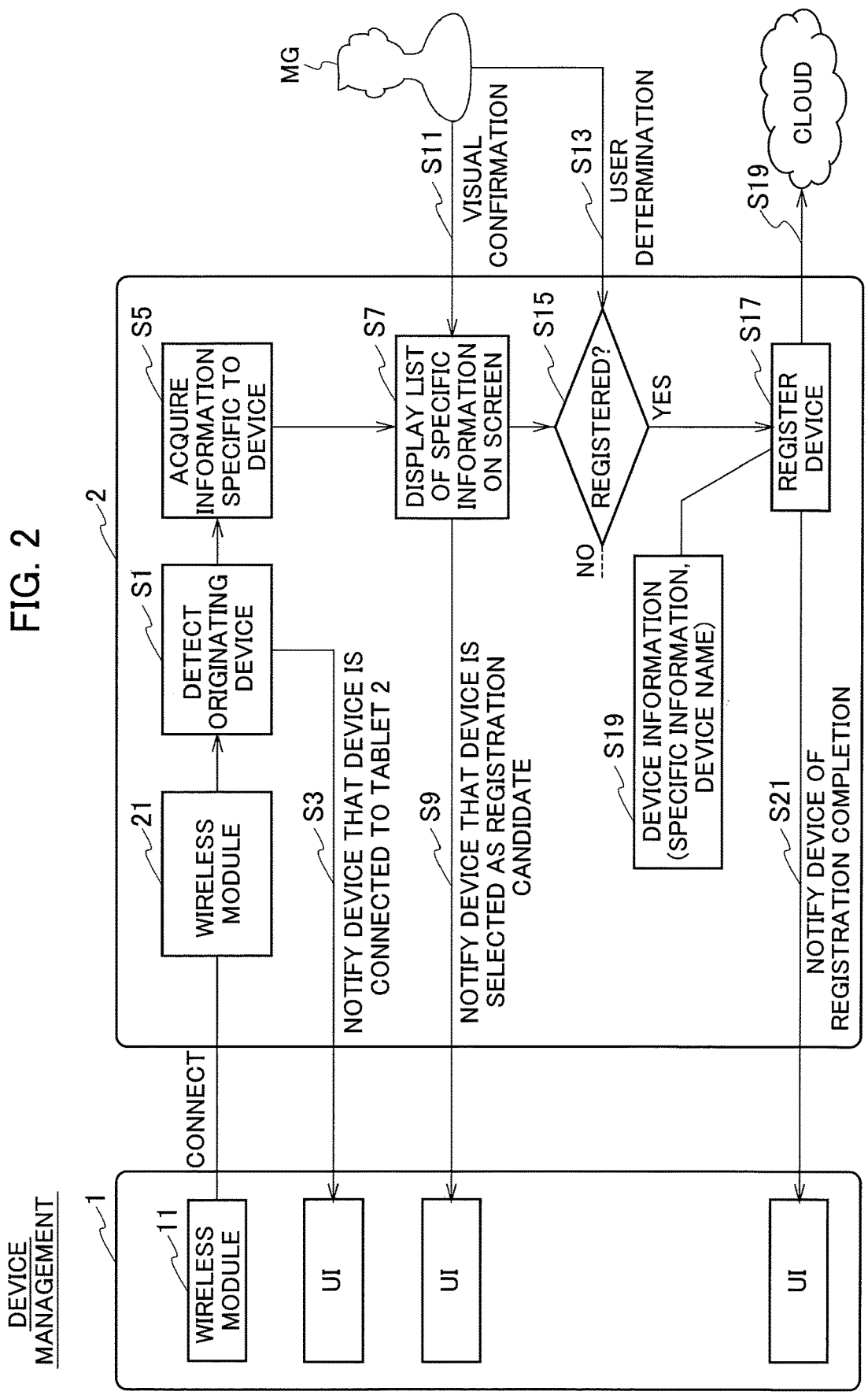

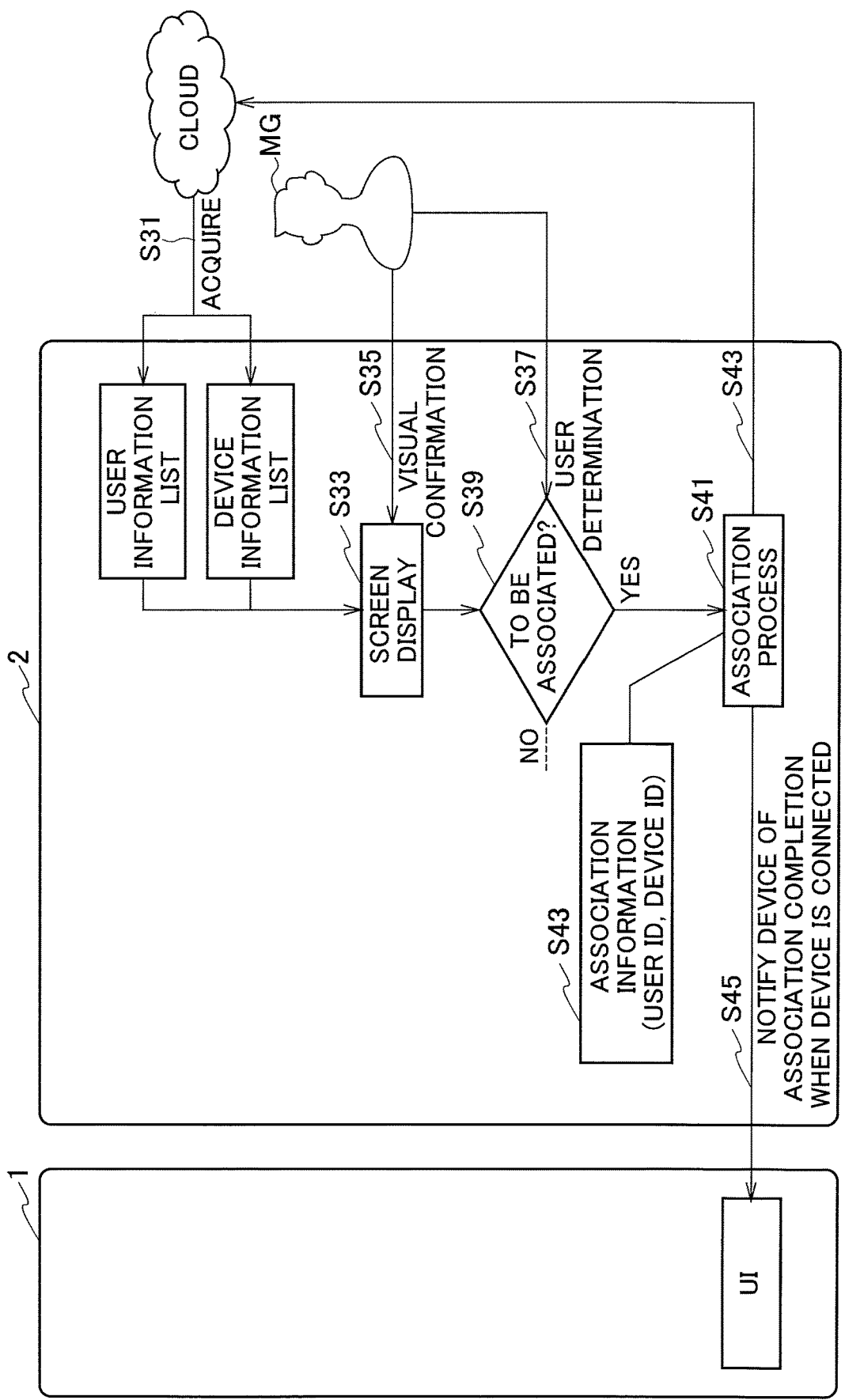

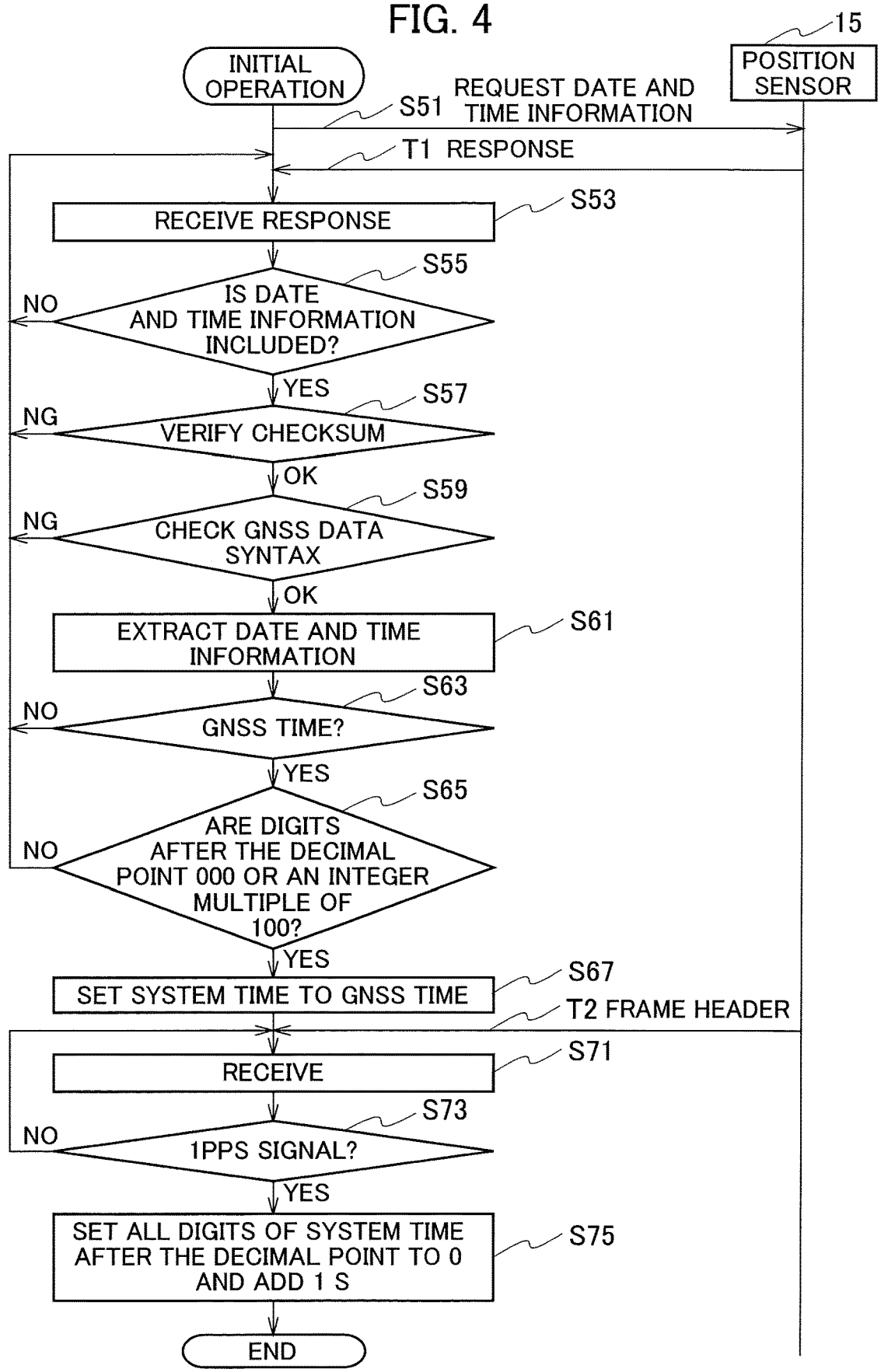

FIG. 8(a)

TIME | LATITUDE AND LONGITUDE

YYYY/MM/DD:HH:MM:01.100, E1,N1
YYYY/MM/DD:HH:MM:01.200, --, --
↓
YYYY/MM/DD:HH:MM:01.100, E1,N1
YYYY/MM/DD:HH:MM:01.200, E1,N1

FIG. 8(b)

YYYY/MM/DD:HH:MM:01.200, --,--
YYYY/MM/DD:HH:MM:01.300, E2,N2
↓
YYYY/MM/DD:HH:MM:01.200, E2,N2
YYYY/MM/DD:HH:MM:01.300, E2,N2

FIG. 8(c)

YYYY/MM/DD:HH:MM:01.100, E1,N1
YYYY/MM/DD:HH:MM:01.200, --,--
YYYY/MM/DD:HH:MM:01.300, E2,N2
↓
YYYY/MM/DD:HH:MM:01.100, E1,N1
YYYY/MM/DD:HH:MM:01.200, (E1+E2)/2, (N1+N2)/2
YYYY/MM/DD:HH:MM:01.300, E2,N2

FIG. 9(a)

|  | SENSOR DATA |
| TIME | (HEART RATE) |

YYYY/MM/DD:HH:MM:01.100, 54
YYYY/MM/DD:HH:MM:01.200, --
↓
YYYY/MM/DD:HH:MM:01.100, 54
YYYY/MM/DD:HH:MM:01.200, 54

FIG. 9(b)

YYYY/MM/DD:HH:MM:01.200, --
YYYY/MM/DD:HH:MM:01.300, 63
↓
YYYY/MM/DD:HH:MM:01.200, 63
YYYY/MM/DD:HH:MM:01.300, 63

FIG. 9(c)

YYYY/MM/DD:HH:MM:01.100, 54
YYYY/MM/DD:HH:MM:01.200, --
YYYY/MM/DD:HH:MM:01.300, 63
↓
YYYY/MM/DD:HH:MM:01.100, 54
YYYY/MM/DD:HH:MM:01.200, 58.5
YYYY/MM/DD:HH:MM:01.300, 63

FIG. 14

| DISPLAY CONTROL DATA PKJi | | | TIME RANGE Wti | | | | |
|---|---|---|---|---|---|---|---|
| WEARABLE DEVICE ID | DISPLAY APPARATUS (TABLET ID) | NAME | FACE PHOTO | SDi (HEART RATE) | SYSTEM TIME STi | DETECTION POSITION Pi | CAMERA NUMBER | WINDOW NUMBER |
| | | | | SDi (BODY TEMPERATURE) | ... | ... | ... | ... |
| | | | | SDi (9-AXIS) | | | | |
| | | | | ... | | | | |

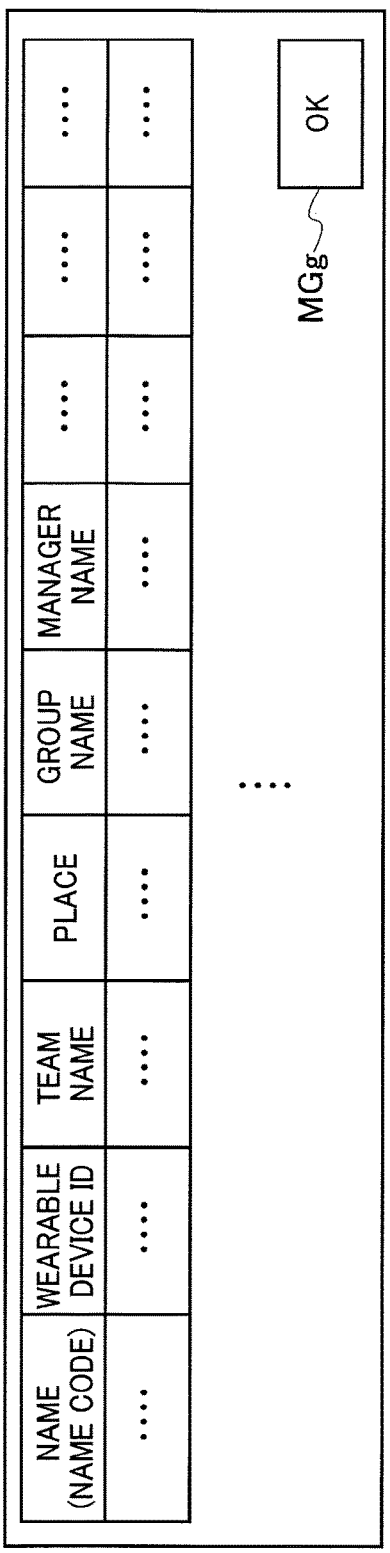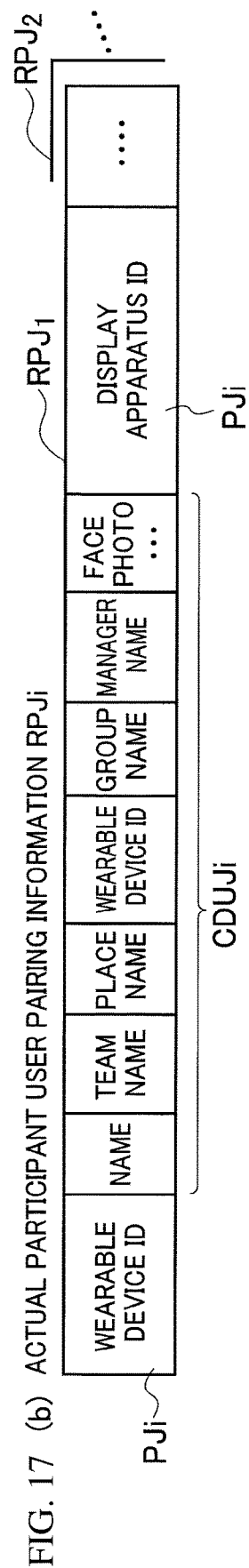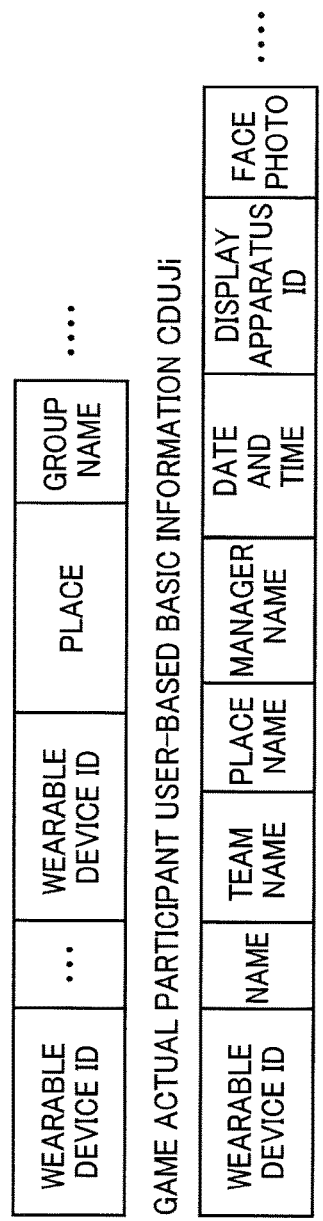

FIG. 18 (a) USER LIST

USER BASIC REGISTRATION INFORMATION UJi (UMJi;UUJi)

USER ADMINISTRATOR BASIC INFORMATION
REGISTRATION SCREEN UMGi (USER) ADMINISTRATOR BASIC
REGISTRATION INFORMATION UMJi

/241

| GROUP NAME (TEAM NAME) | GROUP (TEAM) CODE | PLACE NAME | (COMPANY NAME) | COMPANY CODE | ADMINISTRATOR (MANAGER NAME) | DISPLAY APPARATUS ID |
|---|---|---|---|---|---|---|
| ⋯ | ⋯ | ⋯ | ⋯ | ⋯ | ⋯ | ⋯ |

FIG. 18 (b) USER BASIC INFORMATION REGISTRATION SCREEN UUGi (UUJi)

PROSPECTIVE PARTICIPANT

/241

| GROUP NAME (TEAM NAME) | NAME | FACE PHOTO | AGE | WEARABLE DEVICE ID | POSITION | SEX | HEIGHT | WEIGHT | NAME CODE | MANAGER NAME |
|---|---|---|---|---|---|---|---|---|---|---|
| | | | | | | | | | | |
| | | | | | | | | | | |
| | | | | | | | | | | |
| | | | | | | | | | | |

KBGc (KBJi)

○ GROUP NAME [        ]    SOCCER FIELD [        ]
  (TEAM NAME)

Wtpi         Wtri
  ○ TIME RANGE Wti [ ○○ ] ~ [ △△ ]

○ NAME [   |   |   ] COUPLE OF PERSONS

○ POSITION DISPLAY TYPE Gki  [ FINE gdi ] [ NORMAL gi ]

○ SENSOR ACQUISITION TYPE ki
                    HEART    BODY
                    RATE   TEMPERATURE
    ● [ ALL ]  SELECT [   |   |   ]  ···· [ 9-AXIS ]
          [     ] IMAGE TYPE [ CAMERA ] or [ SIMULATED IMAGE ]

FIG. 20

KBJi

| WEARABLE DEVICE ID SECTION | | TIME RANGE Wti | SENSOR ACQUISITION TYPE ki | SOCCER FIELD NAME | TEAM NAME | DISPLAY TYPE | ... |
|---|---|---|---|---|---|---|---|
| ...ID | ...ID | Wtpi~Wtri | ALL OR SELECT (HEART RATE, ..., 9-AXIS, OR COMBINATION) | ×××  | △△ | CAMERA OR SIMULATED IMAGE | |
| ...ID | | | | | | | |

FIG. 21

TRANSMISSION PATTERN PTi

| DISPLAY APPARATUS ID | WEARABLE DEVICE ID | SENSOR ACQUISITION TYPE ki | | | TIME RANGE Wti | SYSTEM TIME STi | DETECTION POSITION Pi |
|---|---|---|---|---|---|---|---|
| | | HEART RATE | BODY TEMPER-ATURE | ... | | | |
| ...... | ...... | | | | | | ... |

FIG. 25

PLAYER A  ex 100msec  WEARABLE DEVICE ID  330ai

| SYSTEM TIME STi | FINE POSITION PWbi | FINE POSITION PWbi' | eji |
|---|---|---|---|
| 5/10/2017 15:00:00:00 | X1,Y1 | X1',Y1' | eJ1 |
| 5/10/2017 15:00:00:100 | X2,Y2 | X2',Y2' | eJ2 |
| 5/10/2017 15:00:00:200 | X3,Y3 | | |
| ............ | ............ | ............ | ............ |
| 5/10/2017 15:00:01:100 | | | |

Wtpi ex 1 MIN Wti

RDJ1, RDJ2

MOVING BODY INFORMATION PROVIDING SYSTEM AND PROGRAM

TECHNICAL FIELD

The present invention relates to a moving body information providing system.

BACKGROUND ART

Biometric information of a subject, such as a human or an animal, can be acquired at a remote location in recent years.

For example, in a biometric information monitoring system disclosed by PTL 1, a subject wears a biometric information transmission terminal that detects and transmits biometric information and the current location, and a biometric information measurement apparatus at a remote location receives the biometric information and current position and displays the same in association with each other (see paragraphs [0050] to [0054] and [0059]).

CITATION LIST

Patent Literature

PTL 1: JP 2008-272163 A

SUMMARY

Technical Problem

However, GPS receivers generally detect positions at intervals of one second while some subjects moving at high speed move several meters to a dozen meters in one second.

On the other hand, in the biometric information monitoring system described in Patent Literature 1, the current position and biometric information are transmitted from the biometric information transmission terminal at intervals of one second, and the biometric information measurement apparatus receives the current position and biometric information and displays the same in association with each other.

The biometric information monitoring system described in Patent Literature 1 cannot allow for understanding of the situation of a subject between the current and previous locations. The biometric information monitoring system does not allow for detailed understanding of the situation of a subject who is moving quickly, for example.

The present invention was made in the light of the aforementioned circumstances, and an object thereof is to provide a moving body information providing system which is able to provide detailed situations between moving body's current and previous locations detected by a GPS receiver, at a glance.

Solution to Problem

To solve the aforementioned problem, a moving body information providing system, includes:
a moving body information detection terminal that is attached to a moving body and detects the situation of the moving body; and
a moving body information analysis apparatus, the moving body information analysis apparatus and the moving body information detection terminal performing wireless communication, wherein
the moving body information detection terminal includes:
a unit that performs initial time setting based on time of the moving body information analysis apparatus and creates as moving body information, a pair of Raw data of GNSS data as the base of position detection and synchronized system time or position data obtained based on the system data and Raw data;
a unit that transmits the moving body information to the moving body information analysis apparatus, and
the moving body information analysis apparatus includes:
a position calculation data storage unit and further includes:
a unit (A) that, each time receiving the moving body information, reads the system time and position data included in the received moving body information as current fine position data information;
a unit (B) that calculates a current fine position at the system time of the current fine position data information based on the system time and system time and fine position of previous fine position data information stored in the position calculation data storage unit;
a unit (C) that displays the calculated current fine position in association with the moving body on the screen; and
a unit (D) that sets the calculated current fine position as a previous position and stores a pair of the previous fine position and the system time included in the current fine position data information, as the previous position data information in the position calculation data storage unit.

Effect

According to the present invention, the moving body information analysis apparatus displays finer interval positions than positions detected by the GNSS module, allowing the user watching the screen to understand in detail how the moving body is moving next.

The fine interval positions and position data are based on the correction data from the RTK reference station and are of high level of accuracy. In addition, the level of accuracy can be always maintained.

When the moving body is a living body, the moving body information analysis apparatus displays biometric information in association with fine interval positions. This allows the user watching the screen to understand the living body information of the moving body at fine interval positions at a glance.

When the moving body information from the moving body information detection terminal includes biometric information and moving body state information, such as posture and acceleration, the moving body information analysis apparatus displays the biometric information and moving body state information in association with each other on the screen.

When the moving body is a soccer player, for example, the user of the moving body information analysis apparatus (the manager, coach, or the like) understands the location and movement of the player and the situation at that moment on each detection position.

Furthermore, even if there are plural moving body information detection terminals, the analysis result providing apparatus is able to display the biometric information and moving body state information of the moving body from a desired moving body information detection terminal in association with each other on the screen of the portable terminal. Accordingly, the analysis result providing apparatus is able to provide the situation (current state), such as the

BRIEF DESCRIPTION OF DRAWINGS

FIG. 2 is an explanatory diagram of device management in a display apparatus (a tablet);

FIG. 3 is an explanatory diagram of association between users and wearable devices;

FIG. 4 is a flowchart illustrating an initial operation of a wearable device;

FIGS. 8(a) to 8(c) illustrate specific examples of step T29 in FIG. 7, FIG. 8(a) being an explanatory diagram in the case of associating a game time with position data of position information including previous position acquisition time, FIG. 8(b) being an explanatory diagram in the case of associating a game time with position data of position information including subsequent position acquisition time, and FIG. 8(c) being an explanatory diagram in the case of associating a game time with position data between the position data of the position information including the previous position acquisition time and the position data of the position information including the subsequent position acquisition time;

FIGS. 9(a) to 9(c) illustrate specific examples of step T31 in FIG. 7, FIG. 9(a) being an explanatory diagram in the case of associating a game time with sensor data of moving body information including previous position acquisition time, FIG. 9(b) being an explanatory diagram in the case of associating a game time with sensor data of moving body information including subsequent position acquisition time, and FIG. 9(c) being an explanatory diagram in the case of associating a game time with sensor data between the sensor data of the moving body information including the previous position acquisition time and the sensor data of the moving body information including the subsequent position acquisition time;

FIG. 14 is a diagram illustrating an example of position-included moving body information analysis result display control data;

FIG. 17(a) is a diagram illustrating an example of actual participant input information; FIG. 17(b) is a diagram illustrating an example of actual participant user pairing information; FIG. 17(c) is a diagram illustrating an example of actual participant user communication preparatory registration completion information; and FIG. 17(d) is a diagram illustrating an example of actual competition participant user-based basic information;

FIGS. 18(a) and 18(b) illustrate an example of user basic registration information, FIG. 18(a) being a diagram illustrating a display example of a user list (user administrator basic information) registration screen, FIG. 18(b) being a diagram illustrating a display example of a user basic information registration screen;

FIG. 19 is a diagram illustrating a display example of a moving body information request input screen;

FIG. 20 is a diagram illustrating an example of moving body information analysis request input information;

FIG. 21 is a diagram illustrating a transmission pattern example;

FIG. 25 is a diagram illustrating an example of fine position data information;

DESCRIPTION OF EMBODIMENTS

Figure 1:
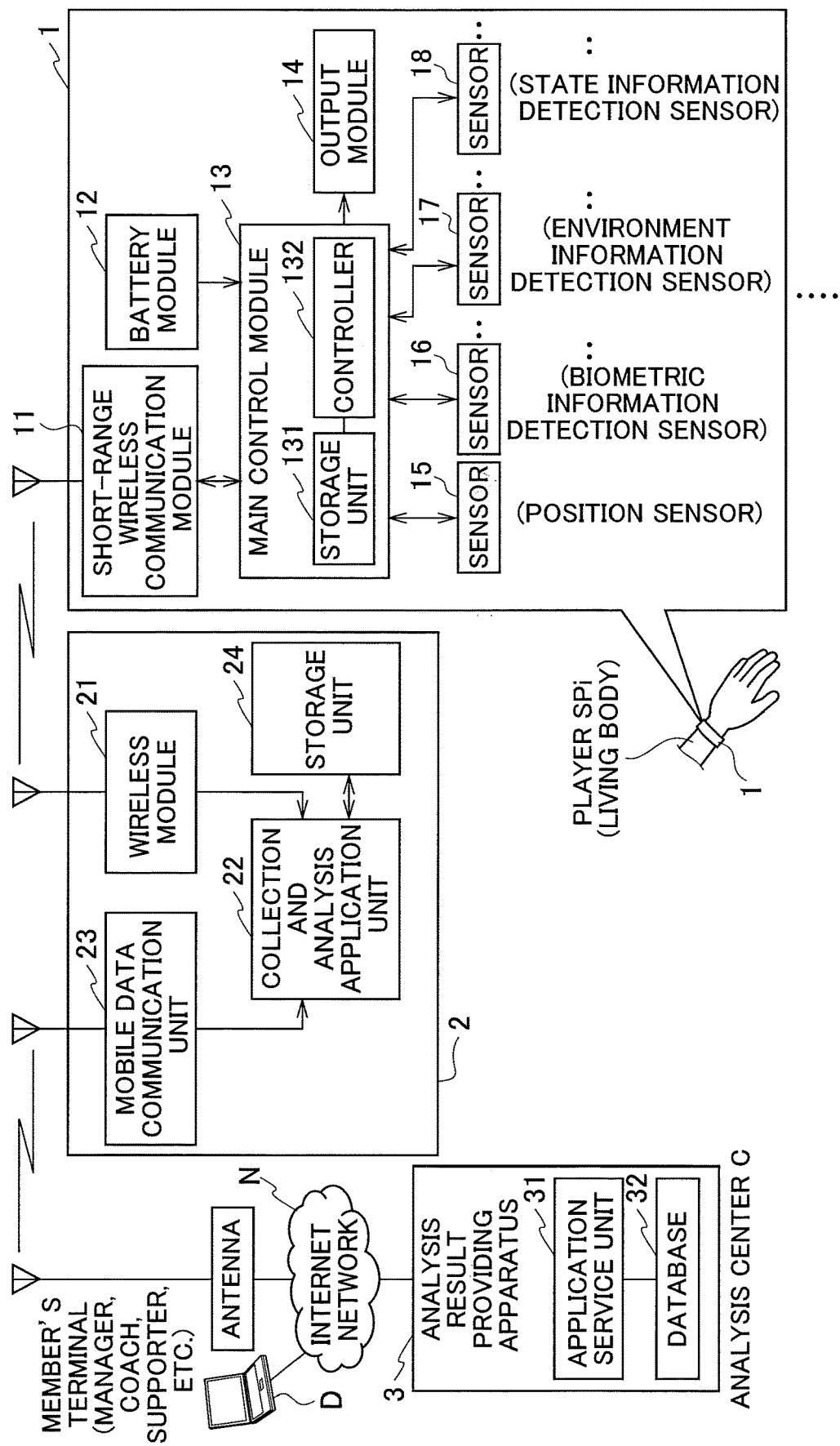
FIG. 1 is a schematic configuration diagram of a moving body information providing system according to Embodiment 1.

Hereinafter, a description is given of embodiments with reference to the drawings.

The embodiments below illustrate apparatuses and methods to embody the technical idea (structures and arrangements) of the invention. The technical idea of the invention is not identified by the followings. The technical idea of the invention can be variously changed within the matters described in claims.

It should be particularly noted that the drawings are schematic and the configurations of apparatuses and systems and the like in the drawings are different from actual ones.

The embodiments are described as a moving body information providing system which includes: a moving body information detection terminal attached to a moving living body, such as a human or an animal, as well as a moving non-living body, such as a drone, robot, or heavy equipment, including a farm machine and a construction machine, for example; a display apparatus located near the moving body information detection terminal; and an analysis result providing apparatus at a remote location from the moving body information detection terminal and display apparatus. The display apparatus and analysis result providing apparatus are collectively referred to as a moving body information analysis apparatus (an external apparatus).

The aforementioned living and non-living bodies are collectively referred to as moving bodies. The living body is preferably a marathoner, a rugby player, a soccer player, a table tennis player, a cyclist in a race, or an athlete in another kind of race, an animal, or the like.

In the following description, Embodiment 1 shows the summary of the moving body information providing system, and Embodiment 2 illustrates a specific configuration of the moving body information providing system.

Embodiment 1

FIG. 1 is a schematic configuration diagram of a moving body information providing system according to Embodiment 1.

As illustrated in FIG. 1, the moving body information providing system includes: a band-type moving body information detection terminal (hereinafter, referred to as a wearable device 1) attached to a player SPi (a moving body) as a living body; a display apparatus including a communication function, such as a portable personal computer, a tablet, or a smart phone; an analysis result providing apparatus 3 in an analysis center C; and the like.

The description of Embodiment 1 uses a tablet 2 as an example of the display apparatus.

The wearable device 1 described above performs wireless communication with the tablet 2 based on wireless communication standards, for example. The tablet 2 communicates with the analysis result providing apparatus 3, which is provided in a cloud or the like, through the Internet network N.

The wearable device 1 is attached to each of plural players SPi. The wearable device 1 is worn on a wrist of each player SPi to be used. The players SPi (soccer players or rugby players, for example) who play in a field wear the wearable devices 1 for competitions or training.

The wearable device 1 includes a wireless communication module (hereinafter, referred to as a wireless module 11), a battery module 12, a main control module 13, and an output module 14. The wearable device 1 further includes plural sensor modules.

The plural sensor modules include a position sensor 15 (also referred to as a global navigation satellite system (GNSS) module as a high-sensitive position information detection sensor), a biometric information detection sensor 16, an environment information detection sensor 17, a moving body state information detection sensor 18, and the like.

The position sensor 15 is a satellite positioning system module, such as a global positioning system (GPS), that measures the position using a later-described GNSS satellite AS1.

The biometric information detection sensor 16 includes various types of sensors, such as a heart rate sensor and a pulse sensor, that detect biometric information of the player SPi, such as the heart rate and pulse rate.

The environment information detection sensor 17 includes various types of sensors, such as an atmospheric pressure sensor and a temperature sensor, that detect surrounding information around the player SPi, such as atmospheric pressure and ambient temperature.

The moving body state information detection sensor 18 is a 9-axis sensor (also referred to as a moving body state detection module) that detects the posture of the player Spi, the speed of the player Spi, and the like. The 9-axis sensor includes a gyroscope (three axes), an accelerometer (three axes), a magnetometer (three axes), and the like.

The main control module 13 includes a storage unit 131 (also referred to as a device-side position calculation data storage unit (330)), a controller 132, and an interface connecting the both (not illustrated).

The output module 14 is composed of an LED lamp, a vibrator, an audio player (a speaker or a buzzer), and the like, for example. The battery module 12 includes a battery or a cell.

The tablet 2 is a tablet-type computer (a portable terminal) which is used by a team manager MG or coach who wants to know the relation between the position of the player SPi and the level of tiredness and the like near the player SPi (on the bench or the like), for example.

As illustrated in FIG. 1, the tablet 2 includes a tablet-side wireless module 21, a collection and analysis application unit 22, a mobile data communication unit 23, and a storage unit (hereinafter, referred to as a tablet-side storage unit 24). The tablet-side storage unit 24 is also referred to as a first position calculation data storage unit (330).

The tablet 2 can also connect to the Internet network N with the mobile data communication unit 23 through an antenna installed by a communications carrier. The analysis result providing apparatus 3 can also connect to the Internet network N. The tablet 2 and the analysis result providing apparatus 3 thereby communicate with each other.

The analysis result providing apparatus 3 includes an application service section 31 and a database 32. The application service section 31 provides information that supports performance measurements of players SPi, sensor correction, social networking service (SNS), talent matching, medical care of players SPi, training of players SPi, and the like. The database 32 stores personal data of players SPi, team data, environment data, and analysis data.

(Device Management)

FIG. 2 is an explanatory diagram of device management in the tablet 2.

When the wireless module 11 of a wearable device 1 connects to the tablet-side wireless module 21, the tablet 2 detects the originating wearable device 1 (step S1) and notifies the user interface (UI) of the wearable device 1 that the wearable device 1 of interest is connected to the tablet 2 (step S3).

Next, the tablet 2 acquires specific information to the wearable device 1 (or a device address in the case of Bluetooth (registered trademark), or a MAC address in the case of Wi-Fi (registered trademark), or a specific profile to software of the wearable device 1 when the wireless module does not have specific information) (step S5).

The device address, MAC address, and specific profile, which are the aforementioned specific information, are collectively referred to as wearable device identification information.

Next, the tablet 2 displays the specific information in a list on the screen (not illustrated) (step S7). The tablet 2 then notifies the user interface (UI) of the wearable device 1 that the wearable device 1 of interest is selected as a registration candidate (step S9).

Next, the user of the tablet 2, the manager MG, for example, visually confirms the list (step S11) and inputs user's determination whether to register the wearable device 1 of interest (step S13). When the inputted determination is to register the wearable device 1 (YES in step S15), the tablet 2 registers the wearable device 1 (step S17). In this process, the tablet 2 registers the specific information and device name (an arbitrary name) in the cloud as the information of the wearable device 1 (step S19) and notifies the user interface (UI) of the wearable device 1 of completion of registration (step S21).

(Association Between User and Wearable Device)

FIG. 3 is an explanatory diagram of association between users and wearable devices.

First, the tablet 2 acquires a user information list and a device information list from the analysis result providing apparatus 3 installed in the cloud or the like (step S31).

Next, the tablet 2 displays the user information list and device information list on a not-illustrated screen (step S33). The user of the tablet 2, the manager MG, for example, visually confirms the lists (step S35) and inputs user's determination whether to perform association (step S37).

When the inputted user's determination is to perform association (YES in step S39), the tablet 2 performs an association process (step S41). In this process, the tablet 2 registers a user ID and a wearable device ID in the cloud as association information (step S43). When the tablet 2 is connected to the wearable device 1 of interest, the tablet 2 notifies the user interface (UI) of the wearable device 1 of completion of association (step S45).

FIG. 4 is a flowchart illustrating an initial operation of the wearable device 1.

When the wearable device 1 is activated, the controller 132 requests date and time information from the position sensor 15 (step S51). The position sensor 15 then outputs a response of Raw data or GNSS data of the national marine electronic association (MNEA) format, for example, to the controller 132 (T1).

Upon receiving the response (step S53), the controller 132 determines the presence of the date and time information in the response (step S55). When the response does not include the date and time information, the controller 132 waits for the next response outputted by the position sensor 15 and receives the same (step S53).

When the response includes the date and time information, the controller 132 verifies the checksum in the GNSS data format (step S57). When verification of the checksum fails, the controller 132 waits for the next response and receives the same (step S53).

When verification of the checksum succeeds, the controller 132 checks the syntax of the GNSS data (step S59). When the syntax is invalid, the controller 132 waits for the next response and receives the same (step S53).

When the syntax is valid, the controller 132 extracts the date and time information from the response (step S61) and determines whether the date and time information is GNSS time (date and time other than in 1980, that is, the current date and time) (step S63). When the date and time information is not GNSS time, the controller 132 waits for the next response and receives the same (step S53).

When the date and time information is GNSS time (current date and time), the controller 132 determines whether three digits after the decimal point of the received GNSS time (one second or less) indicate 000 or an integer multiple of 100 (step S65). When the three digits after the decimal point do not indicate 000 or an integer multiple of 100, the controller 132 waits for the next response and receives the same (step S53).

When the three digits after the decimal point indicate 000 or an integer multiple of 100, the controller 132 sets the time (referred to as system time) of an internal timer (132i) which is provided in the controller 132 as a system clock, to the GNSS time (step S67).

The processing time from step S53 to step S67 is about a dozen milliseconds.

Next, the controller 132 receives a frame header outputted from the position sensor 15 (step S71) and determines whether the header includes 1 PPS signal (one clock waveform in one second) (step S73). When the header does not include 1 PPS signal, the controller 132 waits for the next signal and receives the same (step S71).

When the header includes 1 PPS signal, the controller 132 resets all the decimal places (one second or less) of the system time to zero and adds one second to the system time (step S75), thus terminating the initial operation.

The processing time from step S71 to step S75 is about less than one millisecond.

By the above-described initial operation, the GNSS time hereinafter transmitted from the position sensor 15 together with the position data is always equal to the system time at which the GNSS time is received.

Figure 5A:
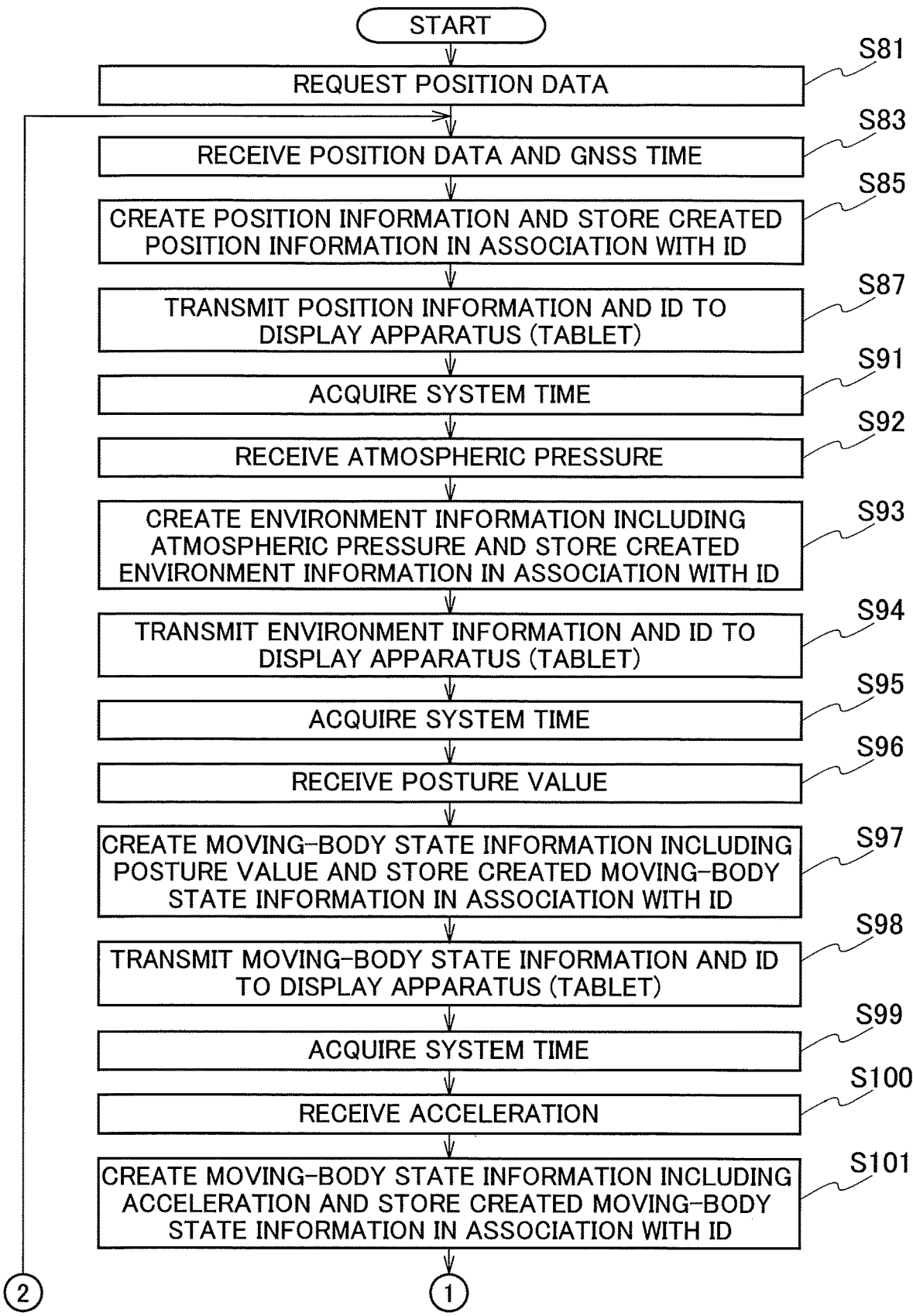
FIGS. 5A and 5B show a flowcharts of transmission by the wearable device to a tablet.
Figure 5B:
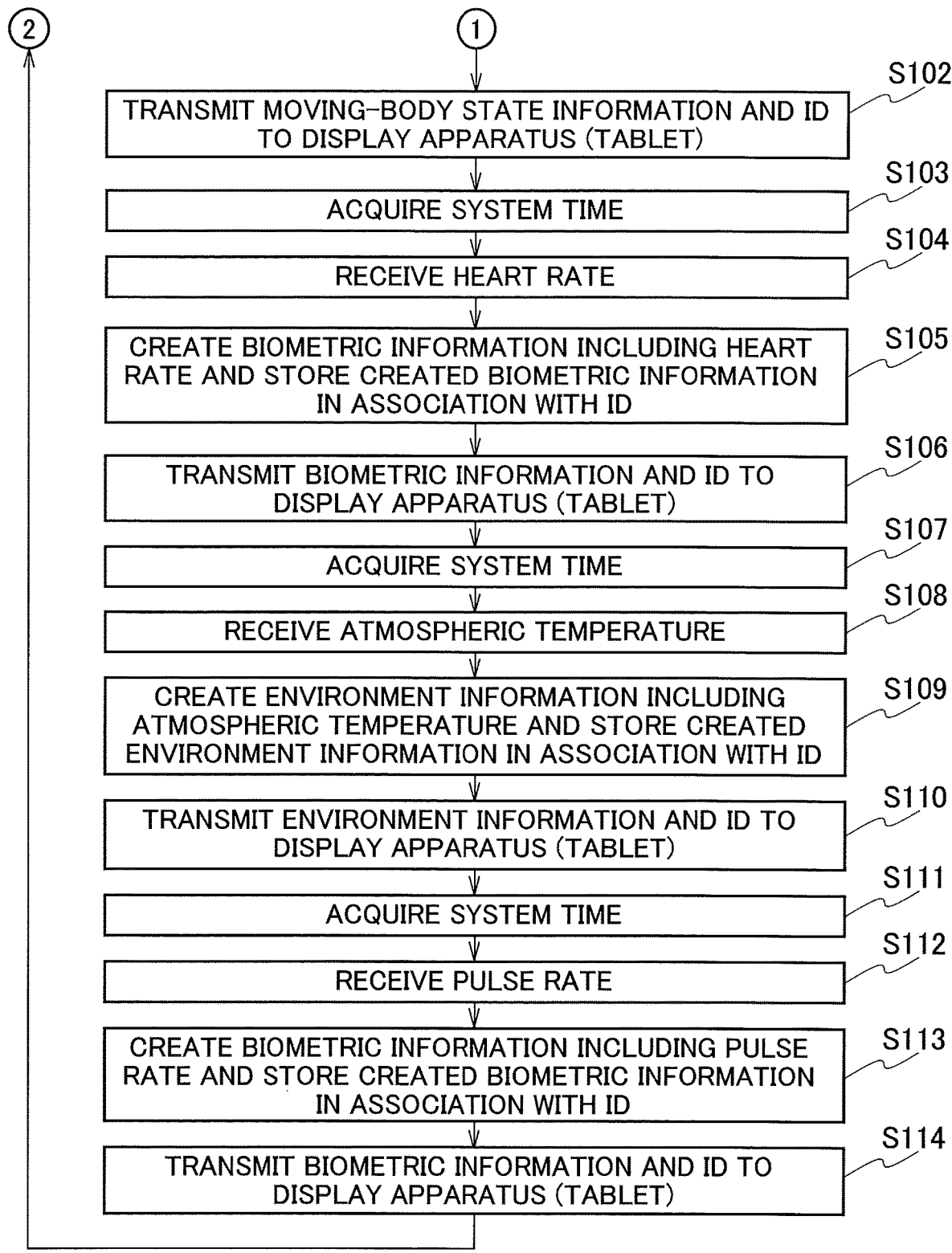

FIGS. 5A and 5B show a flowchart of the wearable device 1 transmitting moving body information and position information to the tablet 2.

After the initial operation, the controller 132 of the main control module 13 requests the position data from the position sensor 15 (step S81). The position sensor 15 thereby transmits the position data and GNSS time to the controller 132 every one second.

Upon receiving the position data and GNSS time (step S83), the controller 132 creates position information including the position data and the GNSS time as position acquisition time and stores the created position information in the storage unit 131, for example, in association with ID (identification information) indicating the player SPi who is wearing the wearable device 1 (step S85). The controller 132 also transmits the position information and ID to the tablet 2 (step S87).

The sensors other than the position sensor 15 transmit to the controller 132, sensor data (SDi) of the moving body information, including biometric information, environment information, and moving body state information at individual specific times.

When the controller 132 acquires the system time (step S91) and atmospheric pressure (step S92), for example, the controller 132 creates environment information including the sensor data of atmospheric pressure and the system time at which the sensor data is acquired and stores the created environment information in the storage unit 131 in association with the ID (step S93). The controller 132 also transmits the environment information and ID to the tablet 2 (step S94). In Embodiment 1, the system time is also referred to as sensor data acquisition time.

Next, when the controller 132 acquires the system time (step S95) and a posture value (step S96), for example, the controller 132 creates the moving body state information including the sensor data of the posture value and the system time (sensor data acquisition time) at which the sensor data is acquired and stores the created moving body state information in the storage unit 131 in association with the ID (step S97). The controller 132 also transmits the moving body state information and ID to the tablet 2 (step S98).

Next, when the controller 132 acquires the system time (step S99) and acceleration (step S100), for example, the controller 132 creates the moving body state information including the sensor data of the acceleration and the system time (sensor data acquisition time) at which the sensor data is acquired and stores the created moving body state information in a memory region 131a of the storage unit 131 in association with the ID (step S101). The controller 132 also transmits the moving body state information and ID to the tablet 2 (step S102). The above-described posture value, acceleration, direction, and the like are collectively referred to as the moving body state information.

Next, when the controller 132 acquires the system time (step S103) and the heart rate (step S104), for example, the controller 132 creates the biometric information including the sensor data of the heart rate and the system time (sensor data acquisition time) at which the sensor data is acquired and stores the created biometric information in the storage unit 131 in association with the ID (step S105). The controller 132 also transmits the biometric information and ID to the tablet 2 (step S106).

Next, when the controller 132 acquires the system time (step S107) and ambient temperature (step S108), for example, the controller 132 creates the environment information including the sensor data of the ambient temperature and the system time (sensor data acquisition time) at which the sensor data is acquired and stores the created environment information in the storage unit 131 in association with the ID (step S109). The controller 132 also transmits the environment information and ID to the tablet 2 (step S110).

Next, when the controller 132 acquires the system time (step S111) and pulse rate (step S112), for example, the controller 132 creates the biometric information including the sensor data of the pulse rate and the system time (sensor data acquisition time) at which the sensor data is acquired and stores the created biometric information in the storage unit 131 in association with the ID (step S113). The controller 132 also transmits the biometric information and ID to the tablet 2 (step S114) and returns to the step S83.

In Embodiment 1, the biometric information, environment information, and moving body state information (9-axis sensor) are also collectively referred to as the moving body information.

Figure 6:
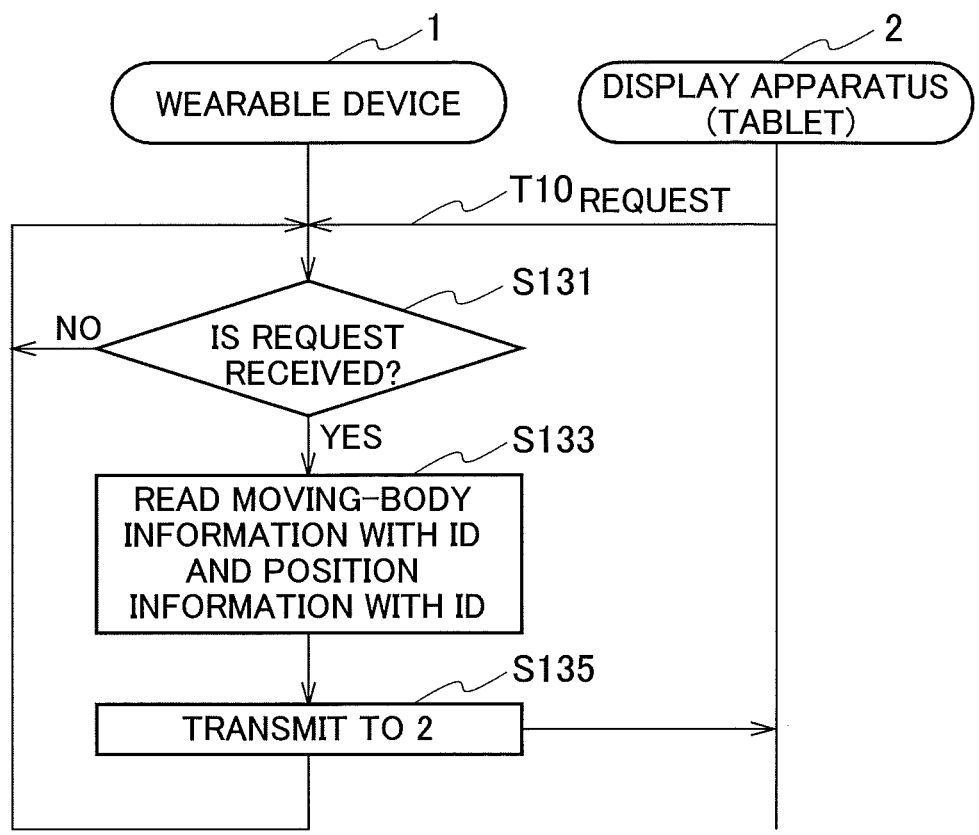
FIG. 6 is a flowchart of retransmission by the wearable device to the tablet.

FIG. 6 is a flowchart of the wearable device 1 retransmitting to the tablet 2, the moving body information, position information, and ID that the tablet 2 could not receive.

The tablet 2 transmits to the wearable device 1, a request that specifies a time period in which the tablet 2 could not receive the moving body information, position information, and ID (T10). When the length of the time period (at an interval of one second, for example) is previously determined, for example, the start time of the time period is specified.

Upon receiving the request (YES in step S131), the controller 132 of the main control module 13 of the wearable device 1 reads from the storage unit 131, the moving body information including the system time (sensor data acquisition time) within the time period specified by the request and the ID and reads the position information including the position acquisition time within the specified time period and the ID (step S133). The controller 132 then transmits the moving body information, position information, and ID to the tablet 2 (step S135) and returns to the step S131.

The tablet 2 thereby acquires the moving body information and ID and the position information and ID that the tablet 2 could not receive due to communication failure or the like.

Figure 7:
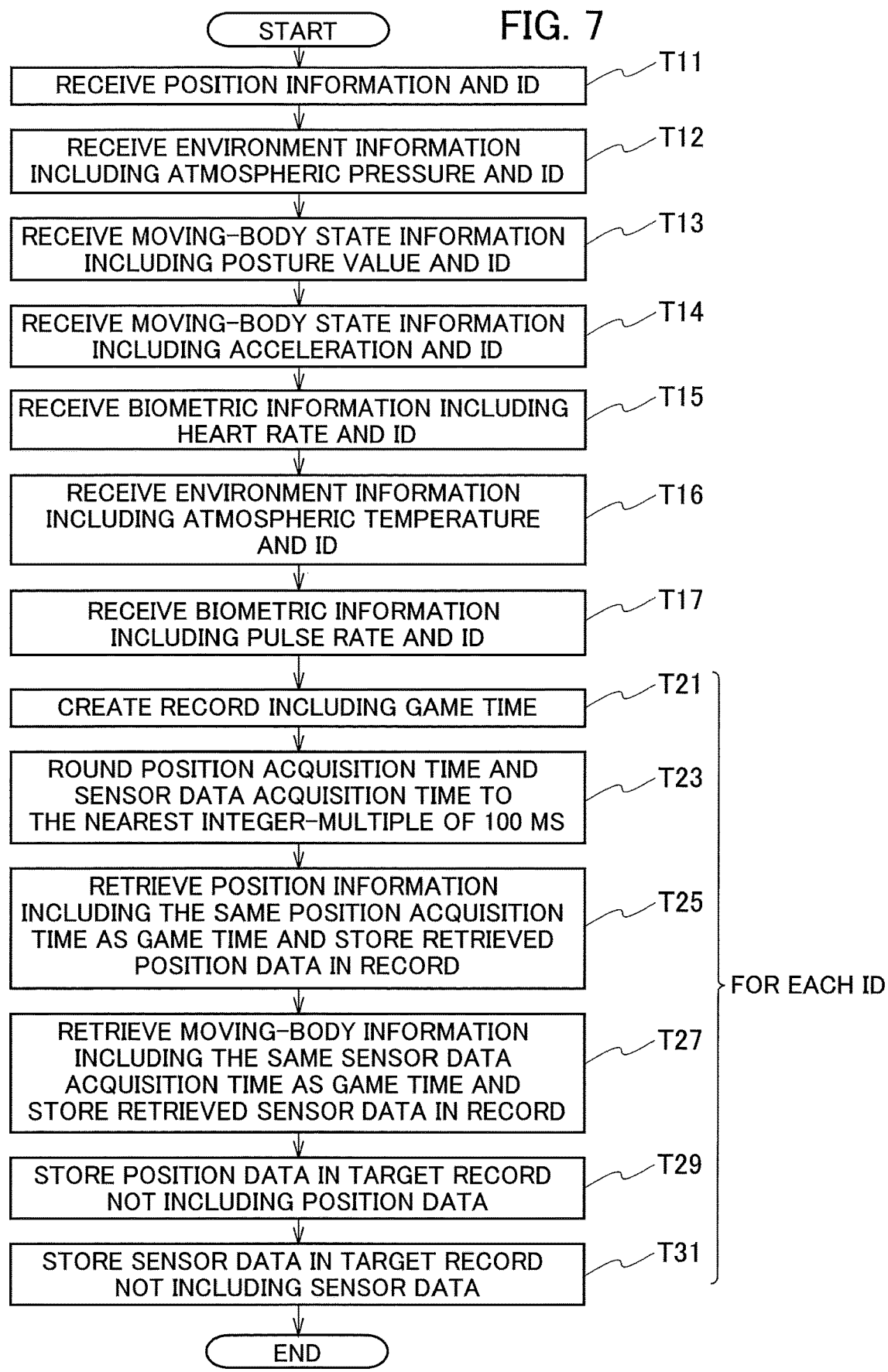
FIG. 7 is a flowchart of processing in the tablet.

FIG. 7 is a flowchart of processing in the tablet 2.

The tablet-side wireless module 21 of the tablet 2 receives the position information and the ID from the wearable device 1 (step T11), receives the environment information including the atmospheric pressure and the ID (step T12), receives the moving body state information including the posture value and the ID (step T13), receives the moving body state information including acceleration and the ID (step T14), receives the biometric information including the heart rate and the ID (step T15), receives the environment information including the ambient temperature and the ID (step T16), and receives the biometric information including the pulse rate and the ID (step T17).

A collection and analysis application unit 22 of the tablet 2 performs processing for each ID as follows after a game of soccer or the like, for example.

First, for each of all times in the game set at intervals of 100 ms (hereinafter, referred to as game times), that is, for each of previously determined times, the collection and analysis application unit 22 creates a record including the game time in the tablet-side storage unit 24 (step T21).

Next, the collection and analysis application unit 22 rounds up or down the position acquisition time of the received position information and the sensor data acquisition time of the received moving body information to the nearest 100 ms (step T23). The collection and analysis application unit 22 may calculate the difference in time between the rounded and unrounded values.

Next, for each record, the collection and analysis application unit 22 retrieves the position information including the same position acquisition time as the game time of the record and reads the position data from the retrieved position information to store the same in the record (step T25).

Next, for each record, the collection and analysis application unit 22 retrieves the moving body information including the same sensor data acquisition time as the game time of the record and reads the sensor data from the retrieved moving body information to store the same in the record (step T27).

Next, the collection and analysis application unit 22 stores position data in each record not including any position data (referred to as a target record) (step T29).

In this process, for example, the collection and analysis application unit 22 retrieves a record including position data and the game time which is earlier than and the nearest to the game time of the target record and stores the same position data as that of the retrieved record in the target record. The collection and analysis application unit 22 thus associates the game time of the target record with the position data of the position information including the previous position acquisition time.

As illustrated in FIG. 8(a), when the target record has a game time of YYYY/MM/DD:HH:MM:01.200 and the retrieved record has a game time of YYYY/MM/DD:HH:MM:01.100 and includes latitude E1 and longitude N1, for example, the collection and analysis application unit 22 stores the latitude E1 and longitude N1 in the target record.

Alternatively, the collection and analysis application unit 22 retrieves a record including position data and the game time which is later than and the nearest to the game time of the target record and stores the same position data as that of the retrieved record in the target record. The collection and analysis application unit 22 thus associates the game time of the target record with the position data of the position information including the subsequent position acquisition time.

As illustrated in FIG. 8(b), when the target record includes a game time of YYYY/MM/DD:HH:MM:01.200 and the retrieved record includes a game time of YYYY/MM/DD:HH:MM:01.300 and includes latitude E2 and longitude N2, for example, the collection and analysis application unit 22 stores the latitude E2 and longitude N2 in the target record.

Alternatively, the collection and analysis application unit 22 retrieves a record including position data and the game time which is earlier than and the nearest to the game time of the target record and retrieves a record including position data and the game time which is later than and the nearest to the game time of the target record. The collection and analysis application unit 22 stores the position data indicating the position between the positions indicated by the position data of the two retrieved records, in the target record. The collection and analysis application unit 22 thus associates the game time of the target record with the position data between the position data of the position information including the previous position acquisition time and the position data of the position information including the subsequent position acquisition time.

As illustrated in FIG. 8(c), when the target record includes a game time of YYYY/MM/DD:HH:MM:01.200; one of the retrieved records has a game time of YYYY/MM/DD:HH:MM:01.100 and includes the latitude E1 and longitude N1; and the other retrieved record includes a game time of YYYY/MM/DD:HH:MM:01.300 and includes the latitude E2 and longitude N2, for example, the collection and analysis application unit 22 stores latitude=(E1+E2)/2 and longitude=(N1+N2)/2 in the target record. The position data to be stored in a record not including any position data is the average of the position data of the position information including the previous position acquisition time and the position data of the position information including the subsequent position acquisition time. The processing illustrated in FIG. 8(c) may be omitted if unnecessary.

Next, the collection and analysis application unit 22 stores sensor data in each record not including any sensor data (referred to as a target record) (step T31).

The collection and analysis application unit 22 retrieves a record including sensor data and the game time which is earlier than and the nearest to the game time of the target record and stores the same sensor data as that of the retrieved record in the target record. The collection and analysis application unit 22 thus associates the game time of the target record with the sensor data of the moving body information including the previous sensor data acquisition time.

As illustrated in FIG. 9(a), when the target record includes a game time of YYYY/MM/DD:HH:MM:01.200 and the retrieved record includes a game time of YYYY/MM/DD:HH:MM:01.100 and includes a heart rate "54", for example, the collection and analysis application unit 22 stores the heart rate "54" in the target record.

The collection and analysis application unit 22 retrieves a record including sensor data and the game time which is later than and the nearest to the game time of the target record and stores the same sensor data as that of the retrieved record in the target record. The collection and analysis application unit 22 thus associates the game time of the target record with the sensor data of the moving body information including the subsequent sensor data acquisition time.

As illustrated in FIG. 9(b), when the target record includes a game time of YYYY/MM/DD:HH:MM:01.200 and the retrieved record includes a game time of YYYY/MM/DD:HH:MM:01.300 and includes a heart rate "63", for example, the collection and analysis application unit 22 stores the heart rate "63" in the target record.

Alternatively, the collection and analysis application unit 22 retrieves a record including sensor data and the game time which is earlier than and the nearest to the game time of the target record and retrieves a record including sensor data and the game time which is later than and the nearest to the game time of the target record. The collection and analysis application unit 22 stores the sensor data between the sensor data of the two retrieved records in the target record. The collection and analysis application unit 22 thus associates the game time of the target record with the sensor data between the sensor data of the moving body information including the previous sensor data acquisition time and the sensor data of the moving body information including the subsequent sensor data acquisition time.

As illustrated in FIG. 9(c), when the target record includes a game time of YYYY/MM/DD:HH:MM:01.200; one of the retrieved records includes a game time of YYYY/MM/DD:HH:MM:01.100 and includes a heart rate "54"; and the other retrieved record includes a game time of YYYY/MM/DD:HH:MM:01.300 and includes a heart rate "63", for example, the collection and analysis application unit 22 stores a heat rate "58.5" (=(54+63)/2) in the target record. The sensor data stored in the record not including any sensor data is an average of the sensor data of the moving body information including the previous sensor data acquisition time and the sensor data of the moving body information including the subsequent sensor data acquisition time. The processing illustrated in FIG. 9(c) may be omitted if unnecessary.

The processing in FIG. 7 allows every record to include position data and sensor data. This means that, for the game time of each record, position data and sensor data at the same game time are obtained.

The collection and analysis application unit 22 transmits information of all the records to the analysis result providing apparatus 3 through the mobile data communication unit 23, for example.

The application service unit 31 of the analysis result providing apparatus 3 receives the information of all the records and performs various information analyses.

When the players SPi are soccer players SPai, for example, the position data and acceleration (sensor data) at the same time are obtained for the same ID (the same soccer player SPai). When particular position data (the position in front of the opponent's goal, for example) is connected to a lot of comparatively high accelerations, it is determined that the soccer player SPai of interest is excellent in instantaneous movement in front of the opponent's goal and is suitable for a forward position.

When particular position data (the position in front of the team's own goal, for example) is connected to a lot of comparatively high heart rates or pulse rates irrespectively of IDs, it is determined that the team is likely to be needlessly distracted in front of the team's own goal.

When the posture value connected to specific position data (the position near sidelines, for example) of a certain ID (the same soccer player SPai) do not change so much, it is determined that the soccer player SPai of interest does not frequently come into contact with opponent players near side lines and is suitable for a side back position.

The application service section 31 of the analysis result providing apparatus 3 transmits the results of such analyses to the tablet 2, and the tablet 2 displays the received analysis results on the display section or the like. The manager MG or coach looking at the displayed analysis results can use the analysis results for substitution of players or changes in strategies.

In Embodiment 1, IDs are used to distinguish the players. However, IDs are unnecessary if it is unnecessary to distinguish the players. For example, IDs are unnecessary in the case of acquiring position data and sensor data of the only track athlete (living body) in the own country at the same time. The rounding process in steps T25 and T27 may be omitted.

As described above, the moving body information providing system of Embodiment 1 includes the wearable device 1 attached to a moving body and the tablet 2 that is able to communicate with the wearable device 1. The wearable device 1 includes: the position sensor 15 that acquires position data of the moving body; the biometric information detection sensor 16 that acquires biometric information of the moving body; the environment information detection sensor 17 that acquires environment information, including atmospheric pressure and ambient temperature around the moving body; and the moving body state information detection sensor 18 that acquires moving body state information including the posture, speed, and the like of the moving body. The wearable device 1 further includes the main control module 13 that properly transmits to the tablet 2, position information including the position data and the position acquisition time at which the position data is acquired and the sensor data and the sensor data acquisition time at which the sensor data is acquired.

The tablet 2 includes the collection and analysis application unit 22. For previously determined times (game times in the above example), the collection and analysis application unit 22 associates a time (a game time) with the sensor data of the moving body information including the previous or subsequent sensor data acquisition time to the time (game time) of interest (step T31). The collection and analysis application unit 22 also associates a time (a game time) with the position data of the position information including the previous or subsequent sensor data acquisition time to the time (game time) of interest (the step T29). For each record in the above example, therefore, the position data and sensor data of the moving body at substantially the same time are obtained.

For example, the collection and analysis application unit 22 associates a time (a game time) with sensor data between the sensor data of the moving body information including the previous sensor data acquisition time and the sensor data of the moving body information including the subsequent sensor data acquisition time (step T31). The collection and analysis application unit 22 also associates a time (a game time) with the position data between the position data of the position information including the previous position acquisition time and the position data of the position information including the subsequent position acquisition time (step T29). For each record in the above example, therefore, the position data and sensor data of the moving body at substantially the same time are obtained.

The sensor data between the sensor data of the moving body information including the previous sensor data acquisition time and the sensor data of the moving body information including the subsequent sensor data acquisition time is an average of the sensor data of the moving body information including the previous sensor data acquisition time and the sensor data of the moving body information including the subsequent sensor data acquisition time. The sensor data (average) is thereby stored in each record of the above example, and the position data and sensor data of the moving body at substantially the same time are obtained.

The position data between the position data of the position information including the previous position acquisition time and the position data of the position information including the subsequent position acquisition time is the average of the position data of the position information including the previous position acquisition time and the position data of the position information including the subsequent position acquisition time. The position data (average) is thereby stored in each record of the above example, and the position data and sensor data of the moving body at substantially the same time are obtained.

The tablet 2 is a communication apparatus which is able to communicate with the wearable device 1 attached to the moving body. The collection and analysis application unit 22 receives from the wearable device 1, the position information including the position data of the moving body and the position acquisition time at which the position data is acquired and the sensor data representing the conditions of the moving body or the conditions around the same and the sensor data acquisition time at which the sensor data is acquired (steps T11 to T17). For previously determined times (the game times in the above example), the collection and analysis application unit 22 also associates a time (game time) with the sensor data of the moving body information including the previous or subsequent sensor data acquisition time to the time (game time) of interest (step T31) and associates a time (a game time) with the position data of the position information including the previous or subsequent sensor data acquisition time to the time (game time) of interest (step S29). For each record in the above example, therefore, the position data and sensor data of the moving body at substantially the same time are obtained.

Computer programs causing computers to function as the wearable device 1 or tablet 2 can be recorded in a computer-readable recording medium, such as a semiconductor memory, a magnetic disk, an optical disk, a magneto-optical disk, or a magnetic tape, and can be transmitted through a communication network, such as the Internet, to be widely distributed.

Embodiment 2

Figure 10:
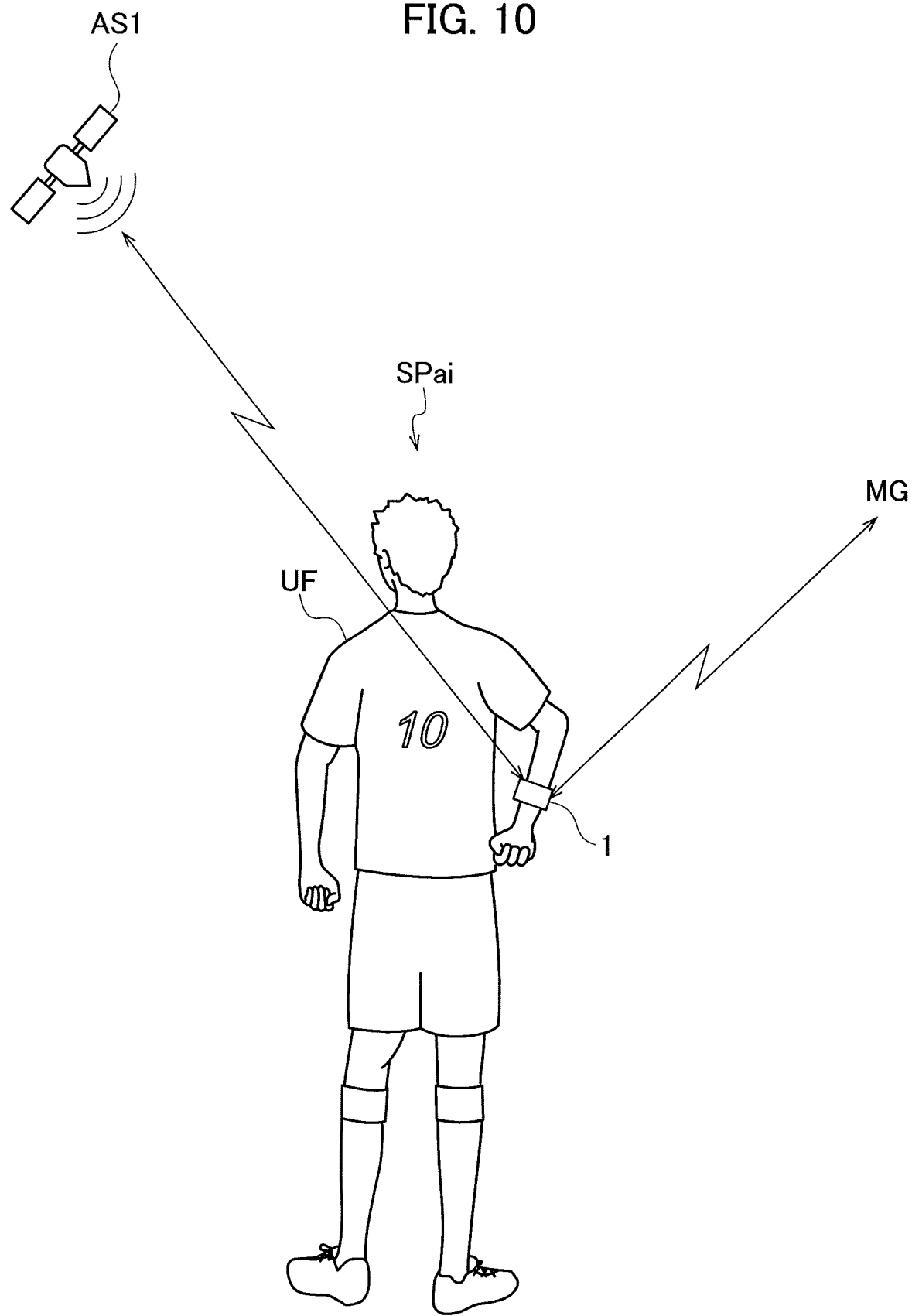
FIG. 10 is a diagram illustrating an attachment example of the wearable device of the moving body information providing system according to Embodiment 2.

Next, a moving body information providing system according to Embodiment 2 is described with a more specific example. Embodiment 2 is described as an example in which the wearable device 1 is worn on a wrist of the soccer player SPai (a moving body) as a player (living body) as illustrated in FIG. 10.

The wireless communication protocol may be Wi-Fi (registered trademark), Bluetooth (registered trademark), or the like. In the description of Embodiment 2, the wireless communication protocol is Bluetooth (registered trademark).

The moving body information providing system may be a system that analyzes the situation of soccer players SPai (Spa1, Spa2, ... ) in plural soccer fields Ai and provides the analysis results to the tablet 2, an external member's terminal D, or the like, for example. Embodiment 2 is described by using a single soccer field Ai as illustrated in FIG. 11.

In the description, the cloud is the analysis result providing apparatus 3 in the analysis center C connected to the Internet network N.

Figure 11:
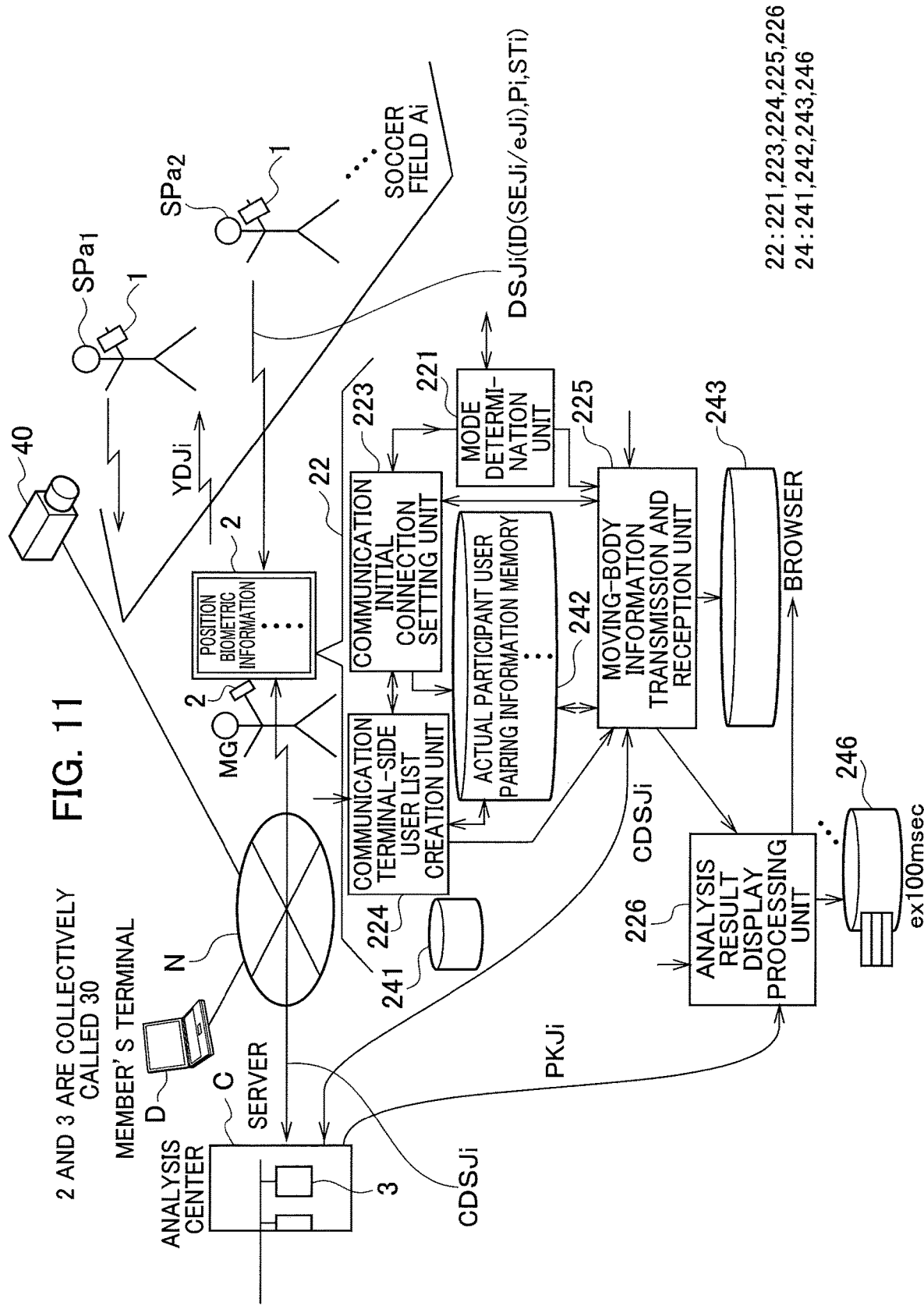
FIG. 11 is a schematic configuration diagram illustrating a specific example of the moving body information providing system.

FIG. 11 is a schematic configuration diagram illustrating a specific example of the moving body information providing system according to Embodiment 2.

As illustrated in FIG. 11, the moving body information providing system includes: plural wearable devices 1 worn on the wrists of the respective soccer players SPai (Spa1, Spa2, ... ) in the soccer field Ai; the tablet 2 held by the manager MG or the like; the analysis result providing apparatus 3 in the analysis center C; and the like. The analysis results by the analysis result providing apparatus 3 in the analysis center C may be viewable in plural member's terminals D, for example.

The analysis result providing apparatus 3 in the analysis center C and the tablet 2 are connected via the Internet network N, and each wearable device 1 and the tablet 2 are connected via a wireless communication protocol, such as Bluetooth (registered trademark) or Wi-Fi (registered trademark).

The tablet 2 and the analysis result providing apparatus 3 in the analysis center C are collectively referred to as a moving body information analysis apparatus 30.

The wearable devices 1 are attached to uniforms UF or the like of the respective soccer players Spai, for example.

In Embodiment 2, sensor data SDi that are obtained by sensing are referred to as biometric information SEJi and moving body state information. The biometric information SEJi includes the heart rate, pulse rate, body temperature, and the like.

The moving body state information is information including the posture value, acceleration, and direction detected by a 9-axis sensor (a moving body state information detection sensor) and the like (representing movement). In the description of Embodiment 2, the moving body state information is referred to as a 9-axis sensor information eJi.

In the description of Embodiment 2, as illustrated in FIG. 11, at least a camera 40 to capture images of the soccer field Ai is provided at a proper place of the soccer field Ai. The camera 40 preferably includes plural cameras, which are provided at proper places to capture images of the soccer field Ai from above, from the sides, and in a perspective view. In the case of not using the camera 40, a simulated planar image (illustration) of the soccer field Ai is used. In the description, the position sensor 15 is a GNSS module (a GPS module).

After performing an initial time synchronization process and a pairing initial setting process, the wearable device 1 associates the biometric information SEJi (heart rate, body temperature, ... ) and 9-axis sensor information eJi (acceleration, posture value, and direction) which are acquired at regular intervals with the position data (the latitude Ei and longitude Ni) of the position sensor 15, which is a GNSS module, system time STi, and the like.

Figure 12:
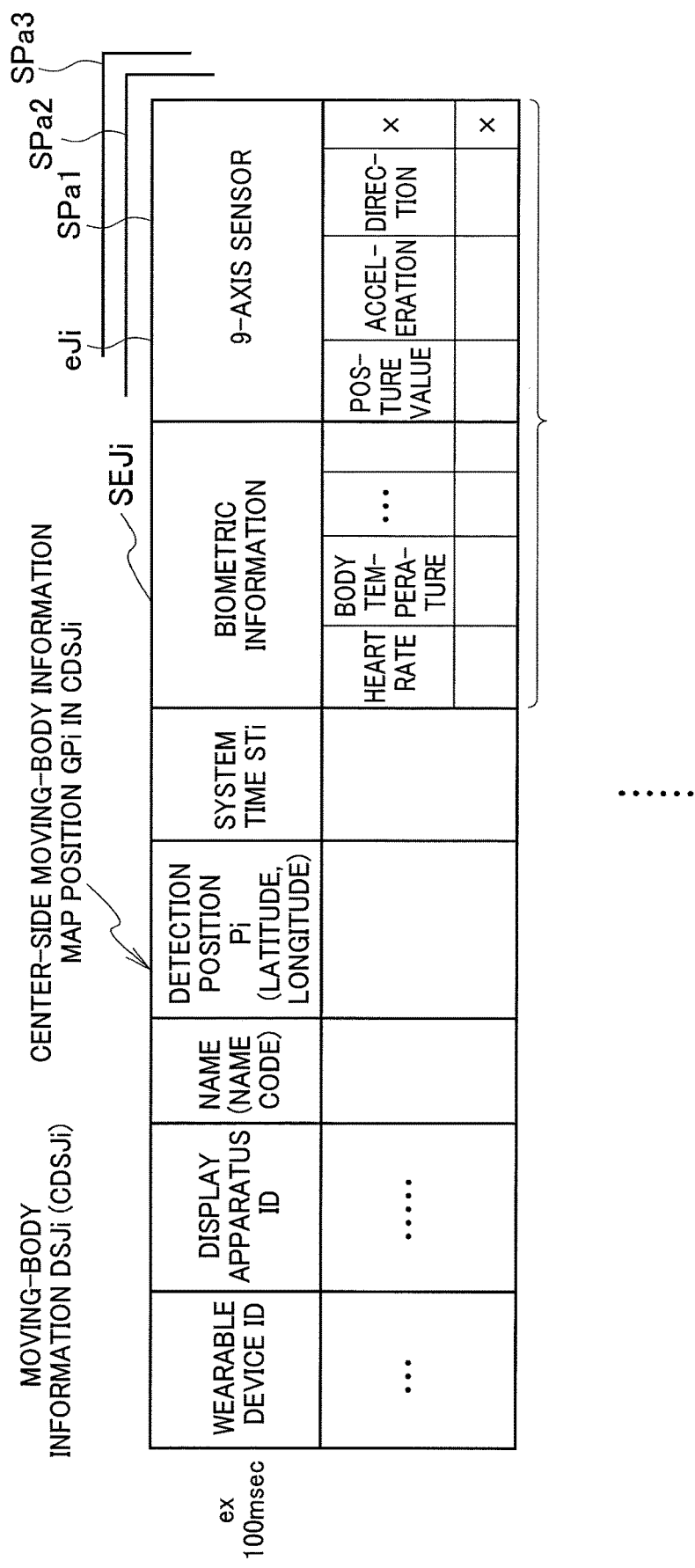
FIG. 12 is a diagram illustrating an example of moving body information.

The wearable device 1 transmits the moving body information DSJi illustrated in FIG. 12 to the tablet 2 via the Bluetooth (registered trademark) protocol through the wireless module 11, for example. In Embodiment 2, the position data is referred to as detection position Pi.

The moving body information DSJi is transmitted to the tablet 2 in a pattern based on a later-described transmission pattern PTi transmitted from the tablet 2.

As illustrated in FIG. 12, for example, the moving body information DSJi includes the wearable device ID, tablet ID, name (name code), detection position Pi, system time STi, biometric information SEJi, 9-axis sensor information eJi, and the like. In the case of later-described center-side moving body information CDSJi, the detection position Pi is map position GPi.

The initial time of the system time STi is synchronized with that of internal timers (not illustrated) provided for the analysis center C and tablet 2.

The biometric information SEJi and 9-axis sensor information eJi are collectively referred to as sensor data SDi (see FIG. 12). The moving body information DSJi may include detection position Pi, acquisition (detection) time thereof, and the like. The system time STi is preferably at a 100 ms basis, for example. The detection position Pi by the 1 PPS signal is preferably outputted at intervals of one second, for example.

The sensor data SDi includes all, a combination, or one of the heart rate, pulse rate, body temperature, and the like, which are obtained at that moment.

The 9-axis sensor information eJi includes all, a combination, or one of the posture value, acceleration, and direction, which are obtained by the wearable device 1 at that moment.

The biometric information SEJi and 9-axis sensor information eJi may individually include acquisition time at which the biometric information SEJi and 9-axis sensor information eJi are obtained, respectively. The acquisition time preferably uses the system time STi.

Figure 13:
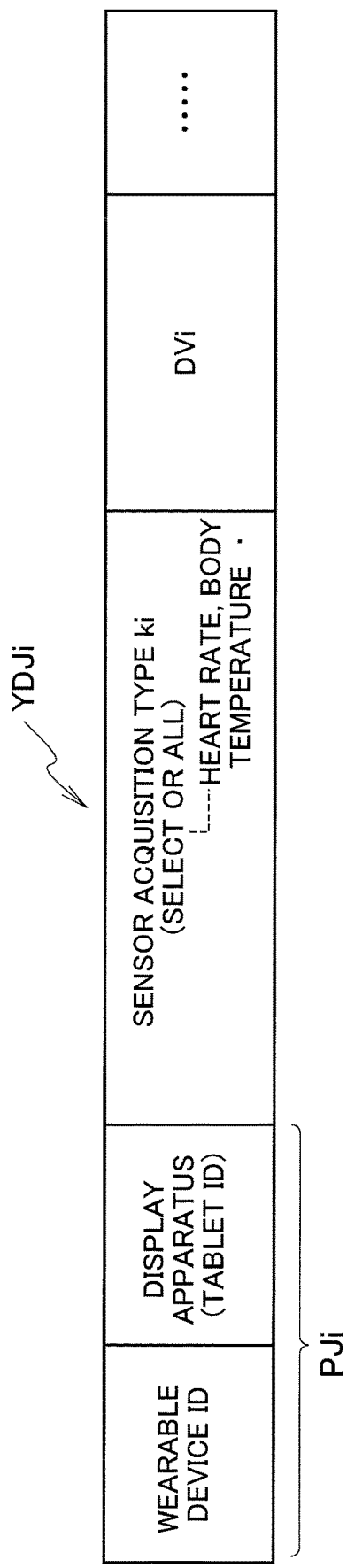
FIG. 13 is a diagram illustrating an example of moving body information request information.

After performing the pairing initial setting process with each wearable device 1, the tablet 2 simultaneously transmits moving body information request information YDJi (see FIG. 13) that requests the moving body information DSJi, to each wearable device 1.

The tablet 2 acquires the moving body information DSJi (see FIG. 12) corresponding to the moving body information request information YDJi (see FIG. 13) and transmits the acquired moving body information DSJi (see FIG. 12) to the analysis result providing apparatus 3 via the Internet protocol.

The tablet 2 receives display control data PKJi (including the camera image CGi) transmitted from the analysis result providing apparatus 3 (illustrated in FIG. 14) and the like via the Internet protocol and displays the same on the screen.

The analysis result providing apparatus 3 in the analysis center C receives the moving body information DSJi (see FIG. 12) from the tablet 2 and analyses the current conditions of the soccer players SPa1, Spa2, Spa3, ... based on the received moving body information DSJi and past moving body information DSJi, for example.

Figure 15:
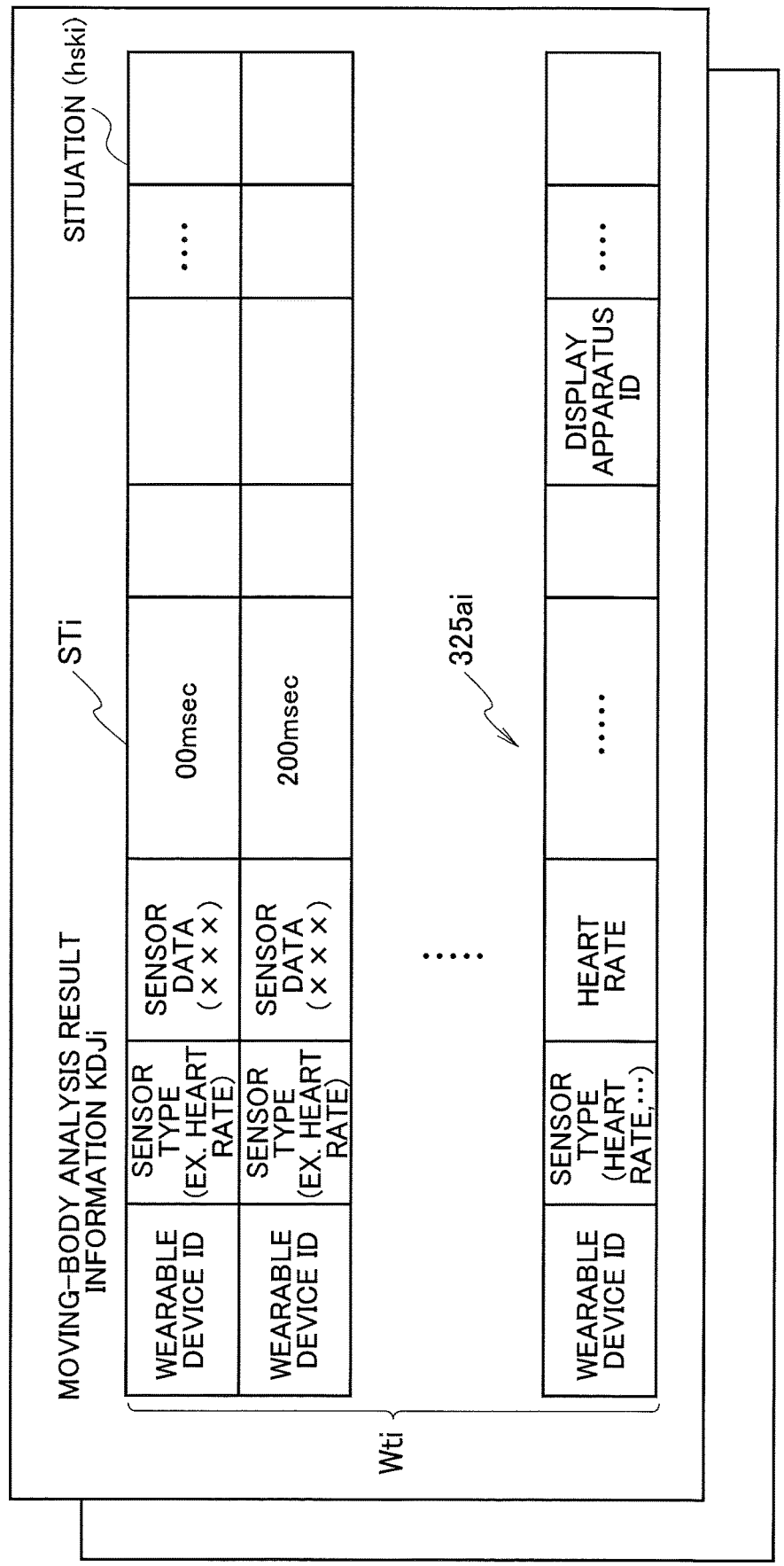
FIG. 15 is a diagram illustrating an example of moving body analysis result information.

Based on moving body information analysis result information KDJi (see FIG. 15) summarizing the analysis results, the analysis result providing apparatus 3 adds the positions (detection positions Pi, for example) of the soccer players Spa1, Spa2, Spa3, ... in the soccer field Ai thereto to create the display control data PKJi (also referred to as just control data) and transmits the created display control data PKJi to the tablet 2 through the Internet network N.

The tablet 2 is able to display the moving body information DSJi (see FIG. 12) received from the wearable devices 1 and the detection positions Pi at the same time in association with each other. The tablet 2 is thereby able to notify the manager MG in the site (in front of the bench of the soccer field Ai, for example) of the current conditions (the positions, biometric information, movements, and the like) of the soccer players Spa1, Spa2, Spa3, . . . in real time.

(Configuration of Component)

The specific configuration of each component of Embodiment 2 is described, sequentially in order of the tablet 2, wearable device 1, and analysis result providing apparatus 3.

[Tablet 2]

As illustrated in FIG. 11, the collection and analysis application unit 22 of the tablet 2 includes a mode determination unit 221, a communication initial connection setting unit 223, a communication terminal-side user list creation unit 224, a moving body information transmission and reception unit 225, an analysis result display processing unit 226, and the like. In the description, it is assumed that a collection and analysis application icon (not illustrated) indicating that the collection and analysis application unit 22 is installed is displayed on the screen.

The above-described tablet-side storage unit 24 (see FIG. 1) includes a communication terminal-side user list memory 241, an actual participant user pairing information memory 242, a moving body information memory 243, an analysis result reception memory 246, and the like.

[[Mode Determination Unit 221]]

Figure 16:
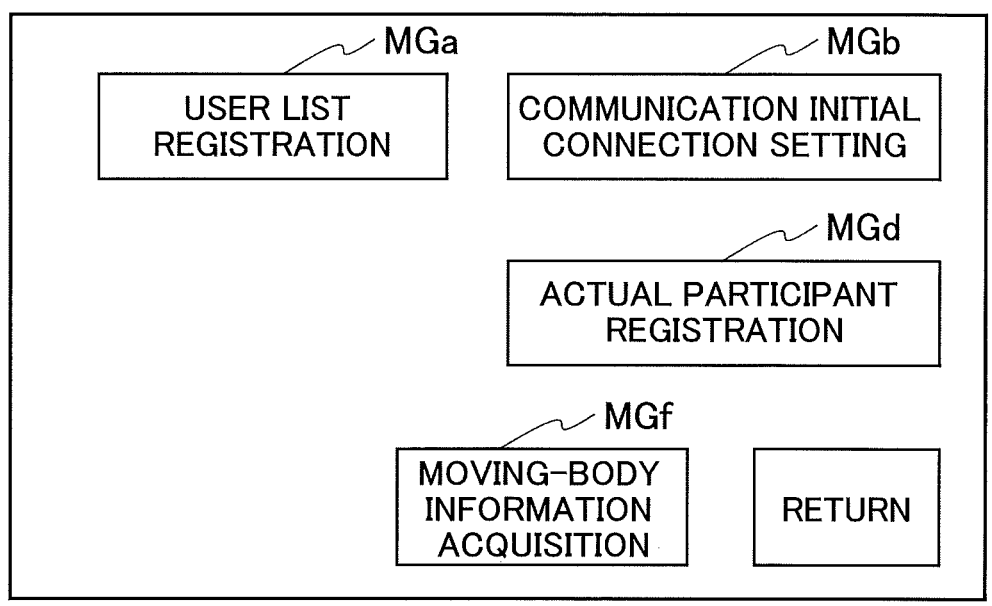
FIG. 16 is a diagram illustrating a display example of a mode selection screen in the tablet.

When a position-included moving body information providing tablet icon (not illustrated) is selected on the screen, the mode determination unit 221 displays a mode selection screen MGi (see FIG. 16).

[[Communication Initial Connection Setting Unit 223]]

The communication initial connection setting unit 223 transmits pairing request information (the tablet ID, device type, maker, time, and the like) to each wearable device 1 and performs pairing with the wearable device 1. The communication initial connection setting unit 223 then acquires pairing information PJi (see FIG. 13).

The communication initial connection setting unit 223 then waits for an output of the moving body information request information YDJi from the later-described moving body information transmission and reception section 225.

When the moving body information request information YDJi is outputted and actual participant user pairing information RPJi (see FIG. 17(b)) including the pairing information PJi included in the outputted moving body information request information YDJi is registered in the actual participant user pairing information memory 242, the communication initial connection setting unit 223 performs pairing setting via the Bluetooth (registered trademark) protocol.

The communication initial connection setting unit 223 is preferably activated when the soccer player SPai turns on the wearable device 1 just before entering the soccer field Ai, for example.

The communication initial connection setting unit 223 sequentially outputs the pairing information PJi to the communication terminal-side user list creation unit 224.

The communication initial connection setting unit 223 includes plural channels and is able to simultaneously communicate with several wearable devices 1, for example.

In Embodiment 2, the wearable device ID is a unique code generated based on the soccer field name (code), place name (code), device number specific to the wearable device 1, group name (code), place (code), a random number, and the like. The wearable device ID is a wearable device identification code that identifies the user and group of the wearable device 1 and the place where the wearable device 1 is used.

Each time that the communication initial connection setting unit 223 receives the moving body information DSJi (see FIG. 12) corresponding to the moving body information request information YDJi (see FIG. 13) from each wearable device 1, the communication initial connection setting unit 223 accepts the moving body information DSJi when the actual participant user pairing information RPJi (see FIG. 17(b)) that includes the wearable device ID included in the received moving body information DSJi is already registered in the actual participant user pairing information memory 242.

The communication initial connection setting unit 223 outputs the moving body information DSJi to the moving body information transmission and reception unit 225 for transmission to the analysis result providing apparatus 3.

[[Communication Terminal-Side User List Creation Unit 224]]

When activated, the communication terminal-side user list creation unit 224 previously transmits user registration information as user basic registration information UJi (see FIGS. 18(a) and 18(b)) to the analysis result providing apparatus 3 through the Internet network N as illustrated in FIG. 18. The user registration information allows the service to be provided and includes names of soccer players SPai, wearable device IDs of the wearable devices 1, and the like. The user basic registration information UJi may be registered by the center side in advance.

The communication terminal-side user list creation unit 224 also previously registers in the analysis result providing apparatus 3, the aforementioned actual participant user pairing information RPJi (see FIG. 17(b)) that includes the pairing information RE of the wearable devices 1 worn by the soccer players SPai who will actually participate in the game and the tablet 2, with the names and the like added thereto (the communication terminal-side user list creation unit 224 may register the actual participant user pairing information RPJi during the game).

Specifically, to previously register the actual participant user pairing information RPJi, the communication terminal-side user list creation unit 224 displays an actual participant input screen ZGi illustrated in FIG. 17(a) when an actual participant registration button MGd illustrated in FIG. 16 is selected.

When an OK button MGg in the actual participant input screen ZGi is selected, the communication terminal-side user list creation unit 224 transmits the information inputted in the actual participant input screen ZGi as actual participant input information ZGJi (see FIG. 17(a)), to the analysis result providing apparatus 3 through the Internet network N.

When the communication terminal-side user list creation unit 224 receives actual participant user-based basic information CDUJi (see FIG. 17(d)) corresponding to the actual participant input information ZGJi from the analysis result providing apparatus 3, the communication terminal-side user list creation unit 224 then waits for pairing.

After pairing, the communication terminal-side user list creation unit 224 reads the pairing information PJi that includes the wearable device ID and tablet ID included in the actual participant user-based basic information CDUJi, from the communication initial connection setting unit 223.

The actual participant user-based basic information CDUJi (see FIG. 17(d)) includes a face photograph of the soccer player SPai actually participating in the game, the wearable device ID of the wearable device 1 worn by the soccer player SPai, and the like.

In the aforementioned actual participant user-based basic information CDUJi, preferably, the team name and player's name are registered in this order at the top.

The communication terminal-side user list creation unit 224 associates the read pairing information PJi with the received actual participant user-based basic information CDUJi and then stores the same in the actual participant user pairing information memory 242, as the aforementioned actual participant user pairing information RPJi (see FIG. 17(b)) of the soccer player SPai who is actually participating in the game at that moment.

The communication terminal-side user list creation unit 224 reads the actual participant user pairing information memory 242 and displays the actual participant user pairing information RPJi on the screen.

The user of the tablet 2 (the manager MG, for example) is able to understand with which soccer players SPai the tablet 2 is paired at that moment, based on the names and face photographs.

When all the actual participant user pairing information RPJi (see FIG. 17(b)) is displayed, the actual participant user registration completion button (not illustrated) is selected.

The communication terminal-side user list creation unit 224 outputs actual participant user communication preparatory registration completion information REJi (see FIG. 17(c)) representing completion of communication preparatory registration of actual participant users to the moving body information transmission and reception unit 225.

[Moving Body Information Transmission and Reception Unit 225]

When receiving the actual participant user communication preparatory registration completion information REJi (see FIG. 17(c)) from the communication terminal-side user list creation unit 224, the moving body information transmission and reception unit 225 temporarily stores the same. The moving body information transmission and reception unit 225 determines whether a moving body information acquisition button MGf illustrated in FIG. 16 is selected (whether the tablet 2 is in a moving body information acquisition mode or not).

When the moving body information acquisition button MGf is selected, the moving body information transmission and reception unit 225 determines whether the actual participant user communication preparatory registration completion information REJi (see FIG. 17(c)), which represents completion of the preparation for communication with wearable devices 1 of all the soccer players SPai actually participating in the game, is inputted from the communication terminal-side user list creation unit 224.

Specifically, the moving body information transmission and reception unit 225 determines whether all the soccer players SPai actually participating in the game are paired and the wearable device IDs of the wearable devices 1 worn by the soccer players SPai, names, face photographs, and the like are created in the actual participant user pairing information memory 242.

When the actual participant user communication preparatory registration completion information REJi (see FIG. 17(c)) is inputted, the moving body information transmission and reception unit 225 may read camera images CGi from the analysis result providing apparatus 3 and perform a process to display the camera images CGi on the screen of the tablet 2. To acquire the camera images CGi, a camera image display button (not illustrated) is displayed on the screen to be selected, for example.

Upon selection, the moving body information transmission and reception unit 225 reads the place name (place code: soccer field name) or group name (group code) included in the actual participant user communication preparatory registration completion information REJi (see FIG. 17(c)).

The moving body information transmission and reception unit 225 adds date, time, and the like to the read data to create camera image specifying information CPJi (the tablet ID, soccer field, group name, . . . ) and transmits the same to the analysis result providing apparatus 3 through the Internet network N.

The moving body information transmission and reception unit 225 then receives thumbnail images of the soccer field Ai corresponding to the camera image specifying information CPJi, from the analysis result providing apparatus 3 and outputs the same to a not-illustrated screen (browser) for display. Each thumbnail image is preferably accompanied with a camera number or camera ID.

The moving body information transmission and reception unit 225 transmits camera image selection information CSJi (the selected camera number, date, and time), which is composed of the camera number, tablet ID, date, time, and the like of the selected thumbnail images, to the analysis result providing apparatus 3 through the Internet network N.

The camera images CGi corresponding to the camera image selection information CSJi are sequentially displayed in the camera image window on the screen.

Upon receiving the actual participant user communication preparatory registration completion information REJi (see FIG. 17(c)) from the communication terminal-side user list creation unit 224, the moving body information transmission and reception unit 225 determines whether basic moving body information analysis request input information KBJi (see FIG. 20) is stored in the moving body information memory 243. The moving body information analysis request input information KBJi is information that specifies from which soccer players to request the moving body information DSJi (see FIG. 12), by which time (time range Wti) to request the moving body information DSJi, and how to display the same.

When the moving body information memory 243 does not store the moving body information analysis request input information KBJi (see FIG. 20), the moving body information transmission and reception unit 225 displays a moving body information request input screen KBGc illustrated in FIG. 19, on the screen.

The moving body information request input screen KBGc includes the group name (team name), input fields for names (wearable device IDs), and input fields for the time range Wti (Wtop to Wtri), sensor acquisition type Ki (all or select), position display type Gki, image type (camera or simulated image), and the like. The name fields are provided for about three players by way of example.

The moving body information transmission and reception unit 225 creates the moving body information analysis request input information KBJi by setting all the wearable device IDs inputted in the moving body information request input screen KBGc, in a wearable device ID section.

Upon selection of a not-illustrated OK button, the moving body information transmission and reception unit 225 transmits to the analysis result providing apparatus 3 through the Internet network N, each set of information inputted in the moving body information request input screen KBGc as the moving body information analysis request input information KBJi (see FIG. 20) for storage in a later-described storage server 322 (as the history). The moving body information transmission and reception unit 225 also stores the same in the moving body information memory 243.

The moving body information transmission and reception unit 225 creates the transmission pattern PTi (see FIG. 21) to cause the wearable device 1 to create a transmission format including the number of regions (for sensor data) corresponding to the sensor acquisition type ki included in the moving body information analysis request input information KBJi (see FIG. 20) and regions in which the detection position Pi, system time STi, and the like are to be written.

T the transmission pattern PTi, a command to write the acquired sensor data in numerals (a numerical string) is added. This prevents redundant things from being transmitted from the wearable device 1 side to shorten the communication time, thus improving the real time performance.

The moving body information transmission and reception unit 225 creates the moving body information request information YDJi (see FIG. 13), which is a set of information including the wearable device ID section, sensor acquisition type ki (all or select), tablet ID, and the like, only during the time range Wti included in the moving body information analysis request input information KBJi (see FIG. 20).

The created moving body information request information YDJi is transmitted with the communication initial connection setting unit 223 via the Bluetooth (registered trademark) protocol to each wearable device 1 at the same time. The transmission pattern PTi is simultaneously transmitted to the wearable device 1.

Each time the moving body information DSJi (see FIG. 12) corresponding to the moving body information request information YDJi from the communication initial connection setting unit 223 is inputted from the wearable devices 1, the moving body information transmission and reception unit 225 accepts the inputted moving body information DSJi and transmits the same to the analysis result providing apparatus 3 through the Internet network N.

The transmission of the moving body information request information YDJi and moving body information DSJi continues until the communication link is disconnected.

[Analysis Result Display Processing Unit 226]

The analysis result display processing unit 226 transmits the information inputted in the moving body information request input screen KBGc as the moving body information analysis request input information KBJi (see FIG. 20), that requests the kinds of sensor data SDi to be analyzed and how long (the time range Wti) to analyze the sensor data SDi, to the analysis result providing apparatus 3 via the Internet protocol.

The analysis result display processing unit 226 then waits for the display control data PKJi (see FIG. 14) used to display on the screen, the detection position Pi and moving body information DSJi (moving body information, see FIG. 12) of the soccer player SPai (described later) in the soccer field Ai from the analysis result providing apparatus 3.

Figure 22:
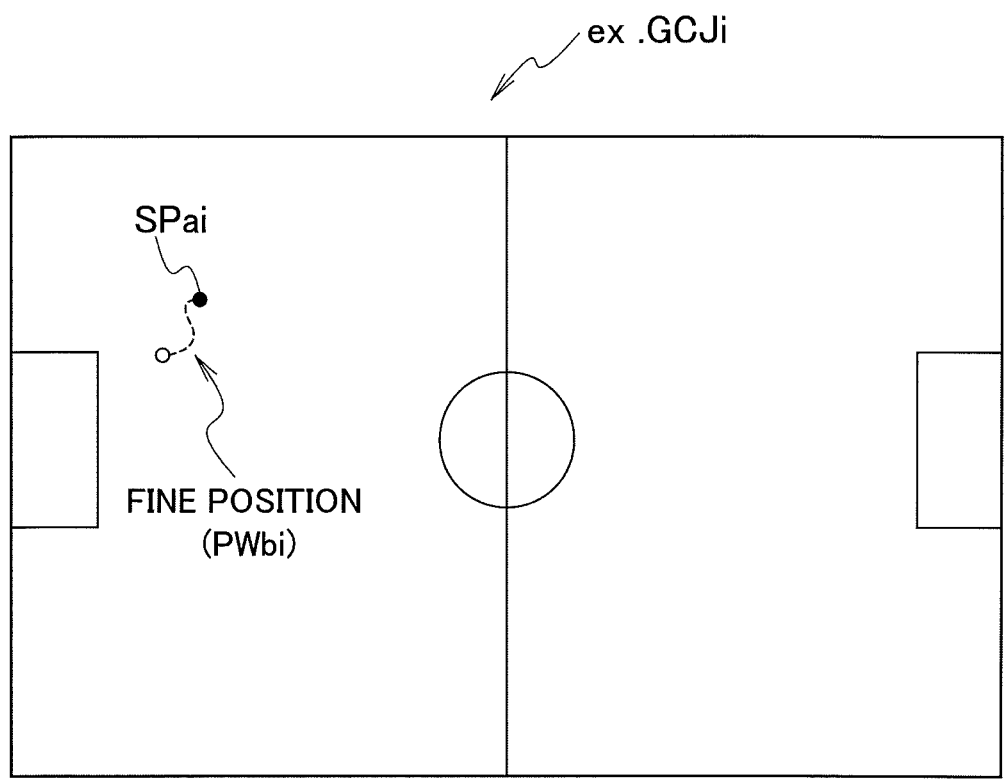
FIG. 22 is a diagram illustrating a display example of fine position.

Each time receiving the display control data PKJi, the analysis result display processing unit 226 stores the display control data PKJi in the analysis result reception memory 246 of the tablet-side storage unit 24 and outputs the same to the browser for screen display (see FIG. 22).

[Wearable Device 1]

Figure 23:
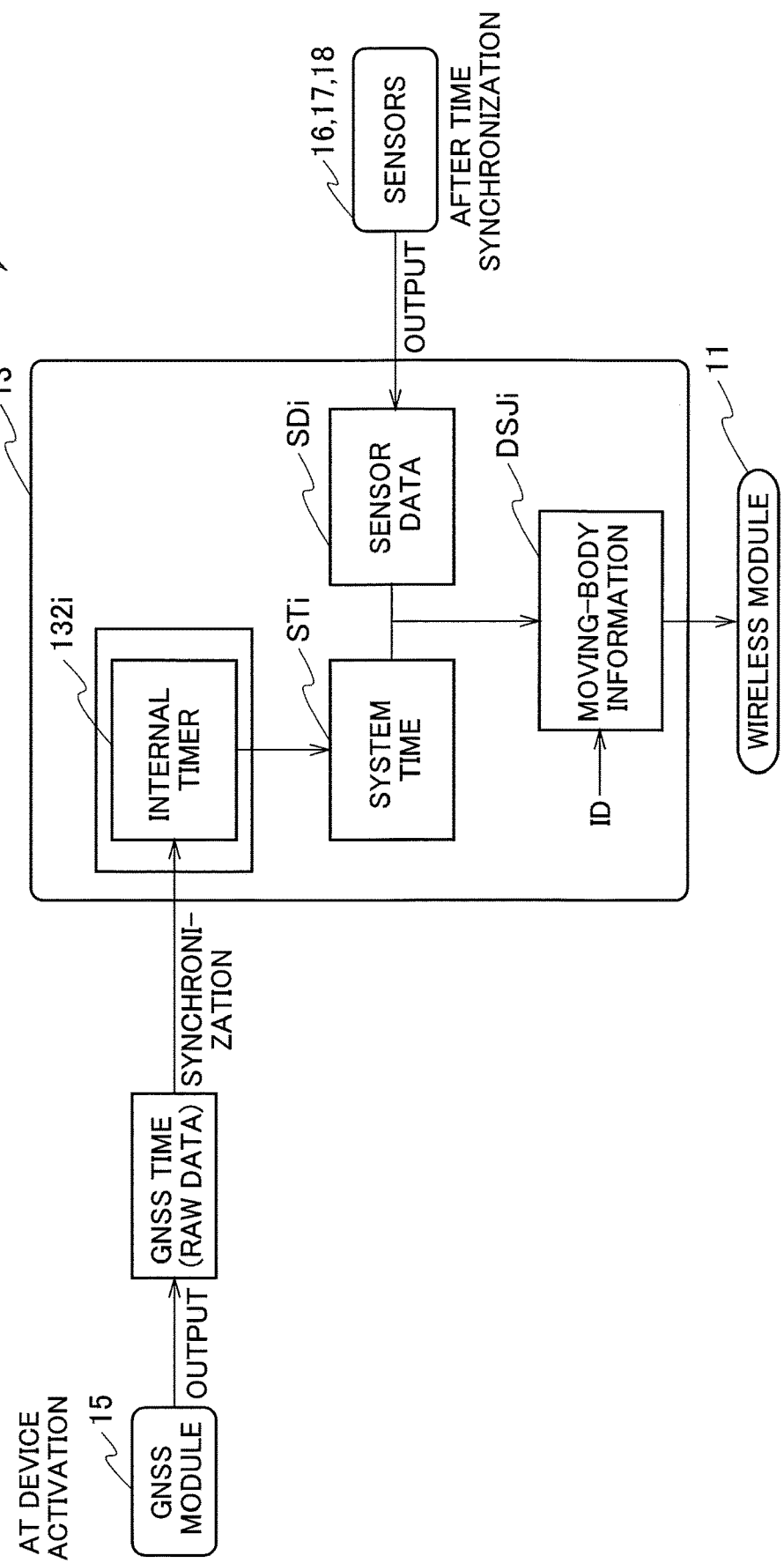
FIG. 23 is a block diagram illustrating an idea of the operation of the wearable device.

Prior to description of the specific configuration of the wearable device 1, first, the idea of the operation of the wearable device 1 is described using FIG. 23. In the following description, it is assumed that the initial time setting is already finished by the tablet 2.

As illustrated in FIG. 23, for example, when a wearable device 1 is activated, the wearable device 1 performs synchronization between the GNSS time (Raw data) of the position sensor 15 as a GNSS module and the system time STi of the internal timer 132i (which may be a program timer) of the controller 132 (microcomputer) in the main control module 13 of the wearable device 1.

After the synchronization, the wearable device 1 reads sensing results (sensor data SDi) from the biometric information detection sensor 16, environment information detection sensor 17, moving body state information detection sensor 18.

The biometric information detection sensor 16, environment information detection sensor 17, moving body state information detection sensor 18 output sensor data SDi at different times specific to the sensor type.

The main control module 13 reads the sensor data SDi of the biometric information detection sensor 16, environment information detection sensor 17, moving body state information detection sensor 18 every system time STi.

Upon receiving the moving body information request information YDJi from the tablet 2, the main control module 13 reads the sensor types included in the moving body information request information YDJi. The main control module 13 reads a set of the system time STi (including the position information) and sensor data SDi (biometric or 9-axis sensor information) corresponding to the sensor types collected by that moment and allocates the same in the same format configuration as the transmission pattern PTi simultaneously transmitted with the moving body information request information YDJi. The set of the system time STi and sensor data SDi is transmitted as the moving body information DSJi from the wireless module 11.

When 1 PPS signal is outputted from the GNSS module in this process, the position is calculated using Raw data synchronized with the 1 PPS signal. The calculated position is called the detection position Pi or position data.

The wearable device 1 thus performs initial time setting with the time of the moving body information analysis apparatus 30 and creates as moving body information (hereinafter, referred to as the moving body information DSJi), the system time STi synchronized with the Raw data of the GNSS data, as the base of position detection, or a set of the system time STi, Raw data, and position data. The wearable device 1 then transmits the created moving body information to the tablet 2. The specific example of the wearable device 1 is described later using FIGS. 39 and 40.

[Analysis Result Providing Apparatus 3]

Figure 24:
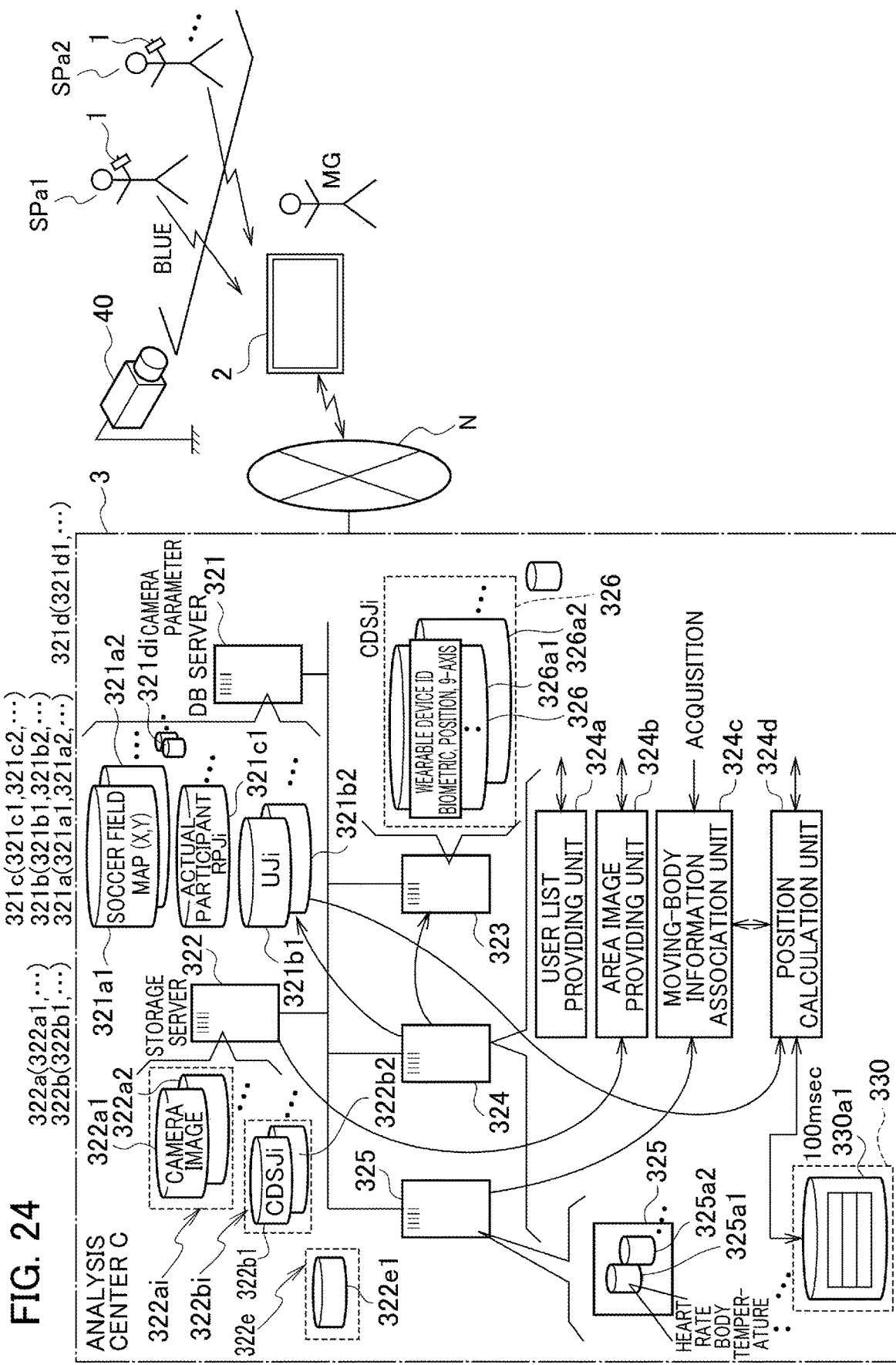
FIG. 24 is a schematic configuration diagram illustrating a specific example of an analysis result providing apparatus.

FIG. 24 is a schematic configuration diagram of the analysis result providing apparatus 3. The analysis result providing apparatus 3 is preferably composed of plural servers as illustrated in FIG. 24.

These servers include a DB server 321, the storage server 322, a moving body information reception server 323, a moving body position-related information creation server 324, and the like.

The storage server 322 stores camera images CGi, simulated images (illustrations) of the soccer field Ai, moving body information DSJi, and the like.

[[DB Sever 321]]

The DB server 321 includes a soccer field map memory unit 321a (area diagram storage units 321a1, 321a2, ...) storing a soccer field map AHi (defined by plane rectangular coordinates) as an area diagram; a user basic registration information memory unit 321b (321b1, 321b2, ...) storing the user basic registration information UJi (see FIGS. 18(a) and 18(b)) from the tablet 2; a center-side actual participant user memory unit 321c storing the actual participant user pairing information RPJi (see FIG. 17(b)) from the tablet 2 for history management; and the like. Hereinafter, a description is given of a process to register various information in each memory section.

[[Soccer Field Map Memory Unit 321a]]

When receiving group name (group code), soccer field code, and soccer field map AHi inputted by a person in authority, the DB server 321 stores in the soccer field map memory units 321a (321a1, 321a2, . . . ), the soccer field map AHi in association with the group name (group code) and soccer field code.

The memory regions in which the succor field map AHi is stored on a group name (group code) basis and on a soccer-field code basis are referred to as soccer field map memories 321ai (321a1, 321a2, . . . ).

[[User Basic Registration Information Memory Unit 321b]]

The DB server 321 receives the user basic registration information UJi (see FIGS. 18(a) and 18(b)) from a user list providing unit 324a of the moving body position-related information creation server 324. When the received user basic registration information UJi is already stored in the user basic registration information memory unit 321b, the DB server 321 notifies the tablet 2 that the user basic registration information UJi is already registered. When the received user basic registration information UJi is not registered, the DB server 321 creates and registers a user basic registration information memory 321bi (321b1, 321b2, . . . ) in the user basic registration information memory unit 321b by adding the group name, soccer field name, and the like included in the user basic registration information UJi.

The DB server 321 receives the tablet ID-included actual participant input information ZGJi from the user list providing unit 324a of the moving body position-related information creation server 324. The DB server 321 then determines whether the user basic registration information memory unit 321b includes the user basic registration information memory 321bi (321b1, 321b2, . . . ) storing the user basic information registration information UUJi (see FIG. 18(b)) of prospective game participants that includes the wearable devices ID included in the actual participant input information ZGJi. When the user basic registration information memory unit 321b does not include the user basic registration information memory unit 321bi of interest, the DB server 321 transmits an error to the tablet 2 through the user list providing unit 324a.

When the user basic registration information memory unit 321b includes the user basic registration information memory unit 321bi of interest, the DB server 321 adds the manager name, tablet ID, and the like included in user administrator basic registration information UMJi (see FIG. 18(a)) which is associated with the user basic information registration information UUJi of the game prospective participant stored in the user basic registration information memory unit 321bi (321b1, 321b2, . . . ). In this process, the date and time are preferably added.

The DB server 321 outputs to the user list providing unit 324a of the moving body position-related information creation server 324, the aforementioned information as the actual participant user-based basic information CDUJi (see FIG. 17(d); on a basis of users actually participating the game) representing the name (face photograph), wearable device ID, and the like of a soccer player SPai who actually participates in the game.

The DB server 321 registers the actual participant user-based basic information CDUJi in a game actual participant user-based memory region i (not illustrated) of the center-side actual participant user memory unit 321c for history management.

[[Center-Side Actual Participant User Memory Unit 321c]]

When receiving the actual participant user pairing information RPJi (see FIG. 17(b)) from the user list providing unit 324a of the moving body position-related information creation server 324, the DB server 321 determines whether the center-side actual participant user memory unit 321c includes the actual participant user memory 321ci (321c1, 321c2, . . . ) that includes the wearable device ID included in the received actual participant pairing information RPJi.

When the center-side actual participant user memory unit 321c does not include the actual participant user memory 321ci of interest, the DB server 321 creates an actual participant user memory 321ci with the wearable device ID of interest in the center-side actual participant user memory unit 321c and stores the received actual participant user pairing information RPJi (see FIG. 17(b)) in the same as the history.

[[Camera Parameter Memory Unit 321d]]

The DB server 321 stores camera parameters (γi) of the cameras 40 on a basis of the camera number, place name (soccer field name), and group name in camera parameter memories 321di (321d1, 321d2, . . . ) of a camera parameter memory unit 321d. These camera parameters are registered in advance by a person in authority of the analysis center C.

[[Storage Server 322]]

The storage server 322 includes: a camera image memory unit 322a storing the camera images CGi (the date, time, camera number, soccer field name, camera images CGi, date, time, . . . ) from the cameras 40 on a basis of the place name (soccer field name) and camera number; a center-side moving body information memory unit 322b storing the center-side moving body information CDSJi (see FIG. 12) on a wearable device ID (soccer field name or group name) basis; a time range and place-based analysis data copy memory unit 322e; and the like.

The memory regions generated in the camera image memory unit 322a on a basis of the soccer field name and camera number are referred to as camera image memories 322ai (322a1, 322a2, . . . ). Herein, the soccer field name may be ID.

The memory regions generated in the center-side moving body information memory unit 322b on a wearable device 1 basis are referred to as center-side moving body information memories 322bi (322b1, 322b2, . . . ).

The memory regions generated in the time range and place-based analysis data copy memory unit 322e on a basis of the wearable device 1, place name, and time range are referred to as time range and place-based analysis data copy memories 322ei (322e1, 322e2, . . . ).

Each time receiving a camera image CGi from the camera 40 (preferably an Internet camera), the storage server 322 determines whether the camera image memories 322ai including the camera number and the like of the received camera image CGi is not created in the camera image memory unit 322a. When the camera image memories 322ai of interest is not created, the storage server 322 creates a memory region of the camera image memory 322ai (322a1, 322a2, ... ) including the camera number and the like, in the camera image memory unit 322a.

When the camera image memories 322ai of interest is created, the storage server 322 stores the same in the camera image memory 322ai (322a1, 322a2, ... ) of the camera image memory unit 322a.

When receiving the camera image specifying information CPJi (the tablet ID, soccer field, group name, ... ) from the moving body information reception server 323, the storage server 322 transmits to the tablet 2, thumbnail images in the camera image memories 322ai (322a1, 322a2, ... ) corresponding to the received camera image specifying information CPJi (the tablet ID, soccer field, group name, ... ).

The storage server 322 receives the camera image selection information CSJi (the camera number, date, and time of the selected thumbnail image) from the tablet 2 and transmits the camera image CGi corresponding to the camera image selection information CSJi to the tablet 2.

Each time receiving the center-side moving body information CDSJi (see FIG. 12) from the moving body information reception server 323, the storage server 322 determines whether the center-side moving body information memory 322bi (322b1, 322b2, ... ) of the center-side moving body information memory unit 322b including the wearable device ID and the like of the received center-side moving body information CDSJi is created.

When the center-side moving body information memory 322bi of interest is not created, the storage server 322 creates a center-side moving body information memory 322bi (322b1, 322b2, ... ) in the center-side moving body information memory unit 322b in association with the wearable device ID and the like of the center-side moving body information CDSJi. When the center-side moving body information memory 322bi of interest is created, the storage server 322 stores the center-side moving body information CDSJi in the center-side moving body information memory 322bi (322b1, 322b2, ... ).

The storage server 322 stores later-described moving body information analysis result information KDJi from a moving body information analysis server 325 in a time range and place-based analysis data copy memory unit 322e (322e1, 322e2, ... ) on a wearable device ID basis.

The memory regions on a wearable device 1 basis are referred to as time range and place-based analysis data copy memories 322ei (322e1, 322e2, ... ).

[[Moving Body Information Reception Server 323]]

When receiving the camera image specifying information CPJi (the tablet ID, soccer field, group name, ... ) from the tablet 2, the moving body information reception server 323 outputs the received camera image specifying information CPJi to the storage server 322.

The moving body information reception server 323 receives the camera image selection information CSJi (the selected camera number, date, and time) from the tablet 2 and transmits the camera image selection information CSJi to the moving body position-related information creation server 324.

Each time receiving the moving body information DSJi (see FIG. 12) from the tablet 2 through the Internet network N, the moving body information reception server 323 determines whether the memory region (hereinafter, referred to as a moving body information memory 326ai (326a1, 326a2, ... ) including the wearable device ID of interest is created in a moving body information memory unit 326a. When the moving body information memory 326ai of interest is not created, the moving body information reception server 323 creates a moving body information memory 326ai (326a1, 326a2, ... ).

The moving body information DSJi (see FIG. 12) is information in which the regions according to the transmission pattern PTi (see FIG. 21) store the corresponding data.

The moving body information reception server 323 reads the detection position Pi included in the moving body information DSJi and converts the detection position Pi based on a plane rectangular coordinate conversion parameter βi stored in advance (map position GPi). The moving body information reception server 323 stores the map position GPi as the center-side moving body information CDSJi (see FIG. 12) in the corresponding moving body information memory 326ai (326a1, 326a2, ... ) of the moving body information memory unit 326a. The moving body information reception server 323 outputs the center-side moving body information CDSJi to the storage server 322 for storage as the history.

Each time receiving the moving body information analysis request input information KBJi (see FIG. 20) from the tablet 2, the moving body information reception server 323 transmits the received moving body information analysis request input information KBJi to a later-described moving body position-related information creation server 324 and moving body information analysis server 325.

Each time receiving disconnection information (with the wearable device ID) from the tablet 2 through the Internet network N, the moving body information reception server 323 clears the moving body information memory 326ai including the wearable device ID included in the received disconnection information.

[[Moving Body Position-Related Information Creation Server 324]]

The moving body position-related information creation server 324 includes a user list providing unit 324a, an area image providing unit 324b, a moving body information association unit 324c, a position calculation unit 324d, and the like.

<<User List Providing Unit 324a>>

The user list providing unit 324a receives the user basic registration information UJi (see FIGS. 18(a) and 18(b)) from the tablet 2 through the Internet network N. The user list providing unit 324a outputs the received user basic registration information UJi to the DB server 321 for registration.

The user list providing unit 324a further receives the actual participant input information ZGJi (with the tablet ID; FIG. 17(a)) from the tablet 2. The user list providing unit 324a outputs the received actual participant input information ZGJi to the DB server 321. When the user list providing unit 324a receives the actual participant user basic information CDUJi (see FIG. 17(d)) corresponding to the actual participant input information ZGJi from the DB server 321, the user list providing unit 324a immediately transmits the same to the tablet 2.

The user list providing unit 324a receives the actual participant user pairing information RPJi (see FIG. 17(b)) from the tablet 2 and outputs the same to the DB server 321, for storage in the actual participant user memory 321ci of the center-side actual participant user memory unit 321c.

<<Area Image Providing Unit 324b>>

The area image providing unit 324b receives the camera image selection information CSJi (the selected camera number, date, time, and the like) from the moving body information reception server 323 and stores the same temporarily.

The area image providing unit 324b determines the image type of the moving body information analysis request input information KBJi (see FIG. 20) from the tablet 2 through the moving body information reception server 323. When the image type indicates camera type, the area image providing unit 324b outputs to the position calculation unit 324d, the camera number included in the received camera image selection information CSJi (the selected camera number, date, time, and the like), the address of a camera parameter memory 321di (321d1, 321d2, . . . ) of the camera parameter memory unit 321d that includes the camera parameter (γi) corresponding to the camera image selection information CSJi, and the like.

When the image type included in the moving body information analysis request input information KBJi (see FIG. 20) indicates simulated image type (including the soccer field code), the area image providing unit 324b outputs to the moving body information association unit 324c, the address of the soccer field map memory unit 321a (321a1, 321a2, . . . ) of the DB server 321 storing the corresponding soccer field map AHi. These addresses are collectively referred to as display area image-type storage address information.

<<Moving Body Information Association Unit 324c>>

Each time receiving the moving body information analysis result information KDJi from the moving body information analysis server 325, the moving body information association unit 324c stores the same temporarily.

Each time receiving wearable device ID-included fine position data information RDJi (RDJ1, RDJ2, . . . ; see FIG. 25) from the position calculation unit 324d, the moving body information association unit 324c stores the same temporarily. The moving body information association unit 324c temporarily stores the center-side moving body information CDSJi (see FIG. 12) from the moving body information reception server 323.

When the wearable device ID included in the moving body information analysis result information KDJi matches wearable device ID included in the fine position data information RDJi (the wearable device ID, fine position, system time STi, 9-axis sensor information eJi, . . . ), the moving body information association unit 324c associates the fine position data information RDJi (RDJ1, RDJ2, . . . ) with the moving body information analysis result information KDJi (biometric information, analysis results, . . . ).

When the wearable device ID included in the center-side moving body information CDSJi matches these wearable device IDs, the moving body information association unit 324c associates the face photograph included in the center-side moving body information CDSJi and name code with the camera number from the area image providing unit 324b.

The moving body information association unit 324c reads a template for plural windows WUi registered in advance. The template is composed of plural windows WUi, for example (see FIG. 27). In a heart rate window WU2, an acceleration window WU3, and a posture window WU4, the horizontal axis is defined by the minimum unit (100 ms, for example) of the system time STi, for example.

The moving body information association unit 324c associates these window numbers with the sensor acquisition types ki (the heart rate, body temperature, . . . , 9-axis sensor).

The moving body information association unit 324c creates the display control data PKJi illustrated in FIG. 14 and transmits the same to the tablet 2.

Figure 26:
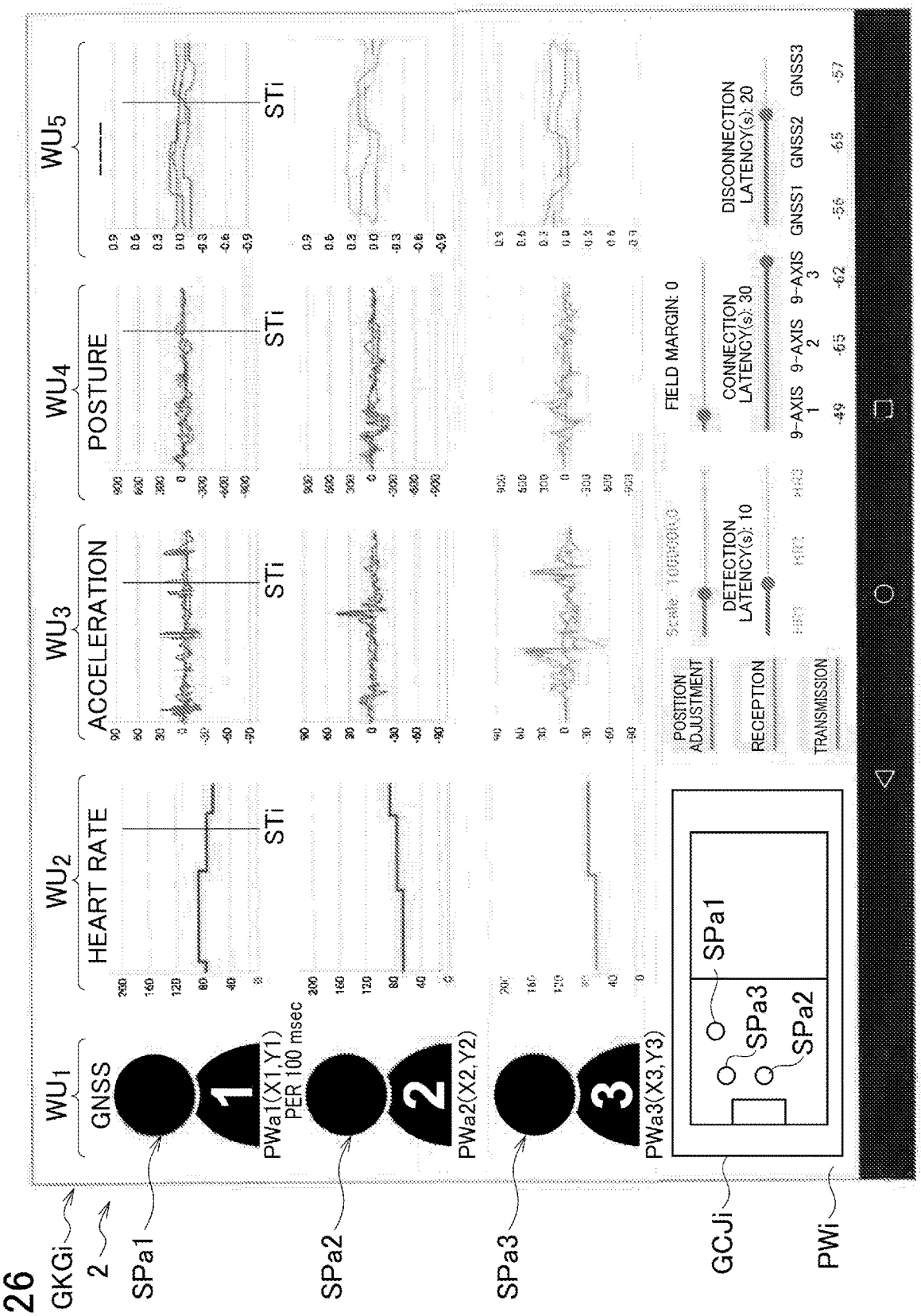
FIG. 26 is a diagram illustrating a display example of an analysis screen.

The screen of FIG. 26 is thereby displayed on the tablet 2, and fine positions PWbi illustrated in FIG. 22 are displayed in a real position display window RWi.

The manager MG therefore understands the current situation of a soccer player SPai and how the soccer player SPai is moving, in real time at a glance.

<<Position Calculation Unit 324d>>

The position calculation unit 324d performs a fine position data record creation process, a fine position calculation process, a display image fine position calculation process, and the like.

First, a description is given of each memory used by the position calculation unit 324d.

The position calculation unit 324d is connected to the position calculation data storage unit 330 and the like.

In the position calculation data storage unit 330, position calculation data memories 330ai (330a1, 330a2, . . . ) to store fine positions PWbi (Xi, Yi) and the like at the system time STi are created on a wearable device ID basis (see FIG. 25).

Specifically, in the position calculation data memory 330ai for each wearable device ID, as illustrated in FIG. 25, the same number of fine position data records RDi (RD1, RD2, . . . ) as the value obtained by dividing the duration by resolution di (100 ms, for example) of the system time STi, for example.

"Position Data Record Creation Process"

The position data record creation process reads the moving body information analysis request input information KBJi (see FIG. 20) from the tablet 2.

The position data record creation process determines whether the position calculation data memory 330ai (330a1, 330a2, . . . ) including the position display type Gki (Fine gdi, Normal gi) and wearable device ID included in the moving body information analysis request input information KBJi is created in the position calculation data storage unit 330. When the position calculation data memory 330ai (330a1, 330a2, . . . ) of interest is not created, the position data record creation process creates the same in the position calculation data storage unit 330.

When the position display type Gki included in the moving body information analysis request input information KBJi indicates "Fine", for example, the position data record creation process creates in the position calculation data storage unit 330, the position calculation data memory 330ai (330a1, 330a2, . . . ) including the same number of fine position data records RDi as a number kji. The number kji is a number of records obtained by dividing the time range Wti by the unit (100 ms, for example) of the system time STi (see FIG. 25).

As illustrated in FIG. 25, the fine position data records RDi is composed of a region that stores the system time STi, a region that stores the fine position PWbi (Xi, Yi), a region that stores the 9-axis sensor information eJi, and the like.

"Fine Position Calculation Process"

The fine position calculation process reads the center-side moving body information CDSJi (see FIG. 12) from the moving body information reception server 323 as the current center-side moving body information CDSJi.

The fine position calculation process reads the region that stores the position of the transmission pattern PTi constituting the current center-side moving body information CDSJi and determines whether the map position GPi (position data) exists in the region. This means that the fine position calculation process determines whether the current center-side moving body information CDSJi includes a map position GPi (position data).

In other words, the fine position calculation process determines whether the current moving body information DSJi includes a map position GPi (position data).

When any map position GPi (position data) is not included, the fine position calculation process reads the wearable device ID included in the current center-side moving body information CDSJi. The position data record creation process retrieves the position calculation data memory 330*ai* (330*a*1, 330*a*2, or . . . ) including the wearable device ID of interest from the position calculation data storage unit 330.

The position data record creation process retrieves one of the fine position data records RDi created in the position calculation data memory 330*ai* (330*a*1, 330*a*2, or . . . ) that stores the system time STi included in the current center-side moving body information CDSJi (see FIG. 25). The system time STi, fine position PWbi, 9-axis sensor information eJi, wearable device ID, and the like of the retrieved fine position data record RDi are collectively referred to as fine position data information RDJi.

The aforementioned retrieval may be intended for all of the fine position data records RDi that store the fine position data information RDJi including the same wearable device ID or only the fine position data record RDi of the latest system time STi.

The position data record creation process reads the fine position data information RDJi stored in the retrieved fine position data record RDi and the like as previous fine position data information RDJi.

The position data record creation process reads the system time STi included in the current fine position data information RDJi. The position data record creation process then calculates the position at the read current system time STi as the current fine position PWbi, based on the system time STi, fine position PWbi, 9-axis sensor information eJi, and the like of the previous center-side moving body information CDSJi.

The position data record creation process outputs the calculated current fine position PWbi and the 9-axis sensor information eJi, wearable device ID, system time STi included in the current fine position data information RDJi as the current fine position data information RDJi (the device ID, fine position 9-axis sensor information eJi, or . . . ), to the display image fine position calculation process.

In this process, the position data record creation process outputs the current fine position data information RDJi after the calculated fine position PWbi is updated to a fine position PWbi' by the later-described display image fine position calculation process.

The position data record creation process stores the fine positions PWbi and PWbi' in association with each other in the fine position data records RDi of the position calculation data memory 330*ai* (330*a*1, 330*a*2, or . . . ) (see FIG. 25).

The position data record creation process retrieves the fine position data record RDi corresponding to the system time STi included in the current fine position data information RDJi and stores the fine position data information RDJi in the retrieved fine position data record RDi as the previous fine position data information RDJi.

When the aforementioned 9-axis sensor information eJi is not included, the 9-axis sensor information eJi is calculated using a proper number of previous fine positions PWbi.

When the map position GPi (position data) is included in the current center-side moving body information CDSJi, the position data record creation process obtains the included map position GPi (position data) as the fine position PWbi and 9-axis sensor information eJi at the system time STi of the previous fine position data information (RDJi).

The position data record creation process associates the obtained fine position PWbi and 9-axis sensor information eJi with the system time STi and the like and obtains the same as the previous fine position data information RDJi.

The position data record creation process retrieves the fine position data record RDi in the position calculation data memory 330*ai* (330*a*1, 330*a*2, or . . . ) corresponding to the system time STi of the previous fine position data information RDJi and stores the obtained previous fine position data information RDJi in the retrieved record.

"Display Image Fine Position Calculation Process"

The display image fine position calculation process determines display area image-type storage address information (camera or simulated image) from the area image providing unit 324*b*.

When the display area image-type storage address information (camera or simulated image) indicates the address of the camera parameter memory 321*di* (321*d*1, 321*d*2, or . . . ) of the DB server 321, the display image fine position calculation process reads the camera parameter γi stored in the camera parameter memory 321*di* (321*d*1, 321*d*2, or . . . ).

The display image fine position calculation process uses the camera parameter γi to convert (to PWbi') the fine position PWbi included in the fine position data information RDJi (the device ID, fine position, 9-axis sensor information eJi, or . . . ) obtained from the fine process calculation process.

The display image fine position data creation process updates the fine position PWbi of the previous fine position data information RDJi of the fine position data record RDi in the position calculation data memory 330*ai* (330*a*1, 330*a*2, or . . . ) to the fine position PWbi' (see FIG. 25).

The display image fine position data creation process outputs the fine position data information RDJi (RDJ1, RDJ2, . . . ; with the wearable device ID) to the moving body information association unit 324*c*. The fine position PWbi is thereby displayed on the screen of the tablet 2 as illustrated in FIG. 23.

When the display area image-type address information (camera or simulated image) indicates the address of the soccer field map memory unit 321*a* (321*a*, 321*a*2, . . . ) of the DB server 321 that stores the soccer field map AHi, the display image fine position data creation process converts the fine position PWbi included in the fine position data information RDJi (the device ID, fine position, 9-axis sensor information eJi, or . . . ) from the fine position calculation process, based on the coordinate system of the soccer field map AHi. The fine position obtained by the conversion is set as the fine position PWbi' at the system time STi in the soccer field Ai.

The display image fine position data creation process then updates the fine position PWbi of the previous fine position data information RDJi of the fine position data record RDi in the position calculation data memory 330*ai* (330*a*1, 330*a*2, or . . . ) to the fine position PWbi'.

The display image fine position data creation process outputs the fine position data information RDJi (RDJ1, RDJ2, . . . ; with the wearable device ID) to the moving body information association unit 324*c*. The fine position PWbi is thereby displayed on the screen of the tablet 2 as illustrated in FIG. 23.

[Moving Body Information Analysis Server 325]

The moving body information analysis server 325 includes an analysis data memory unit 325*a* and analyses the moving body information. The moving body information analysis server 325 provides the analysis result to the tablet 2 through the moving body information association unit 324c of the moving body position-related information creation server 324.

In the analysis data memory unit 325a, analysis data memories 325ai (325a1, 325a2, . . . , 325ai, for example) are created in advance. For example, a heart rate analysis data memory 325a1, a body temperature analysis data memory 325a2, . . . , a 9-axis analysis data memory 325a3, and the like are created.

Figure 27:
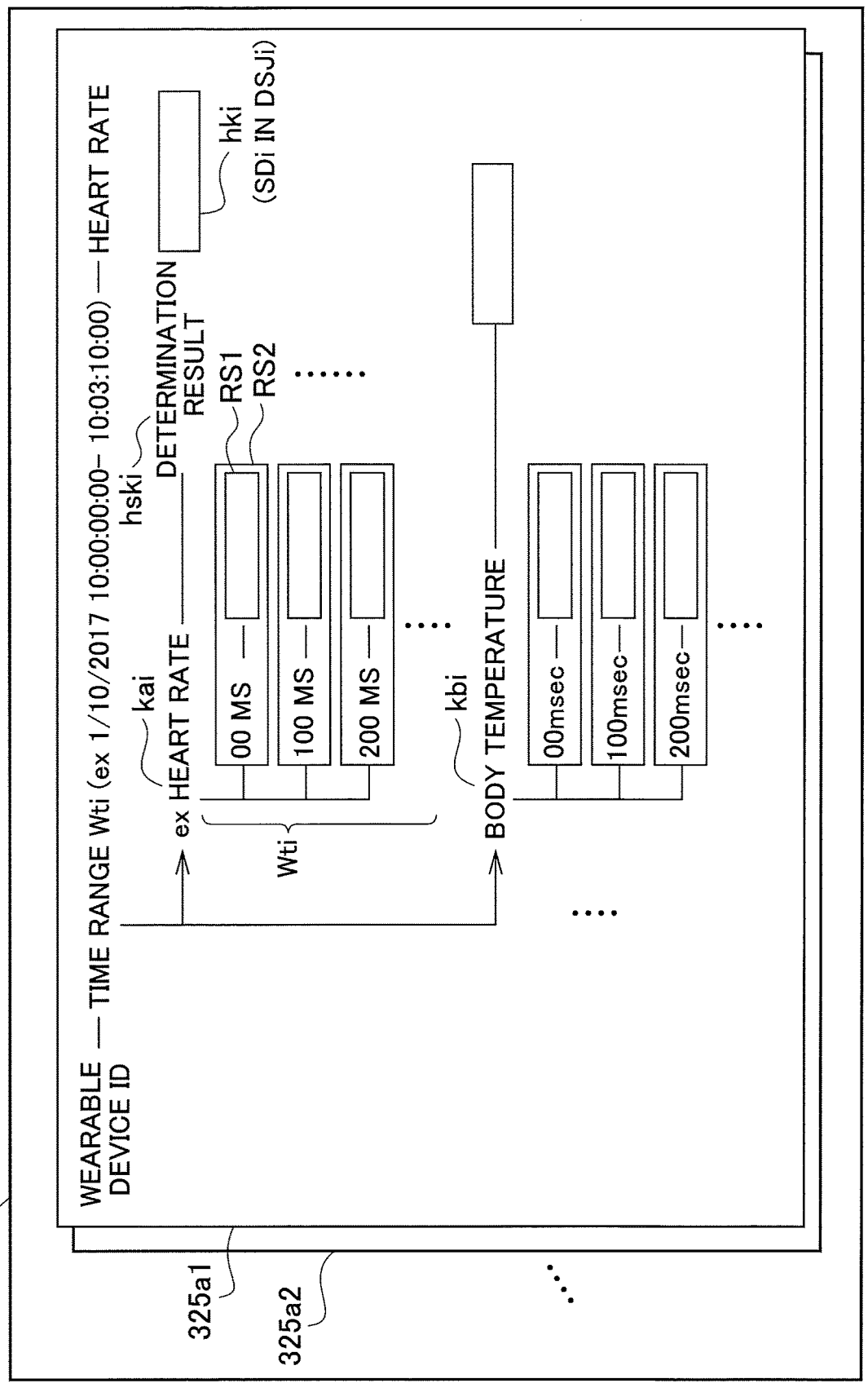
FIG. 27 is a schematic diagram illustrating a format configuration of a memory for analysis data.

The format configuration of those analysis data memories 325ai is as follows, as illustrated in FIG. 27: the wearable device ID and time range Wti are associated with the sensor acquisition type ki (heart rate (kai), body temperature (kbi), . . . ). In the sensor acquisition type ki, sensor data storage regions RSi (RS1, RS2, . . . ) that store sensor data SDi (heart rate, body temperature, . . . , 9-axis sensor) obtained at intervals of 100 ms, for example, are formatted.

In the sensor acquisition type ki, a determination result region hski that stores a determination result hki of the sensor data SDi at intervals of 100 ms stored in the sensor data storage region RSi is created.

Each time the moving body information analysis request input information KBJi is outputted from the moving body information reception server 323, the moving body information analysis server 325 creates in the analysis data memory unit 325a, the analysis data memory 325ai (325a1, 325a2, . . . , for example) including the wearable device ID and time range Wti included in the moving body information analysis request input information KBJi and the sensor acquisition types ki (heart rate (kai), body temperature (kbi), . . . ) and the like.

The moving body information analysis server 325 then retrieves all the center-side moving body information CDSJi (see FIG. 12) that satisfies the wearable device ID and sensor acquisition types ki (heart rate, body temperature, . . . , 9-axis sensor, or a combination thereof) included in the outputted moving body information analysis request input information KBJi and the time range Wti, from the center-side moving body information memory 322bi (322b1, 322b2, . . . ) in the center-side moving body information memory unit 322b of the storage server 322.

The moving body information analysis server 325 sequentially reads the sensor data SDi of all of the sensor acquisition types ki (heart rate, body temperature, . . . , 9-axis sensor, or a combination thereof) in the center-side moving body information CDSJi and stores the same in the corresponding sensor data storage regions RSi of the sensor acquisition types ki (heart rate, body temperature, . . . , 9-axis sensor, or a combination thereof).

The moving body information analysis server 325 outputs to the moving body information association unit 324c as the moving body information analysis result information KDJi, the wearable device ID, time range Wti, sensor acquisition types ki (heart rate, body temperature, . . . , 9-axis sensor, or a combination thereof), sensor data SDi stored in the sensor data storage region RSi in the time range Wti for each sensor acquisition type ki, and the determination result hki of the determination result region hski, and the like of the center-side moving body information memory 322bi (322b1, 322b2, . . . ). The moving body information analysis server 325 copies and stores the moving body information analysis result information KDJi in the time range and place-based analysis data copy memories 322ei (322e1, 322e2, . . . ). The moving body information analysis server 325 is therefore able to easily provide the past moving body information analysis result information KDJi.

(Overall Operation Description)

Figure 28:
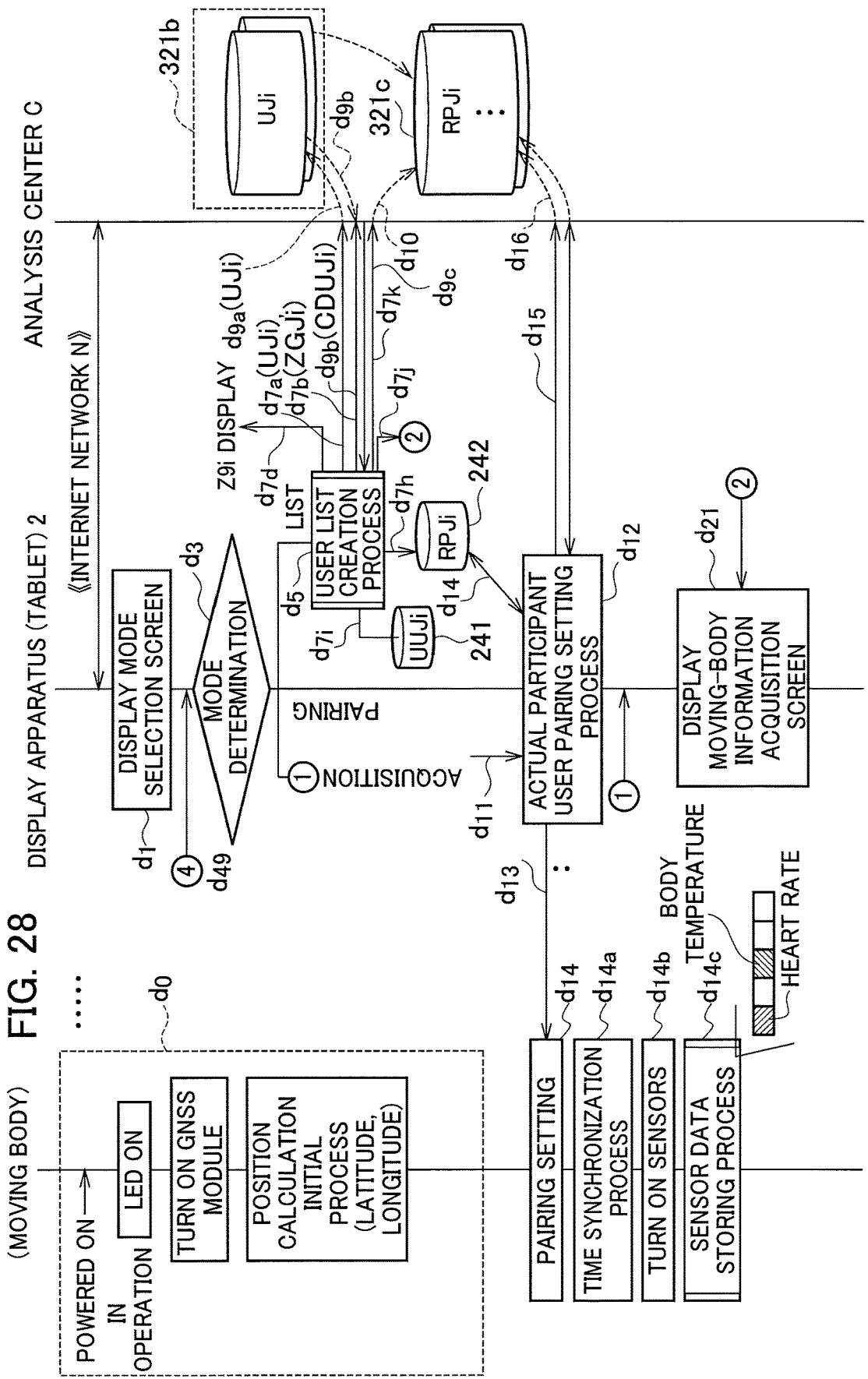
FIG. 28 is a sequence diagram (No. 1) illustrated to explain the overall operation of the moving body information providing system.
Figure 29:
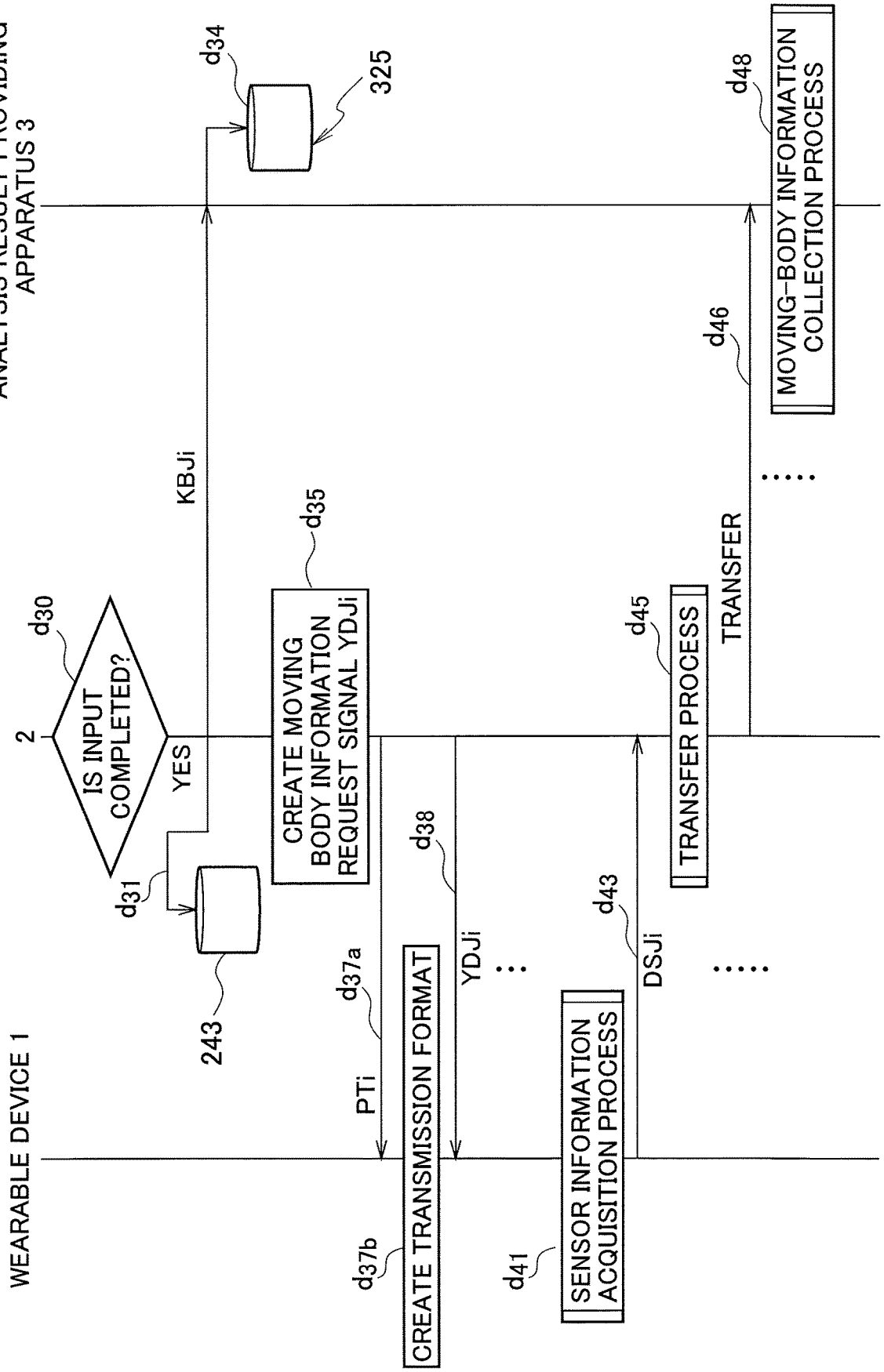
FIG. 29 is a sequence diagram (No. 2) illustrated to explain the overall operation of the moving body information providing system.
Figure 30:
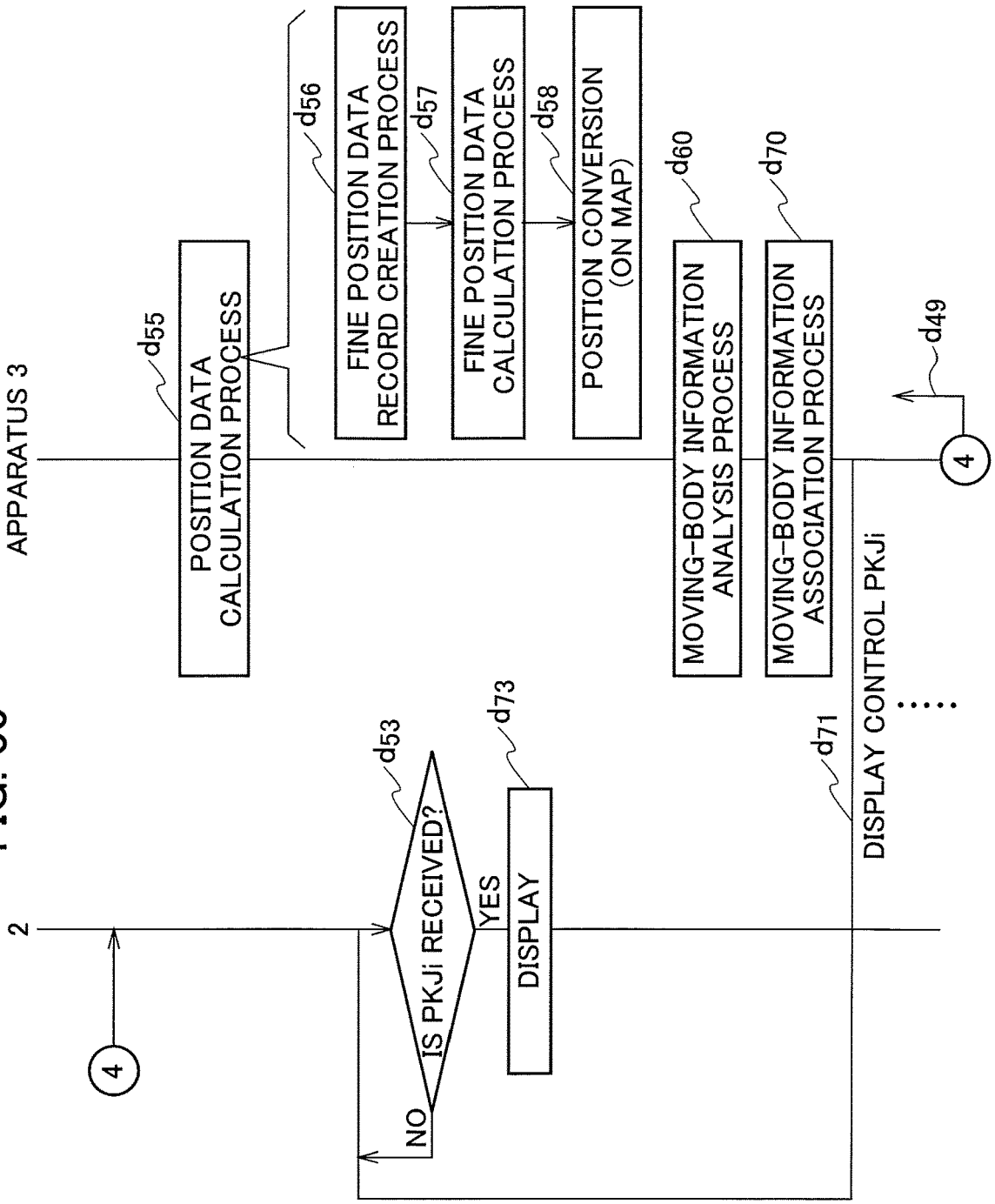
FIG. 30 is a sequence diagram (No. 3) illustrated to explain the overall operation of the moving body information providing system.

FIGS. 28 to 30 illustrate a sequence diagram to explain the overall operation of the moving body information providing system. In the description of Embodiment 2, it is assumed that a position-included moving body information providing tablet program (a collection and analysis tablet application) is already installed in the tablet 2.

In the description, it is assumed that camera images CGi are already displayed on the screen of the tablet 2.

As illustrated in FIG. 28, when the wearable device 1 is powered on, the position sensor 15 as a GNSS module is turned on to perform the position calculation initial process. In the wearable device 1, it is determined whether sensors that output data at different times have outputted sensor data SDi (digital data). When the sensors have outputted the sensor data SDi, the sensor data SDi (heart rate, body temperature, . . . , 9-axis sensor) are overwritten and stored in the sensor data storage region 131c (step d0).

In the tablet 2, when a position-included moving body information providing tablet icon (not illustrated) is selected by a manager MG or a person in authority, the position-included moving body information providing tablet program is activated to perform the following processes.

The mode determination unit 221 displays the mode selection screen MGi illustrated in FIG. 16 is displayed on the screen (d1).

As illustrated in FIG. 16, the mode selection screen MGi is composed of a user list registration button MGa, a communication initial connection setting button MGb, the actual participant registration button MGd, the moving body information acquisition button MGf, and the like.

When the communication initial connection setting button MGb is selected in the mode selection screen MGi, the communication initial connection setting unit 223 is activated. When the user list registration button MGa or actual participant registration button MGd is selected, the communication terminal-side user list creation unit 224 is activated.

When the moving body information acquisition button MGf (the moving body information acquisition mode) is selected, the moving body information transmission and reception unit 225 is activated.

The mode determination unit 221 determines the mode based on the button selected in the mode selection screen MGi (d3).

"Selection of User List Registration Button MGa"

When the user list registration button MGa is selected, the communication terminal-side user list creation unit 224 displays the user administrator basic information registration screen UMGi illustrated in FIG. 18(a) and the user basic information registration screen UUGi illustrated in FIG. 18(b) on the screen and executes the user list creation process (step d5).

The user administrator basic information registration screen UMGi illustrated in FIG. 18(a) includes group name (team name), group name code (team code), place name (location), company name, company code, administrator name (manager name), and the like.

The information inputted in the user administrator basic information registration screen UMGi is referred to as the user's administrator basic information registration information UMJi and is temporarily stored in the communication terminal-side user list memory 241 of the tablet-side storage unit 24.

The aforementioned user basic information registration screen UUGi includes group name (team name), name (name code), face photograph, age, height, weight, wearable device ID, . . . , and the like. The information inputted in the user basic information registration screen UUGi is referred to as the user basic information registration information UUJi (see FIG. 18(b)).

The communication terminal-side user list creation unit 224 temporarily stores the user basic information registration information UUJi (see FIG. 18(b)) in the communication terminal-side user list memory 241 of the tablet-side storage unit 24 (step d7i).

The communication terminal-side user list creation unit 224 adds the user basic information registration information UUJi, tablet ID, date and time of creation, and the like to the user administrator basic registration information UMJi (see FIG. 18(a)) in the communication terminal-side user list memory 241 and transmits the same to the analysis result providing apparatus 3 through the Internet network N as the aforementioned user basic registration information UJi (step d7a).

When receiving the user basic registration information UJi (see FIGS. 18(a) and 18(b)) from the tablet 2, the user list providing unit 324a of the analysis result providing apparatus 3 outputs the received user basic registration information UJi to the DB server 321, for registration in the user basic registration information memory unit 321b (step d9a).

"Selection of Actual Participant Registration Button MGd"

When the actual participant registration button MGd is selected in the mode selection screen MGi illustrated in FIG. 16, the communication terminal-side user list creation unit 224 of the tablet 2 displays the actual participant input screen ZGi illustrated in FIG. 17(a) (step d7d).

The actual participant input screen ZGi includes input fields for name, team name, place (soccer field), group name, date, time, and the like as illustrated in FIG. 17(a).

When an illustrated OK button MGg is selected, the tablet 2 transmits the information in the input fields of the actual participant input screen ZGi as the actual participant input information ZGJi to the analysis result providing apparatus 3 through the Internet network N (step d7b).

The user list providing unit 324a of the analysis result providing apparatus 3 receives the actual participant input information ZGJi from the tablet 2 and reads the user administrator basic registration information UMJi (see FIG. 18(a)) stored in the user basic registration information memory unit 321b of the DB server 321.

The user list providing unit 324a adds the manager name, tablet ID, face photograph, and the like included in the user administrator basic registration information UMJi and adds the date and time to create the actual participant user-based basic information CDUJi (see FIG. 17(d)) of the user who actually participates in the game. The user list providing unit 324a then stores the created actual participant user-based basic information CDUJi in the user basic registration information memory unit 321bi (321b1, 321b2, . . . ) of the DB server 321 as the history (d9b).

The user list providing unit 324a of the analysis result providing apparatus 3 transmits the actual participant user-based basic information CDUJi (see FIG. 17(d)) to the tablet 2 (d9c).

The communication terminal-side user list creation unit 224 of the tablet 2 receives the actual participant user-based basic information CDUJi (see FIG. 17(d)) and temporarily stores the actual participant user-based basic information CDUJi in a not-illustrated temporary storage memory. The tablet 2 then waits for pairing with the wearable device 1.

"Selection of Communication Initial Connection Setting Button MGb"The user of the tablet 2 selects the communication initial connection setting button MGb (step d11).

Upon selection, when the communication initial connection setting button MGb is selected, the communication initial connection setting unit 223 of the tablet 2 is activated and performs an actual participant user pairing setting process (steps d12, d13, and d14) to acquire the actual participant user pairing information RPJi (see FIG. 17(b)).

When activated, the communication initial connection setting unit 223 communicates with the analysis result providing apparatus 3 or a not-illustrated reference time service center to acquire the current time and sets the internal timer (not illustrated) to the current time. The communication initial connection setting unit 223 thus sets the initial time.

The communication initial connection setting unit 223 transmits pairing request information (the tablet ID, device type, maker, time, and the like) to several wearable devices 1, for example, for pairing with each wearable device 1. The communication initial connection setting unit 223 then acquires the pairing information PJi (see FIG. 13) and stores the same in a not-illustrated memory.

The communication initial connection setting unit 223 then waits for an output of the moving body information request information YDJi from the later-described moving body information transmission and reception unit 225.

In this process, each wearable device 1 uses a later-described initial time setting unit 132j of FIG. 38 to set a later-described internal timer 132i based on the time included in the pairing request information (the tablet ID, device type, maker, time, and the like) from the tablet 2. The initial time setting unit 132j of the wearable device 1 uses 1 PPS signal from the position sensor 15 as a GNSS module, Raw data including GNSS time, and system time STi (GNSS time>system time STi) to synchronize the initial time of the system time STi with the GNSS time (d14a).

The wearable device 1 turns on the sensors (d14b) and performs the process to store various sensor data in the memory at a certain time (d14c).

The above-described process allows the moving body information DSJi (see FIG. 12) to be acquired from the wearable device 1.

The communication terminal-side user list creation unit 224 of the tablet 2 reads the pairing information PJi (see FIG. 13) stored in the communication initial connection setting unit 223 and associates the pairing information PJi with the received actual participant user-based basic information CDUJi, thus storing the same in the actual participant user pairing information memory 242, as the aforementioned actual participant user pairing information RPJi (see FIG. 17(b)) of each user who is actually participating in the game at that moment (step d7h).

The communication terminal-side user list creation unit 224 reads the actual participant user pairing information memory 242 and displays the actual participant user pairing information RPJi on the screen (step d7d).

The user of the tablet 2 (the manager MG, for example) is able to understand with which soccer players SPai the tablet 2 is paired at that moment, based on the names and face photographs.

When all the actual participant user pairing information RPJi (see FIG. 17(b)) is displayed, the user of the tablet 2 selects an actual participant user registration completion button (not illustrated).

The communication terminal-side user list creation unit 224 notifies the moving body information transmission and reception unit 225 of the actual participant user communication preparatory registration completion information REJi (see FIG. 17(c)) representing completion of actual participant user communication preparatory registration (step d7j).

The tablet 2 displays a message representing completion of actual participant user communication preparatory registration on the screen, prompting selection of the moving body information acquisition button MGf (see FIG. 16).

The actual participant user communication preparatory registration completion information REJi includes all of the wearable device IDs of the actual participant user pairing information RPJi (see FIG. 17(b)) stored in the actual participant user pairing information memory 242.

The tablet 2 then transmits the actual participant user pairing information RPJi to the analysis result providing apparatus 3 for management (step d7k).

The user list providing unit 324a of the analysis result providing apparatus 3 receives the actual participant user pairing information RPJi (see FIG. 17(b)) from the tablet 2 and outputs the same to the DB server 321, for storage in the actual participant user memory 321ci of the center-side actual participant user memory unit 321c (step d10).

"Selection of Moving Body Information Acquisition Button MGf"

When the moving body information acquisition button MGf (see FIG. 16) is selected, the moving body information transmission and reception unit 225 of the tablet 2 is activated to display the moving body information request input screen KBGc illustrated in FIG. 19 on the screen (step d21).

"Selection of Moving Body Information Acquisition Button MGf"

When the moving body information acquisition button MGf is selected, the moving body information transmission and reception unit 225 of the tablet 2 determines whether the actual participant user communication preparatory registration completion information REJi (see FIG. 17(c)) from the communication terminal-side user list creation unit 224 is inputted.

When the actual participant user communication preparatory registration completion information REJi is inputted, the moving body information transmission and reception unit 225 determines whether the moving body information analysis request input information KBJi (see FIG. 20) is stored in the moving body information memory 243. The moving body information analysis request input information KBJi determines from which wearable device 1 to request the sensor data SDi, the kind of sensor data SDi, and by which time (the time range Wti) to request the sensor data SDi. The moving body information transmission and reception unit 225 determines whether the moving body information analysis request input information KBJi is inputted.

When the moving body information analysis request input information KBJi is not stored, the moving body information request input screen KBGc illustrated in FIG. 19 is displayed on the screen.

As illustrated in FIG. 19, the moving body information request input screen KBGc includes input fields for group name (team name), time range Wti, name (wearable device ID), sensor acquisition types ki (all or select), position display type Gki (Fine or Normal), image type (camera or simulated image), and the like.

The time range Wti indicates the time range in which the moving body information DSJi (see FIG. 12) acquired by the wearable device 1 is to be obtained. The input field for the time range Wti is composed of input fields for the start time Wtpi and end time Wtri.

In the input fields for the start time Wtpi and end time Wtri, the date and time are entered in the format of YY.MM.DD.HH.MM.SS in order to allow analyses of the position and the like on a 100 ms scale, for example. The name input field allows several persons' names to be entered.

The input field for the sensor acquisition type ki is composed of: an all selected field that specifies all of the sensors (the heart rate, body temperature, . . . , and 9-axis sensor) provided for the wearable device 1; and a selection input field that specifies desired sensors (the heart rate, body temperature, . . . , 9-axis sensor, or a combination thereof).

As illustrated in FIG. 29, the moving body information transmission and reception unit 225 determines whether the not-illustrated OK button is selected (step d30).

When the OK button is selected, the moving body information transmission and reception unit 225 stores each set of information inputted in the moving body information request input screen KBGc (see FIG. 19) as the moving body information analysis request input information KBJi (see FIG. 20) in the moving body information memory 243 (step d31).

The moving body information transmission and reception unit 225 transmits the moving body information analysis request input information KBJi (see FIG. 20) to the analysis result providing apparatus 3 through the Internet network N (step d32).

The moving body information analysis request input information KBJi includes the wearable device ID section, time range Wti, sensor acquisition type ki, and the like as illustrated in FIG. 20. The moving body information transmission and reception unit 225 creates the moving body information analysis request input information KBJi by setting all the wearable device IDs inputted in the moving body information request input screen KBGc (see FIG. 19), in the wearable device ID section.

The moving body information reception server 323 of the analysis result providing apparatus 3 receives the moving body information analysis request input information KBJi from the tablet 2 and transmits the received moving body information analysis request input information KBJi to the moving body position-related information creation server 324 and moving body information analysis server 325 (step d34).

The moving body information transmission and reception unit 225 creates the moving body information request information YDJi (see FIG. 13), which is a set of information of the wearable device ID section, sensor acquisition types ki (all or select), and tablet ID, only during the time range Wti included in the moving body information analysis request input information KBJi (see FIG. 20) (step d35).

The moving body information transmission and reception unit 225 creates the transmission pattern PTi (see FIG. 21) to form the transmission format KSRi including the regions of the sensors according to the sensor acquisition type ki included in the moving body information analysis request input information KBJi and regions in which the detection position Pi, system time STi, and the like are to be written.

The transmission pattern PTi is provided with a command to write acquired data in a numerical string. This prevents redundant things from being transmitted from the wearable device 1 side to shorten the communication time, thus improving the real time performance. The transmission pattern PTi includes the wearable device ID and tablet ID included in the moving body information analysis request input information KBJi. The transmission pattern PTi is transmitted to the wearable device 1 (step d37a).

Each time receiving the transmission pattern PTi from the tablet 2, the wearable device 1 forms a transmission format based on the received transmission pattern PTi in the storage unit 131 (step d37b).

The tablet 2 transmits the moving body information request information YDJi (see FIG. 13) to each wearable device 1 via the Bluetooth (registered trademark) protocol with the communication initial connection setting unit 223 (step d38).

Each time receiving the moving body information request information YDJi, the wearable device 1 performs the sensor information acquisition process to format the sensor data SDi (heart rate, body temperature, . . . , 9-axis sensor) and the like acquired by the sensors at that moment, on the transmission format KSRi to form digital data (the moving body information DSJi) (step d41).

The wearable device 1 transmits the acquired moving body information DSJi (see FIG. 12) to the tablet 2 via the Bluetooth (registered trademark) protocol (step d43).

On the other hand, the tablet 2 performs a transfer process to receive the moving body information DSJi from the wearable device 1 with the communication initial connection setting unit 223 and transmit the received moving body information DSJi to the analysis result providing apparatus 3 through the Internet network N via the Internet protocol (steps d45 and d46).

When the actual participant user pairing information RPJi (see FIG. 17(b)) that includes the wearable device ID included in the moving body information DSJi received from the wearable device 1 with the communication initial connection setting unit 223 of the tablet 2 is already registered in the actual participant user pairing information memory 242, the transfer process accepts the received moving body information DSJi (step d45).

The transfer process outputs the moving body information DSJi to the moving body information transmission and reception unit 225. Each time receiving the moving body information DSJi, the moving body information transmission and reception unit 225 transfers the moving body information DSJi to the analysis result providing apparatus 3 through the Internet network N via the Internet protocol (step S46).

Each time receiving the moving body information DSJi (see FIG. 12) from the tablet 2, the moving body information reception server 323 of the analysis result providing apparatus 3 performs a moving body information collection process to convert the detection position Pi included in the moving body information DSJi, based on the plane rectangular coordinate conversion parameter Pi (map position GPi) and use the map position GPi to create the center-side moving body information CDSJi (see FIG. 12) (step S48).

The center-side moving body information CDSJi (see FIG. 12) is stored in the corresponding moving body information memory 326ai (326a1, 326a2, . . . ) of the moving body information memory unit 326a.

The moving body information reception server 323 outputs the center-side moving body information CDSJi to the moving body position-related information creation server 324 and moving body information analysis server 325. The moving body information reception server 323 outputs the center-side moving body information CDSJi to the storage server 322 for storage as the history.

The tablet 2 then waits for the display control data PKJi from the analysis result providing apparatus 3 (step d53).

On the other hand, as illustrated in FIG. 30, when receiving the moving body information analysis request input information KBJi from the tablet 2, the position calculation unit 324d of the analysis result providing apparatus 3 performs the position data calculation process as illustrated in FIG. 30 (step d55).

The position data calculation process is performed by the position calculation unit 324d. As illustrated in FIG. 30, the position data calculation process includes a fine position data record creation process (step d56), a fine position calculation process (step d57), and a conversion process (position conversion process) to define a fine position on an area image (d58). These processes are described later using flowcharts.

In the analysis result providing apparatus 3, the moving body information analysis server 325 performs a later-described moving body information analysis process each time the moving body information analysis request input information KBJi (see FIG. 20) is outputted from the moving body information reception server 323 (step d60).

In the analysis result providing apparatus 3, the moving body information association unit 324c is activated to perform an association process that associates the wearable device ID, the sensor data SDi in the time range Wti for the sensor acquisition type ki (heart rate (kai), body temperature (kbi), . . . , 9-axis sensor, or a combination thereof), detection position Pi, and the like with the system time STi, thus creating the display control data PKJi illustrated in FIG. 14 (step d70).

The moving body information association unit 324c transmits the created display control data PKJi to the tablet 2 via the Internet protocol (step d71).

The moving body information association unit 324c may read the system time STi associated with the fine position PWbi of the fine position data record RDi in the moving body information analysis request input information KBJi, calculate the coordinate on the time axis of the acceleration graph, posture graph, or the like, that corresponds to the read system time STi, and create the display control data PKJi to display vertical axis bars Bi (Ba, Bb, Bc, . . . ) at the calculated coordinate.

Figure 36:
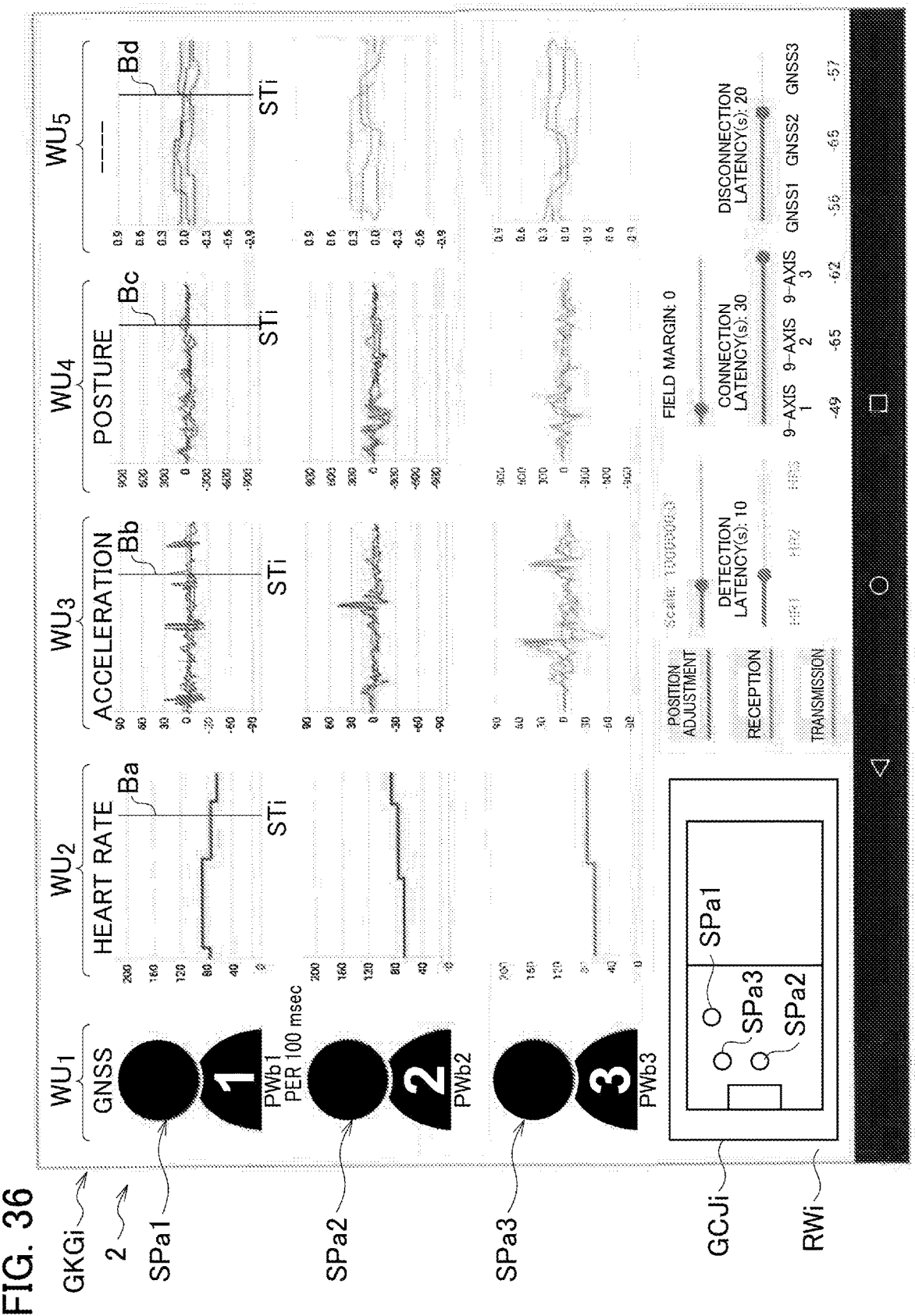
FIG. 36 is a diagram illustrating a display example of analysis results.

As illustrated in FIG. 36, the vertical axis bars Bi (Ba, Bb, Bc, . . . ) are thereby displayed corresponding to the time of the fine position PWbi in the acceleration graph, posture graph, and the like of the tablet 2. This allows for understanding of the situation, motion, and the like at the time of the fine position PWbi on a fine position scale.

The process proceeds to step d3 (step d49).

On the other hand, in the tablet 2, when determining that the display control data PKJi from the analysis result providing apparatus 3 is received in the aforementioned waiting mode (YES in step d53), the analysis result display processing unit 226 stores the display control data PKJi in the analysis result reception memory 246 of the tablet-side storage unit 24 and outputs the same to the browser for screen display (step d73).

Next, the processes of the moving body information reception server 323 and position calculation section 324d are described in detail using flowcharts.

[Process of Moving Body Information Reception Server 323]

Figure 31:
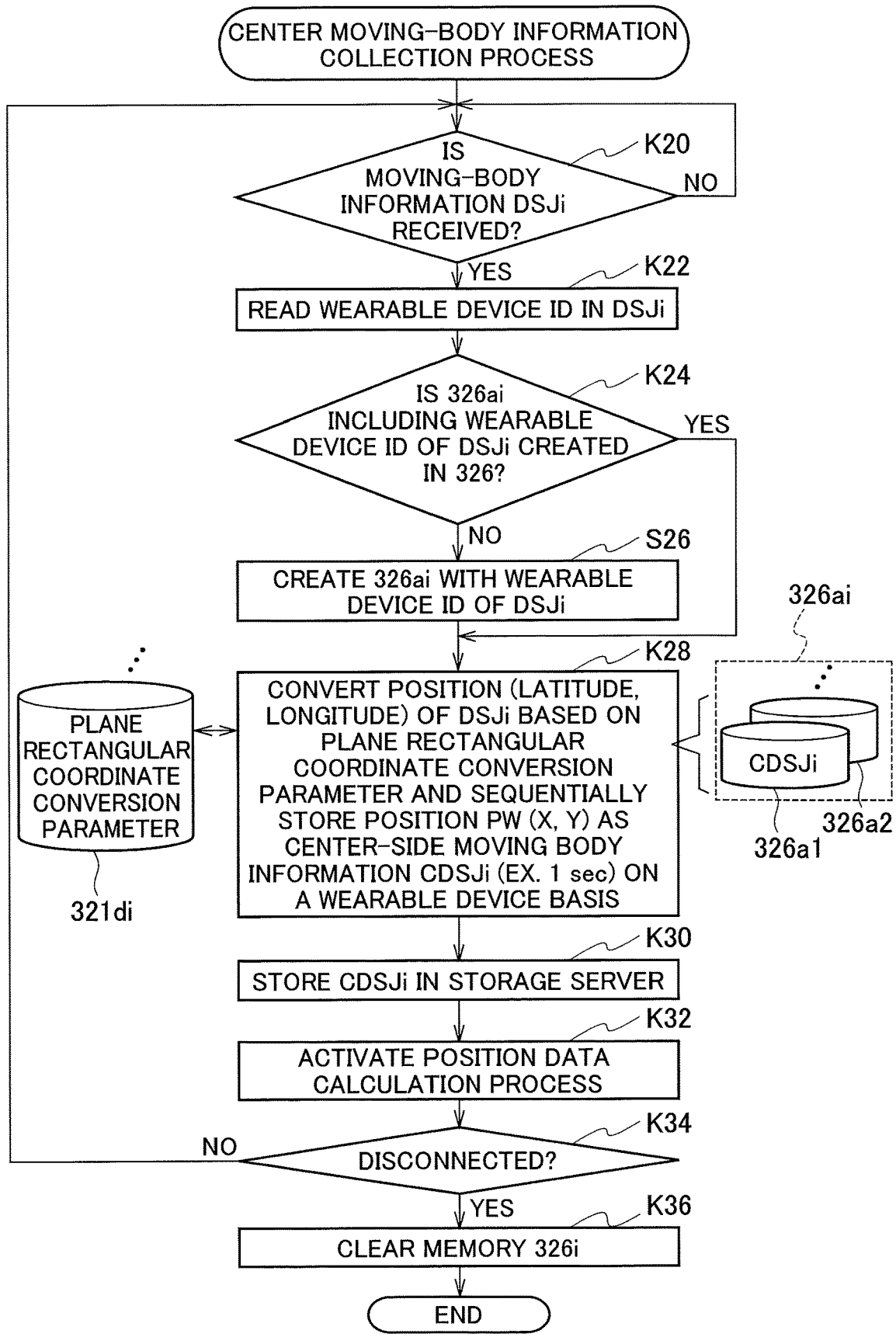
FIG. 31 is a flowchart illustrating processing of a moving body information reception server.

FIG. 31 is a flowchart illustrating the process by the moving body information reception server 323.

The moving body information reception server 323 determines whether the moving body information DSJi (see FIG. 12) transmitted from the tablet 2 through the Internet network N is received (step K20).

When the moving body information DSJi is received (YES in step K20), the moving body information reception server 323 reads the wearable device ID included in the received moving body information DSJi (step K22).

The moving body information reception server 323 determines whether the moving body information memory 326ai (326a1, 326a2, . . . ) including the wearable device ID is created in the moving body information memory unit 326a (step K24).

When determining that the moving body information memory 326ai (326a1, 326a2, . . . ) including the wearable device ID is not created in step K24 (NO), the moving body information memory 326ai (326a1, 326a2, . . . ) with the wearable device ID included in the moving body information DSJi is created in the moving body information memory unit 326a (step K26).

Next, the moving body information reception server 323 converts the detection position Pi included in the moving body information DSJi based on a plane rectangular coordinate conversion parameter βi stored in the camera parameter memory 321di of the DB server 321. The moving body information reception server 323 stores the same as the center-side moving body information CDSJi in the corresponding 326ai (326a1, 326a2, . . . ) (step K28).

The moving body information reception server 323 outputs the center-side moving body information CDSJi for storage (step K30).

Thereafter, in step K32, the moving body information reception server 323 activates the position data calculation process (described later in detail).

The moving body information reception server 323 determines whether disconnection information (including the wearable device ID) from the tablet 2 via the Internet network N (step K34).

When disconnection information is inputted (YES in step K34), the moving body information reception server 323 clears the moving body information memory 326ai that includes the wearable device ID included in the received disconnection information (step K36) and terminates the process.

When disconnection information (including the wearable device ID) is not inputted (NO in step K34), the moving body information reception server 323 returns the process to step K20.

When determining that the moving body information memory 326ai that includes the wearable device ID included in the moving body information DSJi (see FIG. 12) is created in step K24 (YES), the moving body information reception server 323 shifts the process to the step K28.

[Fine Position Data Record Creation Process of Position Calculation Unit 324d]

Figure 32:
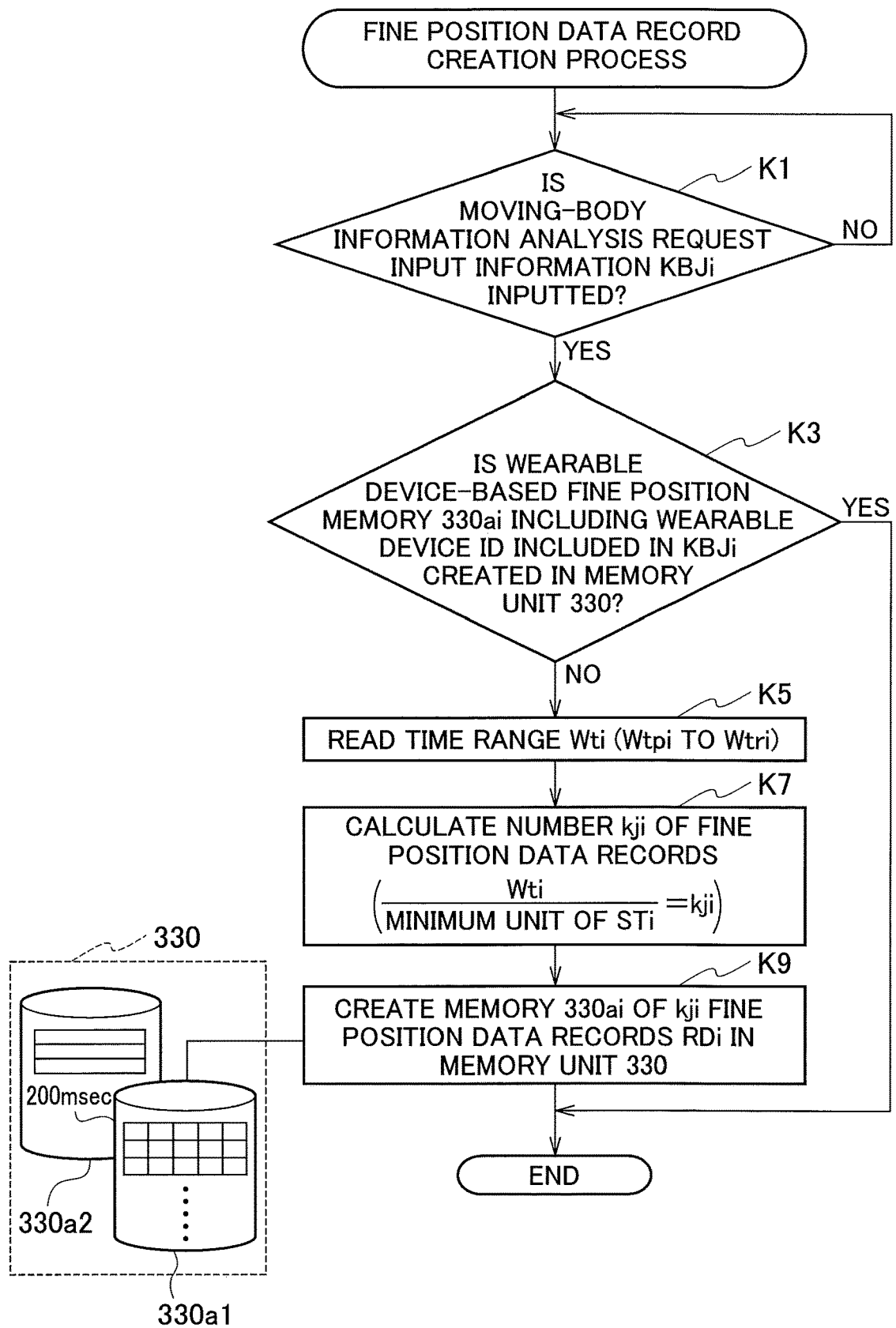
FIG. 32 is a flowchart illustrating a fine position data record creation process.

FIG. 32 is a flowchart illustrating the operation of the fine position data record creation process.

The fine position data record creation process determines whether the moving body information analysis request input information KBJi (see FIG. 20) from the tablet 2 is inputted as illustrated in FIG. 32 (step K1).

When determining that the moving body information analysis request input information KBJi is inputted (YES in step K1), The fine position data record creation process determines whether the position calculation data memory 330ai (330a1, 330a2, . . . ) including the position display type Gki and wearable device ID included in the moving body information analysis request input information KBJi is created in the position calculation data storage unit 330 (step K3).

When the position calculation data memory 330ai (330a1, 330a2, . . . ) is created (YES in step K3), the fine position data record creation process is terminated. When the position calculation data memory 330ai (330a1, 330a2, . . . ) is not created (NO in step K3), the fine position data record creation process reads the time range Wti (one minute, for example) included in the moving body information analysis request input information KBJi and a fine position resolution dKi (100 ms, for example) (step K5).

The fine position data record creation process divides the time range Wti by the fine position resolution dKi, which is an output interval of the system time STi, to calculate the number kji of fine position data records (step K7).

The fine position data record creation process creates the position calculation data memory 330ai including kji fine position data records RDi in the position calculation data storage unit 330 (step K9) and is terminated.

"Fine Position Calculation Process and Display Image Fine Position Calculation Process of Position Calculation Section 324d"

Figure 33:
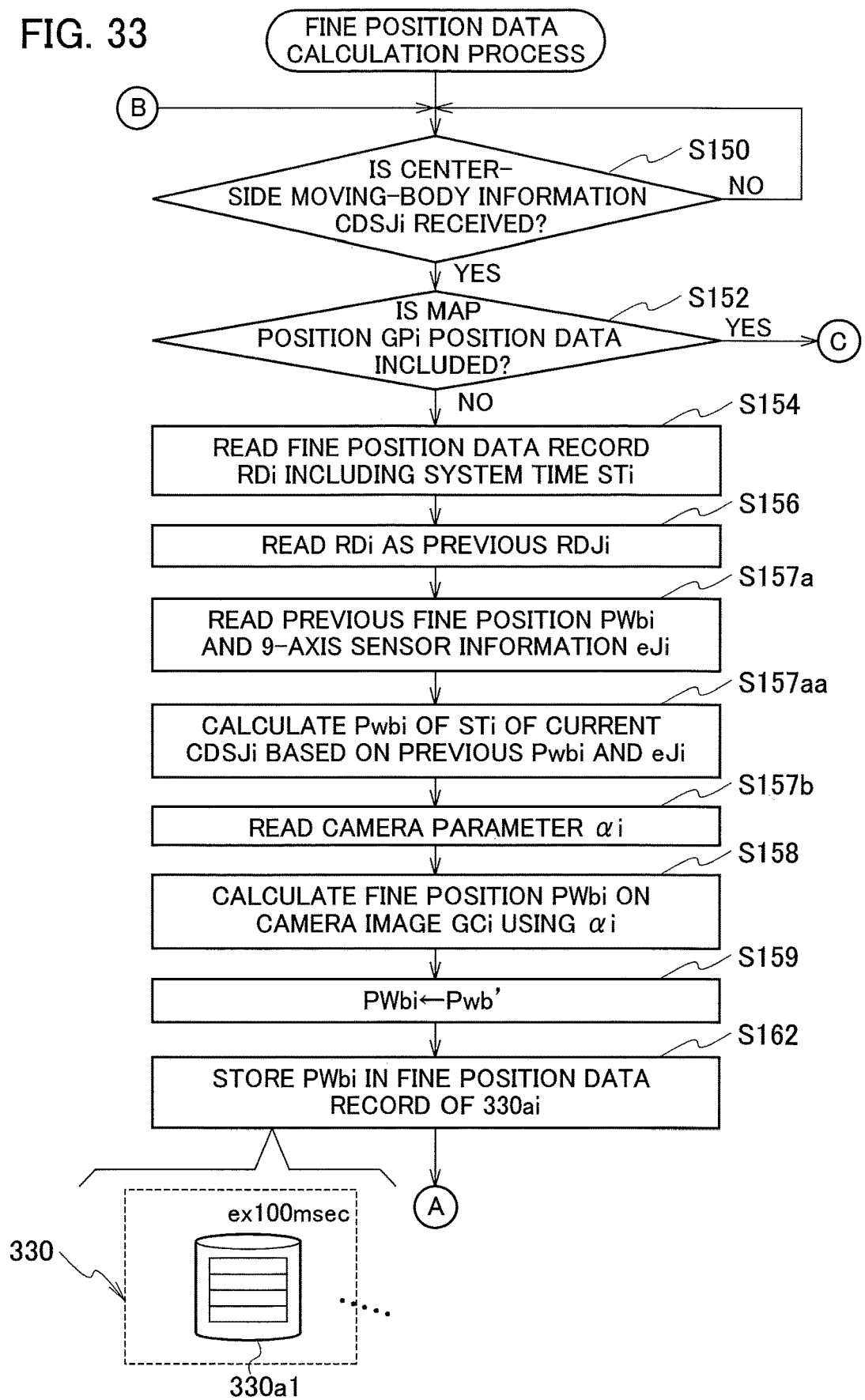
FIG. 33 is a flowchart (No. 1) illustrating a fine position calculation process.
Figure 34:
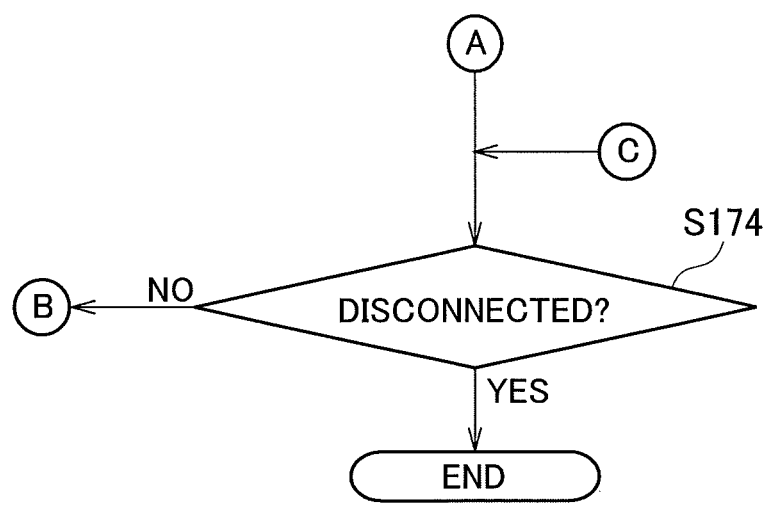
FIG. 34 is a flowchart (No. 2) illustrating the fine position calculation process.

FIGS. 33 and 34 are flowcharts illustrating the fine position calculation process and the display image fine position calculation process, respectively. In the following case, it is assumed that the center-side moving body information CDSJi does not include any map position GPi (position data). In addition, the type of images to be displayed is camera image type.

The fine position calculation process of the position calculation unit 324d determines whether the center-side moving body information CDSJi as the moving body information DSJi (see FIG. 12) transmitted from the tablet 2 through the Internet network N is received (step S150).

When the current center-side moving body information CDSJi is received, the fine position calculation process determines whether the center-side moving body information CDSJi includes the map position GPi (position data) (S152).

When determining that the center-side moving body information CDSJi does not include the map position GPi (position data), the fine position calculation process determines that the system time STi and system time STi are included.

When determining that the system time Sti is included, that is, determining that the map position GPi (position data) is not included, the fine position calculation process reads the wearable device ID included in the current center-side moving body information CDSJi and reads the fine position data record RDi including the wearable device ID and system time STi (S154).

Specifically, the fine position calculation process retrieves the position calculation data memories 330ai (330a1, 330a2, or . . . ) including the wearable device ID of interest from the position calculation data storage unit 330.

The fine position calculation process retrieves one of the fine position data records RDi created in the position calculation data memory 330ai (330a1, 330a2, or . . . ) that stores the system time STi included in the current center-side moving body information CDSJi.

The system time STi, fine position PWbi, 9-axis sensor information eJi, wearable device ID, and the like of the retrieved fine position data record RDi are collectively referred to as fine position data information RDJi.

The aforementioned retrieval may be intended for all of the fine position data records RDi that store the fine position data information RDJi including the same wearable device ID or only the fine position data record RDi of the latest system time STi.

The fine position calculation process reads the fine position data information RDJi and the like stored in the retrieved fine position data record RDi as the previous fine position data information RDJi (S156).

The fine position calculation process reads the system STi, fine position PWbi, and 9-axis sensor information eJi of the previous center-side moving body information CDSJi (S157a).

The fine position calculation process calculates the position at the current system time STi as the current fine position PWbi, based on the read information and the system time STi of the current fine position data information RDJi (S157aa).

The fine position calculation process outputs the calculated current fine position PWbi and the 9-axis sensor information eJi, wearable device ID, system time STi included in the current fine position data information RDJi, as the current fine position data information RDJi (the wearable device ID, fine position, 9-axis sensor information eJi, or . . . ), to the display image fine position calculation process.

The display image fine position calculation process reads the camera parameters γi stored in the camera parameter memory 321di (321d1, 321d2, or . . . ) of the DB server 321, based on the display area image-type storage address information from the area image providing unit 324b (S157b).

The display image fine position data calculation process uses the camera parameter γi to convert (to PWbi') the fine position PWbi included in the fine position data information RDJi (the wearable device ID, fine position, 9-axis sensor information eJi, or . . . ) from the fine process calculation process (S158).

The display image fine position data calculation process then updates the fine position PWbi of the previous fine position data information RDJi of the fine position data record RDi in the position calculation data memory 330ai (330a1, 330a2, or . . . ) to the fine position PWbi'.

The display image fine position data calculation process outputs the fine position data information RDJi (RDJ1, RDJ2, . . . ; including the wearable device ID) to the moving body information association unit 324c and stores the same in the fine position data record RDi (S162).

The fine position PWbi is thereby displayed on the screen of the tablet 2 as illustrated in FIG. 22.

The display image fine position data calculation process activates the moving body information association unit 324c. The moving body information association unit 324c associates the fine position data information RDJi from the position calculation unit 324d with the moving body information analysis result information KDJi (biometric information, analysis result, . . . ). The moving body information association unit 324c further associates the same with the face photograph and name code to generate the display control data PKJi illustrated in FIG. 14 including the corresponding window number and transmits the same to the tablet 2 (S173).

The moving body information association unit 324c determines whether the wearable device 1 is disconnected (S174). When the wearable device 1 is not disconnected, the display image fine position data calculation process returns to step S150 in FIG. 33.

The screen of FIG. 26 or 36 is thereby displayed on the tablet 2, and the fine positions PWbi illustrated in FIG. 22 is displayed in the real position display window RWi.

The manager MG therefore understands the current situation of a soccer player SPai and how the soccer player SPai is moving, in real time at a glance.

[Process of Moving Body Information Association Unit 324c]

Figure 35:
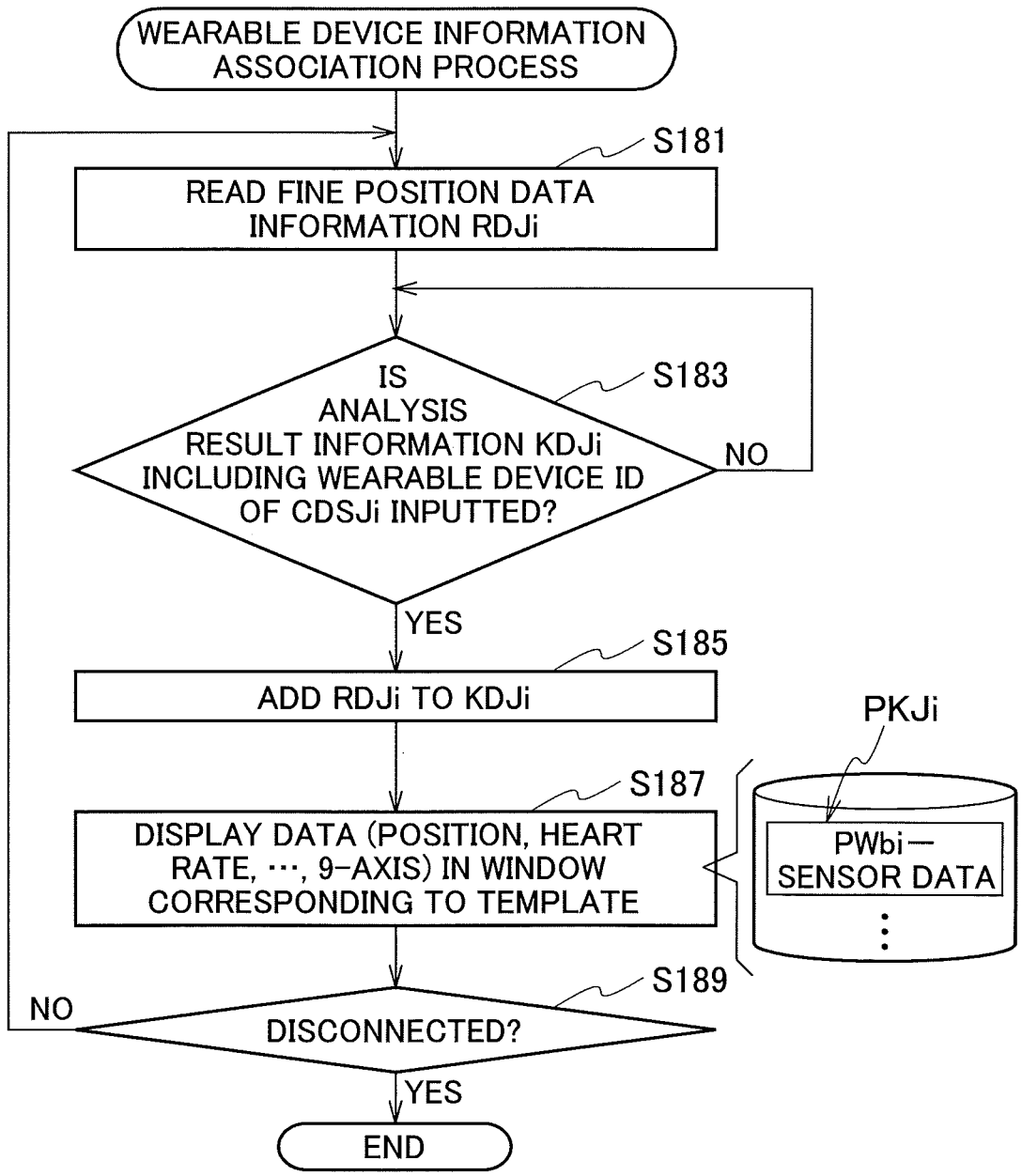
FIG. 35 is a flowchart illustrating processing of a moving body information association unit.

The process of the aforementioned moving body information association unit 324c is described using the flowchart in FIG. 35.

The moving body information association unit 324c reads the fine position data information RDJi (RDJ1, RDJ2, . . . ) with the wearable device ID from the position calculation unit 324d (step S181).

Next, the moving body information association unit 324c determines whether the moving body information analysis result information KDJi (see FIG. 15) that includes the wearable device ID included in the center-side moving body information CDSJi is inputted (step S183).

When determining that the moving body information analysis result information KDJi is inputted in step S183, the moving body information association unit 324c adds the fine position data information RDJi to the moving body information analysis result information KDJi (step S185).

The moving body information association unit 324c creates the display control data PKJi illustrated in FIG. 14, which associates the previously registered template for plural windows WUi with the sensor acquisition type ki (heart rate, body temperature, . . . , or 9-axis sensor) corresponding to the respective window numbers, the fine position data information RDJi, and the moving body information analysis result information KDJi, and transmits the same to the tablet 2 via the Internet protocol (step S187).

The moving body information association unit 324c determines whether the wearable device 1 is disconnected. When the wearable device 1 is not disconnected (NO in step S189), the moving body information association unit 324c returns the process to step S181. When the wearable device 1 is disconnected (YES in step S189), the moving body information association unit 324c terminates the process.

[Screen Display Example of Tablet 2]

FIG. 36 illustrates a screen display example of the tablet 2 based on the aforementioned display control data PKJi (including the camera image CGi).

Specifically, as illustrated in FIG. 36, for example, the analysis screen GKGi of the tablet 2 includes a user face photograph window WU1, a heart rate window WU2, an acceleration window WU3, a posture window WU4, a window WU5, a real position display window RWi, and the like.

In the user face photograph window WU1, for example, profile pictures of soccer players Spa1, Spa2, Spa3, . . . who wear the wearable devices 1 and are already subjected to pairing, are displayed together with GNSS positioning data (fine positions PWbi) of the respective soccer players Spa1, Spa2, Spa3, . . . at that moment.

In the heart rate window WU2, heart rate graphs of the soccer players Spa1, Spa2, Spa3, . . . are displayed. In the acceleration window WU3, acceleration graphs of soccer players Spa1, Spa2, Spa3, . . . are displayed. In the posture window WU4, posture graphs of the soccer players Spa1, Spa2, Spa3, . . . are displayed. In the real position display window RWi, the detection positions Pi (fine positions PWbi) of the soccer players Spa1, Spa2, Spa3, . . . on the camera image CGi are displayed.

The horizontal axes in the heart rate window WU2, acceleration window WU3, posture window WU4, and window WU5 are defined on a scale of the minimum unit (100 ms, for example) of the system time STi. Vertical axis bars Bi (Ba, Bb, Bc, Bd, . . . ) are displayed corresponding to the fine positions PWbi (Pwb1, Pwb2, Pwb3, . . . ) (not illustrated for the soccer players Spa2, Spa3, . . . ).

The user of the tablet 2, the manager MG of the soccer team of interest, for example, is able to understand the situation of each soccer player SPai at the fine position PWbi, how the soccer player SPai is moving, and the like on a fine position scale.

In the aforementioned embodiment, the tablet 2 includes a transfer function to transfer the information detected by the wearable device 1 to the analysis result providing apparatus 3. However, the transfer function may be provided as a transfer-dedicated communication device (not illustrated) near the soccer field Ai, for example.

FIG. 36 illustrates just an example of the screen display of the tablet 2. For example, the tablet 2 can also display current data and past data of the same soccer player SPai for comparison or display only the user face photograph window WU1 on the screen so as to show the profile pictures and GNSS positioning data (fine positions PWbi) of more soccer players Spai (not illustrated).

Hereinafter, a description is given of the specific configuration of the wearable device 1.

Figure 37:
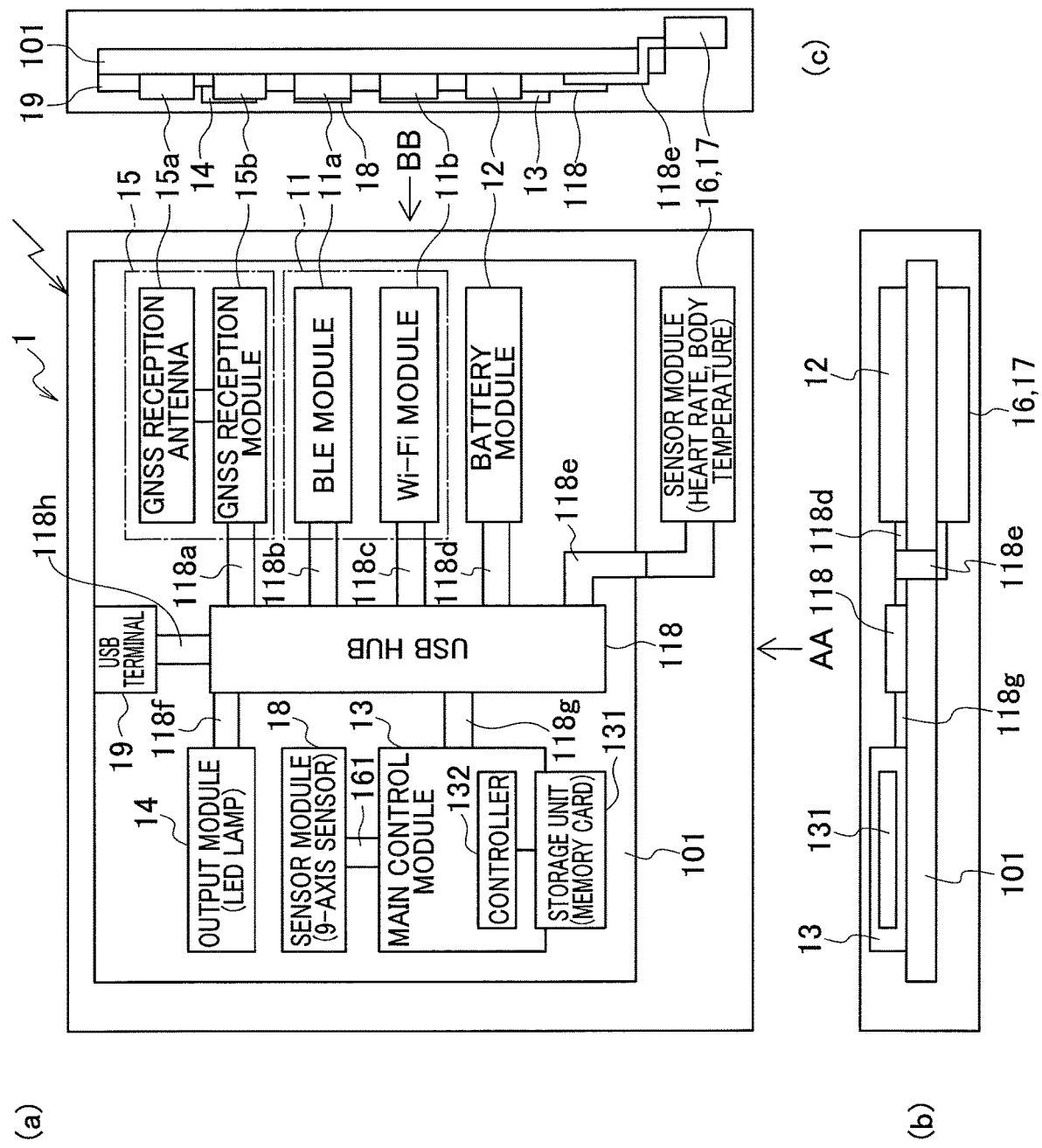
FIG. 37 is a schematic configuration diagram illustrating a specific example of the wearable device.

FIG. 37 is a schematic configuration diagram of the wearable device 1.

FIGS. 37(*a*), 37(*b*), and 37(*c*) schematically illustrate a planar configuration of the wearable device 1, a side configuration thereof in the direction AA, and a side configuration thereof in the direction BB, respectively. The wearable device 1 may be integrated as an IC but is illustrated in a circuit diagram in Embodiment 2.

In the description of FIG. 37, the position sensor 15 (GNSS module), the biometric information detection sensor 16, the environment information detection sensor 17, and the moving body state information detection sensor 18 (9-axis sensor) are illustrated by way of example. The biometric information detection sensor 16, environment information detection sensor 17, and moving body state information detection sensor 18 are desirably configured to be attached or detached according to the need.

In FIG. 37, the wearable device 1 includes the wireless module 11 (wireless communication module), the battery module 12, the main control module 13, the output module 14, the position sensor 15, the biometric information detection sensor 16, the environment information detection sensor 17, the USB hub 118 (Universal Serial Bus), a USB terminal 19 for charge and external connection, the moving body state information detection sensor 18, and the like, which are mounted on a mounting substrate 101 (also referred to as a base).

The wireless module 11 includes a BLE module 11*a* (Bluetooth (registered trademark) Low Energy module) and a Wi-Fi module 11*b*. For communication with the tablet 2, the wireless module 11 connects to a communication link to continue communication, using later described initial connection setting information, which is set by the main control module 13.

The position sensor 15 includes a GNSS reception antenna 15*a* and a GNSS reception module 15*b*, for example.

The biometric information detection sensor 16 includes sensors detecting the biometric information SEJi, including the heart rate, pulse rate, and body temperature, and outputs sensing results obtained by the sensors at individual specific times, as the sensor data SDi. The biometric information detection sensor 16 thus detects various types of biometric information SEJi of the soccer player SPai at specific times and outputs the detected values (sensing results) as the sensor data SDi of the biometric information SEJi.

The environment information detection sensor 17 includes sensors detecting the environment information SKJi, including the atmospheric pressure, temperature (ambient temperature), and humidity, and outputs sensing results obtained by the sensors at individual specific times, as the sensor data SDi. The environment information detection sensor 17 thus detects the environment information SKJi around the soccer player SPai at specific times and outputs the detected values (sensing results) as the sensor data SDi of the environment information SKJi.

The moving body state information detection sensor 18 includes a 9-axis sensor that detects the posture value, acceleration, and direction of the soccer player SPai. The moving body state information detection sensor 18 is directly connected to the main control module 13 through a signal line 161 (I2C (Inter Integrated Circuit)/SPI (Serial Peripheral Interface) and the like) in order to detect the posture value, acceleration, and direction at intervals of 100 ms, for example. Each time detecting the posture value, acceleration, and direction of the soccer player SPai, the moving body state information detection sensor 18 outputs the detected values (sensing results) as the sensor data SDi of the 9-axis sensor information eJi of the moving body.

The main control module 13 of the wearable device 1 includes the controller 132 and the storage unit 131 (the device-side position calculation data storage unit (330)).

The storage unit 131 may be an SD memory card or the like. The storage unit 131 has a capacity of 16 GB, for example and is used as a storage for the activation program and data. In the storage unit 131, a memory region (hereinafter, referred to as a sensor data storage region 131*c*) to store sensor data SDi from the position sensor 15, biometric information detection sensor 16, environment information detection sensor 17, and moving body state information detection sensor 18, for example. The sensor data storage region 131*c* can be configured using a RAM provided within the controller 132 or the like.

The main control module 13 is connected to the USB hub 118 through a USB bus (signal cable) 118*g*. Ports of the USB hub 118 are individually connected to: the GNSS reception module 15*b* of the position sensor 15 via a USB bus 118*a*; the BLE module 11*a* of the wireless module 11 via a USB bus 118*b*; the Wi-Fi module 11*b* of the wireless module 11 via a USB bus 118*c*; the battery module 12 via a USB bus 118*d*; the sensors of the biometric information detection sensor 16 and environment information detection sensor 17 via a USB bus 118*e*; the output module 14 via a USB bus 118*f*; and the USB terminal 19 via a USB bus 118*h*.

The USB hub 118 watches the input ports (not illustrated) regularly (at intervals of several milliseconds, for example). When there is an input to any input port, the USB hub 118 outputs the inputted signal (position data, heart rate data, . . . , BLE data, Wi-Fi data, USB data, . . . ) to the main control module 13. The USB hub 118 outputs signals from the main control module 13 to the corresponding modules 11*a*, 11*b*, or the like.

The GNSS reception module 15*b* is connected to the GNSS reception antenna 15*a* and generates 1 PPS signal included in the frame header every one second (one clock waveform per second), for example. The GNSS reception module 15*b* outputs Raw data according to the GNSS data received from a GNSS satellite AS1 through the GNSS reception antenna 15*a*, to the main control module 13 through the USB hub 118.

The BLE module 11*a* is a wireless communication module to transmit and receive data via the Bluetooth (registered trademark) protocol.

The Wi-Fi module 11b is a wireless communication module certified by Wi-Fi Alliance for wireless local area network (LAN).

The output module 14 may be provided with an LED lamp, a vibrator, a buzzer, and the like (not illustrated) for notification of the wearable device 1 being in charge, the battery level thereof, and the like, for example.

The USB terminal 19 is used to charge the battery module 12 and connect to a not-illustrated external device, such as a personal computer.

The biometric information detection sensor 16 is a heart rate sensor or the like. For example, the heart rate sensor acquires heart rate data obtained by sensing with a certain period as the sensor data SDi, which are digital values, and outputs the heart rate data at this acquisition time to the USB hub 118.

The environment information detection sensor 17 is a temperature sensor or the like. For example, the temperature sensor acquires ambient temperature data obtained by sensing with a certain period as the sensor data SDi, which are digital values, and outputs the ambient temperature data at this acquisition time to the USB hub 118.

The moving body state information detection sensor 18 is a gyroscope or the like. For example, the gyroscope acquires posture value data by sensing with a certain period as the sensor data SDi, which are digital values, and outputs the posture value data at this acquisition time to the USB hub 118.

Figure 38:
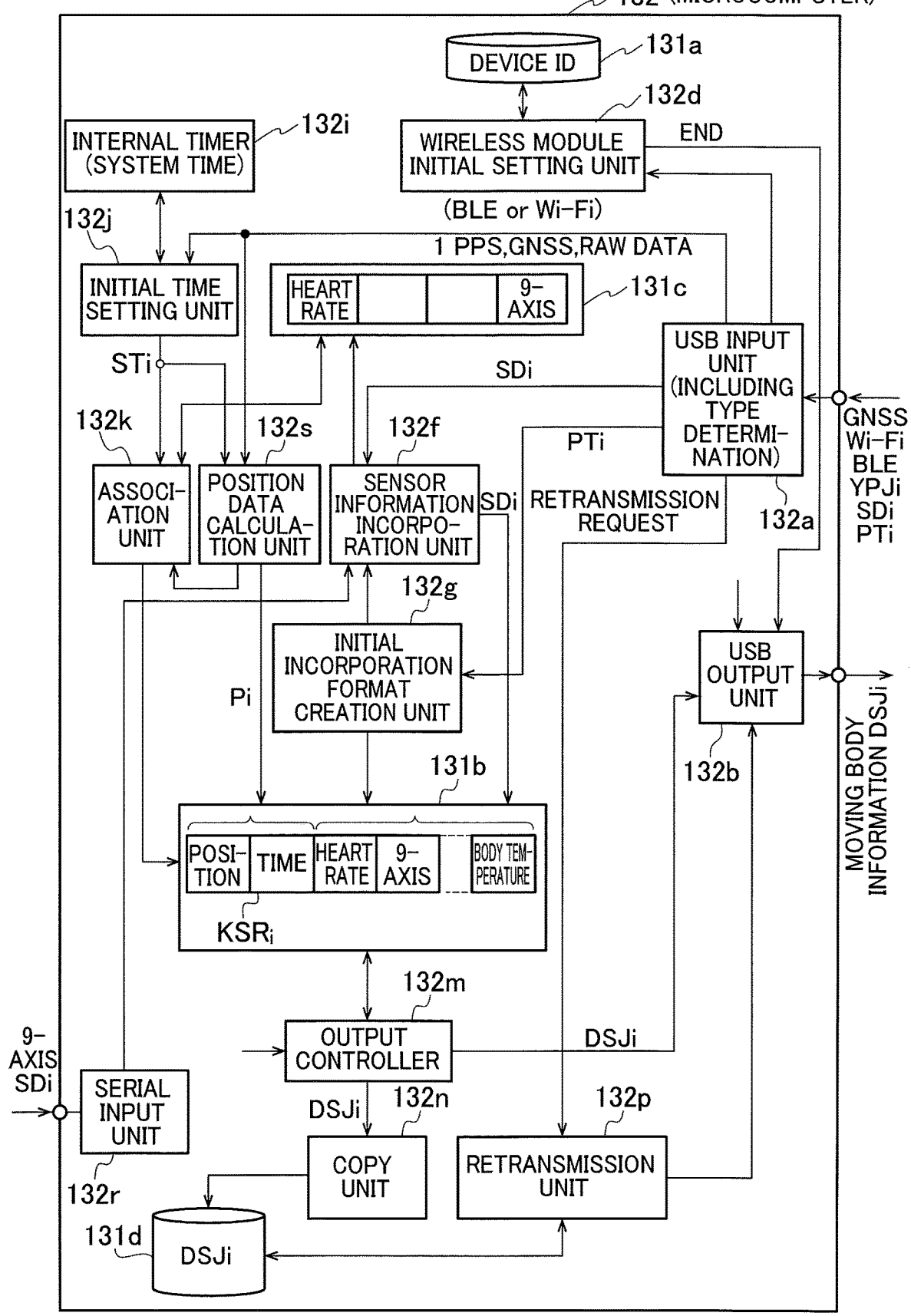
FIG. 38 is a schematic diagram illustrating functional blocks of a controller in a main control module of the wearable device.

FIG. 38 illustrates a schematic program configuration (functional blocks) of the controller 132 in the main control module 13 of the wearable device 1.

The controller 132 sets the system time STi of the internal timer 132i (system clock) to the GNSS time (Raw data) for initial synchronization. The controller 132 causes transmission of the moving body information DSJi that associates the biometric information SEJi, including the heart rate, pulse rate, and body temperature of the soccer player SPai in the soccer field Ai, the 9-axis sensor information eJi, including the posture value and acceleration of the soccer player SPai, and the environment information SKJi, including the atmospheric pressure around the soccer player SPai, with the position information (Raw data) of the position sensor 15 as the GNSS module. The system time STi is arbitrary but is preferably synchronized with output timing of the sensor that senses the earliest after the GNSS time.

The controller 132 sets the system time STi of the internal timer 132i based on the reference time included in the pairing request information from the tablet 2.

The controller 132 includes a USB input unit 132a, a USB output unit 132b, a wireless module initial setting unit 132d, a sensor information incorporation unit 132f, an initial incorporation format creation unit 132g, the internal timer 132i, the initial time setting unit 132j (also referred to as an initial synchronization unit), an association unit 132k, an output controller 132m, a copy unit 132n, a retransmission unit 132p, a serial input unit 132r, a position data calculation unit 132s, and the like.

The USB input unit 132a incorporates outputs from the GNSS wireless module 11, Raw data of the GNSS reception module 15b of the position sensor 15 as the GNSS module, sensing results of the biometric information detection sensor 16, and the like through the USB hub 118 and includes a function to determine the type of the input, for example.

The USB input unit 132a receives inputted signal (data), determines the contents, and provides the signal to a proper section according to the determination result.

When the inputted signal is the transmission pattern PTi from the tablet 2, for example, the USB input unit 132a provides the same to the initial incorporation format creation unit 132g. When the inputted signal is an instruction concerning initial setting of the wireless module 11 from the tablet 2 (in initial operation), for example, the USB input unit 132a provides the same to the wireless module initial setting unit 132d.

When the inputted signal is Raw data, 1 PPS signal, or signal concerning the GNSS time from the GNSS reception module 15 (in initial operation), for example, the USB input unit 132a provides the same to the initial time setting unit 132j and position data calculation unit 132s.

When the inputted signal is the sensor data SDi of the biometric information SEJi from the biometric information detection sensor 16 or the sensor data SDi of the environment information SKJi from the environment information detection sensor 17, for example, the USB input unit 132a provides the same to the sensor information incorporation unit 132f.

When the inputted signal is a retransmission request XRi from the tablet 2, for example, the USB input unit 132a provides the same to the retransmission unit 132p.

The tablet 2 notifies the USB input unit 132a of the sensor acquisition type ki (any one of the heart rate, . . . , 9-axis sensor information, or a combination thereof, for example) according to the sensor data SDi to be incorporated by the tablet 2.

In response to the notification, the serial input unit 132r incorporates the moving body state information (the 9-axis sensor information eJi) from the moving body state information detection sensor 18, as the sensor data SDi and provides the same to the sensor information incorporation unit 132f.

When the wearable device 1 is powered on, the wireless module initial setting unit 132d activates the wireless module 11.

Each time receiving a connection request including the tablet ID of the tablet 2 from the BLE module 11a or Wi-Fi module 11b of the wireless module 11 through the USB hub 118, the wireless module initial setting unit 132d transmits information including the wearable device ID previously registered in the memory region 131a of the storage unit 131, for example, for connection of a communication link. The connection initial setting information at the time when the communication link is connected is set in the wireless module 11, for example. The connection initial setting information is stored until disconnection.

Each time receiving from the USB input unit 132a, the transmission pattern PTi (see FIG. 21) transmitted from the tablet 2, the initial incorporation format creation unit 132g creates the transmission format KSRi based on the received transmission pattern PTi in the storage unit 131, for example. The region of the transmission format KSRi created in the storage unit 131 is also referred to as a transmission format pattern memory 131b.

The controller 132 then waits for the sensor acquisition types ki from the tablet 2.

When receiving the sensor acquisition type ki, the initial incorporation format creation unit 132g creates the number of sensor data transmission regions corresponding to the sensor acquisition types ki in latter part of the transmission format KSRi.

The whole length (the total number of sensor data transmission regions) of the transmission format KSRi increases or decreases according to the sensor acquisition type ki from the tablet 2. The less the kinds of sensor data in the sensor acquisition type ki from the tablet 2, the shorter the date to be transmitted.

The initial time setting unit 132*j* receives the 1 PPS signal and Raw data as the source data of the GNSS time or the like, from the position sensor 15 (GNSS module) through the USB input unit 132*a* and the system time STi (GNSS time>system time STi) from the internal timer 132*i* and synchronizes the system time STi with the GNSS time (Raw data).

The sensor information incorporation unit 132*f* determines whether the sensor data SDi of the biometric information detection sensor 16 or the sensor data SDi of the environment information detection sensor 17 are outputted from the USB input unit 132*a*. When the sensor data SDi of the biometric information detection sensor 16 or environment information detection sensor 17 are outputted, the USB input unit 132*a* determines the sensor acquisition type ki. The USB input unit 132*a* determines the existence of the sensor that has outputted the sensor data SDi and specifies the type thereof.

When the type of the sensor is specified, the sensor data SDi is overwritten and saved in the corresponding sensor data transmission region in the sensor data storage region 131*c*. The sensor data SDi of the biometric information SEJi and the environment information SKJi are outputted at different times but are retained until the next sensor data SDi are outputted.

The sensor information incorporation unit 132*f* determines whether the sensor data SDi of the moving body state information detection sensor 18 is outputted from the serial input unit 132*r*. When the sensor data SDi is outputted, the sensor information incorporation unit 132*f* sequentially overwrites and stores the sensor data SDi in the corresponding sensor data transmission region in the sensor data storage region 131*c*.

In such a manner, in the sensor data storage region 131*c*, even if the sensors, including the biometric information detection sensor 16, environment information detection sensor 17, and moving body state information detection sensor 18, output the sensor data SDi at different times, the stored sensor data SDi are retained until the next sensor data SDi are outputted.

The position data calculation unit 132*s* calculates and outputs the detection position Pi of the wearable device 1 regularly (every one second, for example) based on Raw data from the position sensor 15 as the GNSS module, the synchronized system time STi, and the like.

When receiving the moving body information request information YDJi requesting the moving body information DSJi, from the tablet 2 through the wireless module 11 and USB input unit 132*a*, the association unit 132*k* writes the latitude Ei and the longitude Ni of the detection position Pi and the system time STi of acquisition thereof, in the top of the transmission format KSRi in the transmission format pattern memory 131*b* as the header information (position information).

The association unit 132*k* reads the sensor data SDi (detected at different times) of the sensor data storage regions 131*c* at the time in which this system time STi is acquired. The association unit 132*k* then writes the same in latter part of the transmission format KSRi.

After synchronization of the Raw data as the source data of the detection position Pi and the system time STi, the association unit 132*k* reads the sensor data SDi detected at the time the calculated detection position Pi is outputted, from the sensor data storage region 131*c*. The association unit 132*k* writes the same in the transmission format KSRi of the transmission format pattern memory 131*b* (overwrite).

In this process, the association unit 132*k* writes all the data of the system time STi, detection position Pi, and the like into numerical strings in the transmission format KSRi. Each format region of the transmission format KSRi is defined based on the sensor acquisition type ki in advance. The tablet 2 and analysis result providing apparatus 3 therefore can decode data even if the data is transmitted in the transmission format KSRi.

Representing all the data of the transmission format KSRi in numerical strings can increase the amount of data that can be transmitted by the transmission format KSRi.

In addition, changing the order of the numerical strings or the order of the format regions in the transmission format KSRi, which is defined based on the sensor acquisition type ki, makes it difficult for the other devices than the tablet 2 or analysis result providing apparatus 3 to decode data transmitted in the transmission format KSRi.

At each end of the association process, the output controller 132*m* fills each sensor data transmission region of the transmission format KSRi in the transmission format pattern memory 131*b* and transmits the same as the moving body information DSJi to the tablet 2 from the wireless module 11 through the USB output unit 132*b*.

The output controller 132*m* frees (deletes) the sensor data transmission regions in the transmission format KSRi in which any sensor data SDi is not formatted while forming the moving body information DSJi using only the sensor data transmission regions in which the sensor data SDi are formatted.

The copy unit 132*n* copies the moving body information DSJi and stores the same in a moving body situation detection information storage memory region 131*d* (also referred to as a copy region).

When the moving body information request information YDJi inputted into the USB input unit 132*a* from the tablet 2 (see FIG. 13) includes a retransmission request, the retransmission unit 132*p* reads the moving body information DSJi corresponding to the moving body information request information YDJi from the moving body situation detection information stored memory region 131*d* and retransmits the same to the tablet 2 through the USB output unit 132*b*.

Figure 39:
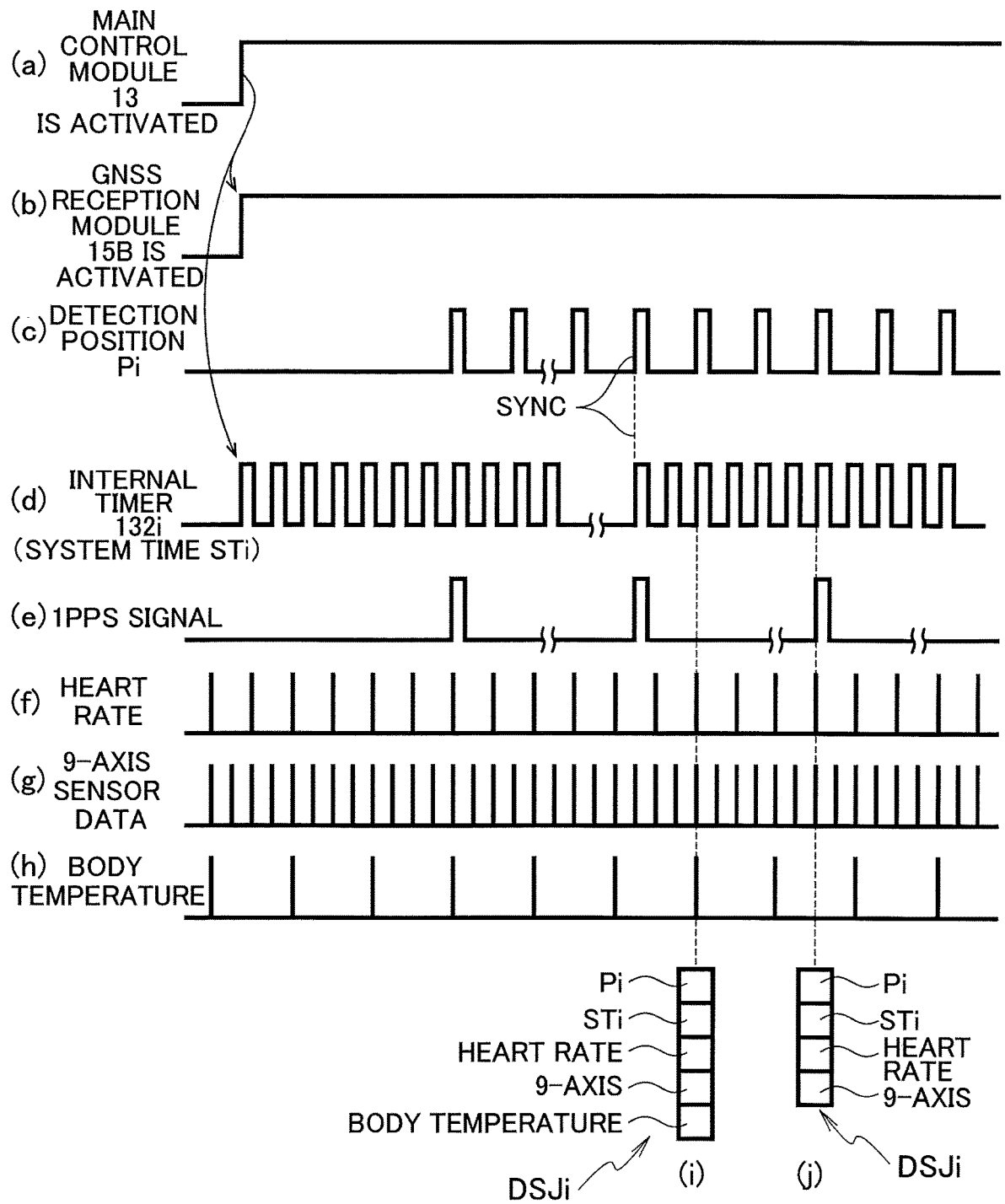
FIG. 39 is a timing diagram illustrating an operation of the wearable device.

Next, additional explanation is given of the process until the wearable device 1 transmits the moving body information DSJi using the timing diagram of FIG. 39.

FIG. 39(*a*) illustrates activation of the main control module 13; FIG. 39(*b*) illustrates activation of the position sensor 15 as the GNSS module; and FIG. 39(*c*) illustrates outputs of the detection position Pi in time domain FIG. 39(*d*) illustrates outputs of the internal timer 132*i* (system time STi) in time domain; and FIG. 39(*e*) illustrates outputs of the 1 PPS signal from the position sensor 15 as the GNSS module in time domain. FIG. 39(*f*) illustrates outputs of the sensor data SDi of the heart rate in time domain; FIG. 39(*g*) illustrates outputs of the sensor data SDi of the 9-axis sensor information eJi in time domain, and FIG. 39(*h*) illustrates outputs of the sensor data SDi of body temperature in time domain.

As illustrated in FIG. 39, upon activation of the main control module 13, the internal timer 132*i* and the sensor modules including the position sensor 15, the biometric information detection sensor 16, the environment information detection sensor 17, and the moving body state information detection sensor 18 are activated.

FIG. 39(i) illustrates a format example of the transmission format KSRi at the time the sensor data SDi of the heart rate, the sensor data SDi of the 9-axis sensor information eJi, the sensor data SDi of the body temperature and the system time STi synchronize. FIG. 39(j) illustrates a format example of the transmission format KSRi at the time the sensor data SDi of the 9-axis sensor information eJi and the system time STi synchronize.

Even if the sensors of the wearable device 1 output the sensor data SDi (the heart rate, body temperature, . . . , 9-axis sensor information) at different times, all the types of sensor data SDi that are held at that moment can be formatted on the transmission format KSRi at the time nearest to or same as the system time STi.

The output controller 132m transmits the data of the transmission format KSRi as the moving body information DSJi, to the tablet 2 with the wireless module 11 through the USB output unit 132b.

The tablet 2 is thereby able to display the heart rate, acceleration, posture value, and the like in association with the fine position PWbi of a soccer player SPai. This allows for understanding of the location and motion of the soccer player SPai, the situation at that moment, and the like in detail on a fine position PWbi scale on the screen.

Embodiment 3

Embodiment 3 includes a function of simultaneously collecting the moving body information of plural soccer players SPai. Embodiment 3 employs Real-time kinematic (RTK) in order to always maintain the position accuracy.

Figure 40:
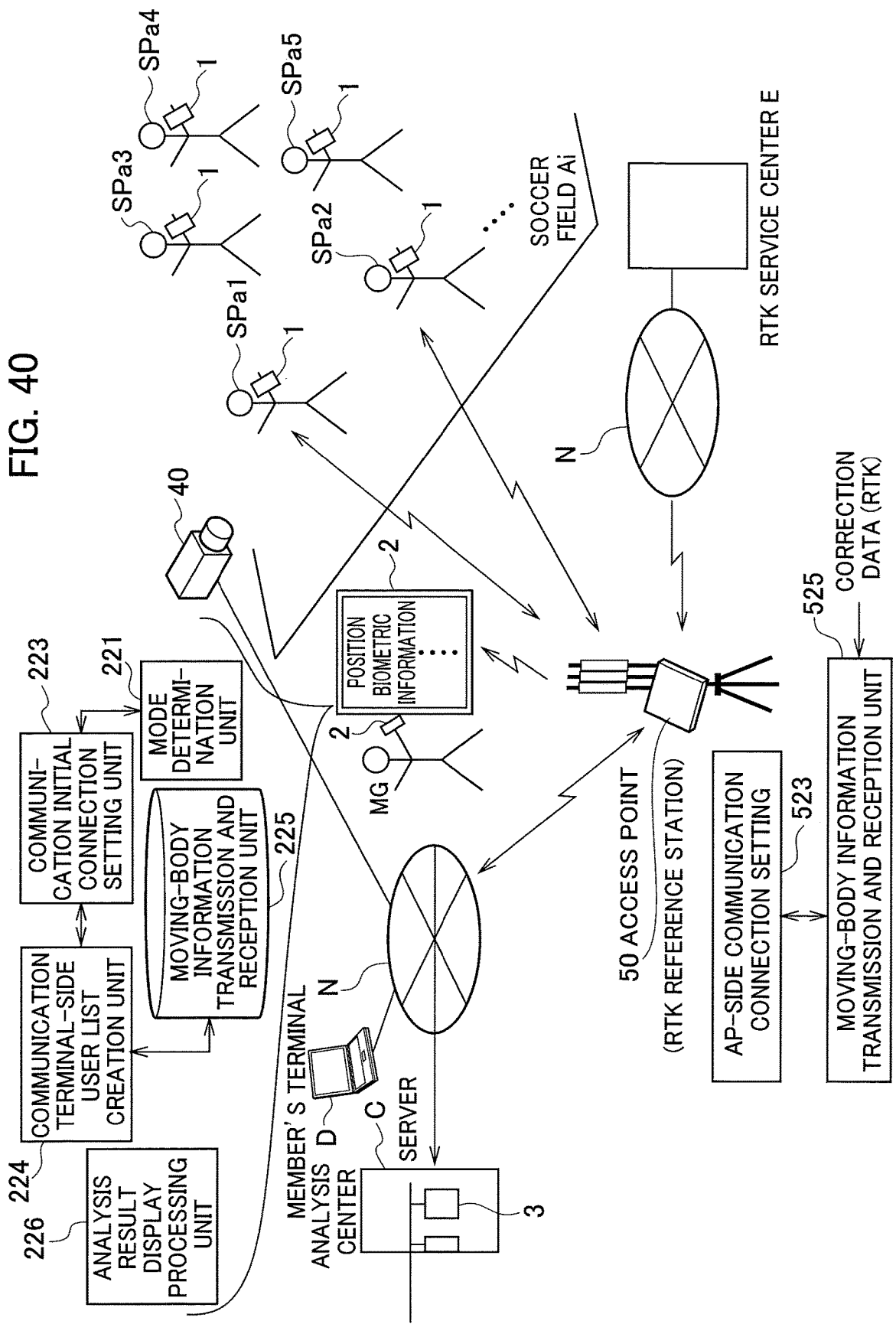
FIG. 40 is a schematic configuration diagram of a moving body information providing system according to Embodiment 3.
Figure 41:
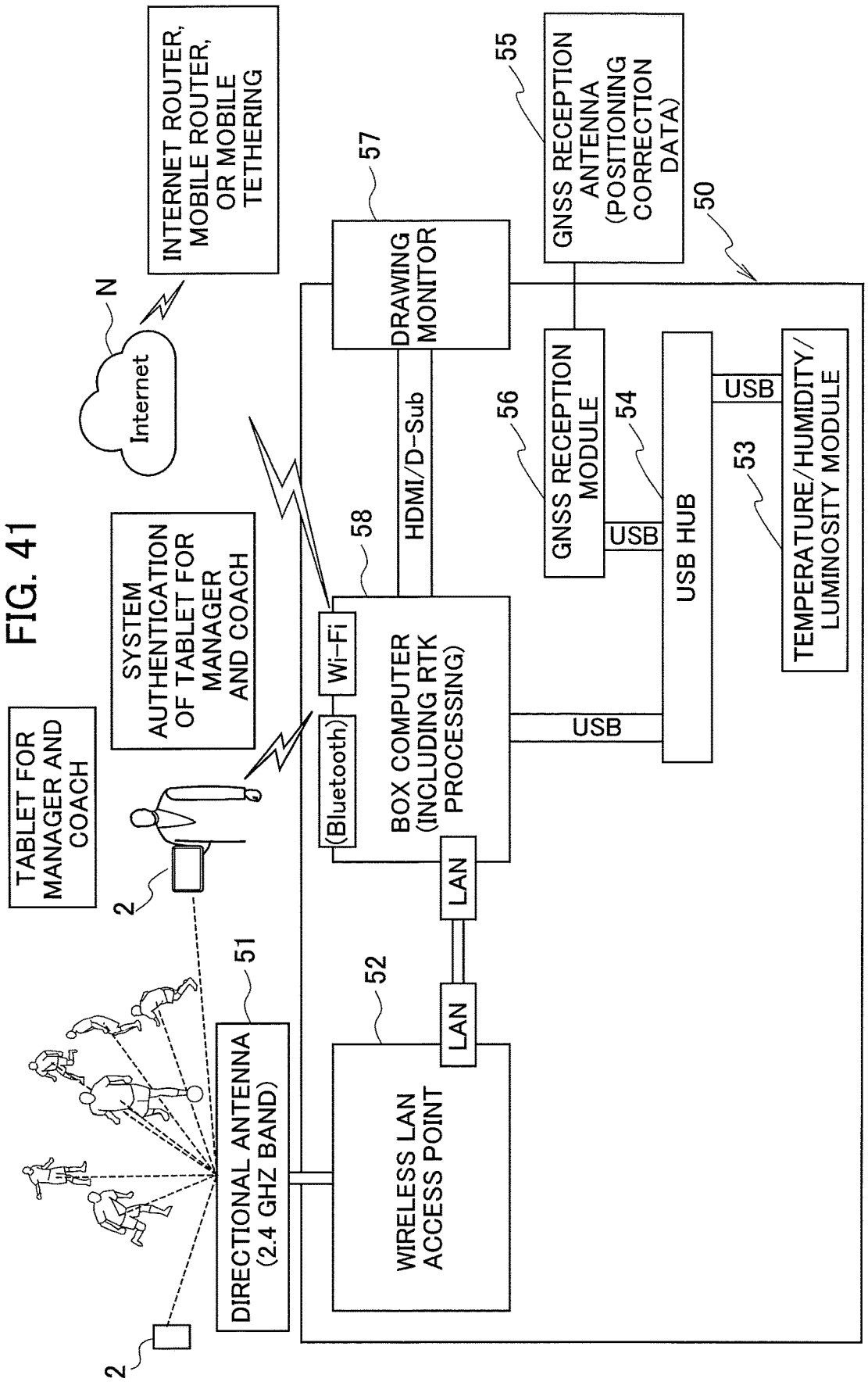
FIG. 41 is a schematic configuration diagram of an RTK reference station in the moving body information providing system.

FIG. 40 is a schematic configuration diagram of a moving body information providing system according to Embodiment 3. In FIG. 40, description of components given the same reference numerals as those of the above embodiments are omitted. FIG. 41 is a specific hardware configuration diagram of an RTK reference station 50.

As illustrated in FIG. 40, the moving body information providing system according to Embodiment 3 includes the RTK reference station 50 as an access point.

The moving body information providing system of Embodiment 3 further includes the same communication initial connection setting unit 223, communication terminal-side user list creation unit 224, analysis result display processing unit 226, and the like as those of Embodiment 2 on the tablet 2 side.

The moving body information providing system of Embodiment 3 further includes the same RTK reference station 50 as that of Embodiment 2 and an AP-side moving body information transmission and reception unit 525, and the like on the RTK reference station 50 side. In the following description, the pairing information PJi is AP connection information.

Since the same RTK reference station 50 as that of Embodiment 2, the AP-side moving body information transmission and reception unit 525, and the like are provided on the RTK reference station 50 side, the processes by the communication initial connection setting unit 223, communication terminal user list creation unit 224, analysis result display processing unit 226, and the like are a little different from those of Embodiment 2. These are described later.

First, the configuration in FIG. 41 is described. The RTK reference station 50 includes the antenna 51, the wireless LAN access point 52 as a wireless communication device, an external environment detection module 53 for temperature, humidity, and luminosity detection, a USB hub 54, a GNSS reception antenna 55, a GNSS reception module 56 (GNSS receiver), a drawing monitor 57, a box computer 58, and the like as illustrated in FIG. 41.

In the wireless LAN access point 52, an access point address or the like are set by the box computer 58.

The box computer 58 receives positioning data from the GNSS reception module 56, reference data through Wi-Fi router (or Bluetooth (registered trademark)), position information of the wearable device 1 from the wireless LAN access point 52, for example, to create correction data for positions based on the received data and a reference position. The created correction data is transmitted through the wireless LAN access point 52 from the antenna 51 to any one of the wearable device 1, tablet 2, and analysis result providing apparatus 3. The correction data is transmitted to the tablet 2 when the tablet 2 includes a function of receiving the moving body information DSJi like Embodiment 2. In this case, the tablet 2 corrects the detection position Pi of the moving body information DSj based on the correction data. The system time may be corrected.

The aforementioned box computer 58 includes the RTK reference station 50, AP-side moving body information transmission and reception unit 525, and the like.

[Tablet in Embodiment 3]

The communication initial connection setting unit 223 of the tablet 2 performs communication connection (Wi-Fi) with the RTK reference station 50 of the RTK reference station 50.

[[Mode Determination Unit 221]]

When the communication initial connection setting button MGb is selected in the mode selection screen MGi illustrated in FIG. 16, the mode determination unit 221 activates the communication initial connection setting unit 223. When the user list registration button MGa or actual participant registration button MGd is selected, the mode determination unit 221 activates the communication terminal-side user list creation unit 224.

When the moving body information acquisition button MGf (the moving body information acquisition mode) is selected, the mode determination unit 221 activates the moving body information transmission and reception unit 225.

[[Communication Initial Connection Setting Unit 223]]

When activated, the communication initial connection setting unit 223 communicates with a not-illustrated reference time service center to acquire current time and sets the internal timer (not illustrated) to the current time. The communication initial connection setting unit 223 thus sets the initial time.

The communication initial connection setting unit 223 then transmits the AP connection information (the tablet ID, type, maker, time, and the like) to the RTK reference station 50.

[[Communication Terminal-Side User List Creation Unit 224]]

When activated, the communication terminal-side user list creation unit 224 previously transmits user registration information as user basic registration information UJi (see FIG. 18) to the analysis result providing apparatus 3 via the RTK reference station 50 for registration. The user registration information enables the service to be provided and includes names of the soccer players SPai, wearable device IDs of the wearable devices 1, and the like.

The name field in the moving body information request input screen KBGc (FIG. 19) includes input fields for plural players (about 20 players, for example). This allows for communication with plural wearable devices 1.

[Moving Body Information Transmission and Reception Unit 225]

When receiving the actual participant user communication preparatory registration completion information REJi (see FIG. 17(c)) from the communication terminal-side user list creation unit 224, the moving body information transmission and reception unit 225 reads the camera image CGi from the analysis result providing apparatus 3 via the RTK reference station 50 and displays the camera image CGi on the screen of the tablet 2.

[Analysis Result Display Processing Unit 226]

The analysis result display processing unit 226 transmits the information inputted in the moving body information request input screen KBGc to the analysis result providing apparatus 3 via the RTK reference station 50 as the moving body information analysis request input information KBJi (see FIG. 20), that requests what kind of sensor data SDi to analyze and how long (the time range Wti) to analyze.

The analysis result display processing unit 226 then waits for the display control data PKJi (see FIG. 14), which is transmitted from the analysis result providing apparatus 3 and is used to display on the screen, the detection position Pi and moving body information DSJi (moving body information DSJi, see FIG. 12) of the soccer player SPai in the soccer field Ai (described later).

Each time receiving the display control data PKJi, the analysis result display processing unit 226 outputs the same to the browser for screen display (see FIG. 23).

[RTK Reference Station 50]

The RTK reference station 50 of the RTK reference station 50 performs similar processing to that of the communication initial connection setting unit 223 of the tablet 2 of Embodiment 2.

[[RTK Reference Station 50]]

The RTK reference station 50 communicates with the not-illustrated reference time service center to acquire the current time and sets the internal timer (not illustrated) to the current time. The RTK reference station 50 thus sets the initial time.

The RTK reference station 50 transmits the AP connection information (the access point ID, type, maker, time, and the like) to the wearable devices 1 and is connected to the wearable devices 1.

Specifically, the box computer 52 of the RTK reference station 50 activates the wireless LAN access point 52, and the wireless LAN access point 52 transmits the AP connection information through the antenna 51 via the Wi-Fi (registered trademark) protocol.

When receiving the moving body information request information YDJi from the tablet 2 through the wireless LAN access point 52, the RTK reference station 50 outputs the AP-side moving body information transmission and reception unit 525.

[[AP-Side Moving Body Information Transmission and Reception Unit 525]]

The AP-side moving body information transmission and reception unit 525 of the box computer 52 reads the moving body information request information YDJi and transmits the same to the wearable device 1 with the wireless LAN access point 52 via the Wi-Fi (registered trademark) protocol through the antenna 51.

Each time the box computer 52 receives the moving body information DSJi from the wearable device 1 through the wireless LAN access point 52, the AP-side moving body information transmission and reception unit 525 transmits the same to the analysis result providing apparatus 3 through the Internet router.

The AP-side moving body information transmission and reception unit 525 transmits the moving body information analysis request input information KBJi from the tablet 2 to the analysis result providing apparatus 3.

The AP-side moving body information transmission and reception unit 525 receives a camera image CGi from the analysis result providing apparatus 3, the display control data PKJi (see FIG. 14), and the like through the wireless LAN access point 52 and transmits the same to the tablet 2.

The AP-side moving body information transmission and reception unit 525 further calculates correction data to correct the position based on the positioning data from the RTK service center through the GNSS reception module 56 and the difference between reference data from the RTK service center through a Wi-Fi (registered trademark) router (or Bluetooth (registered trademark)) and the previously set reference position. The AP-side moving body information transmission and reception unit 525 transmits the calculated correction data to the wearable device 1 and the tablet 2 from the antenna 51 through the wireless LAN access point 52 or the analysis result providing apparatus 3 through the Internet router.

In Embodiment 3, the tablet 2 does not perform communications with each wearable device 1 while the RTK reference station 50 performs all the communications with the wearable devices 1. Accordingly, Embodiment 3 allows for simultaneous communications with more wearable devices 1 than that in Embodiment 2.

In addition, the position (that may include the system time) is corrected with the correction data from the RTK reference station 50. This can maintain the position accuracy, and the calculated fine positions are therefore accurate.

[Usage Example of Correction Data]

[[Wearable Device 1]]

Figure 42:
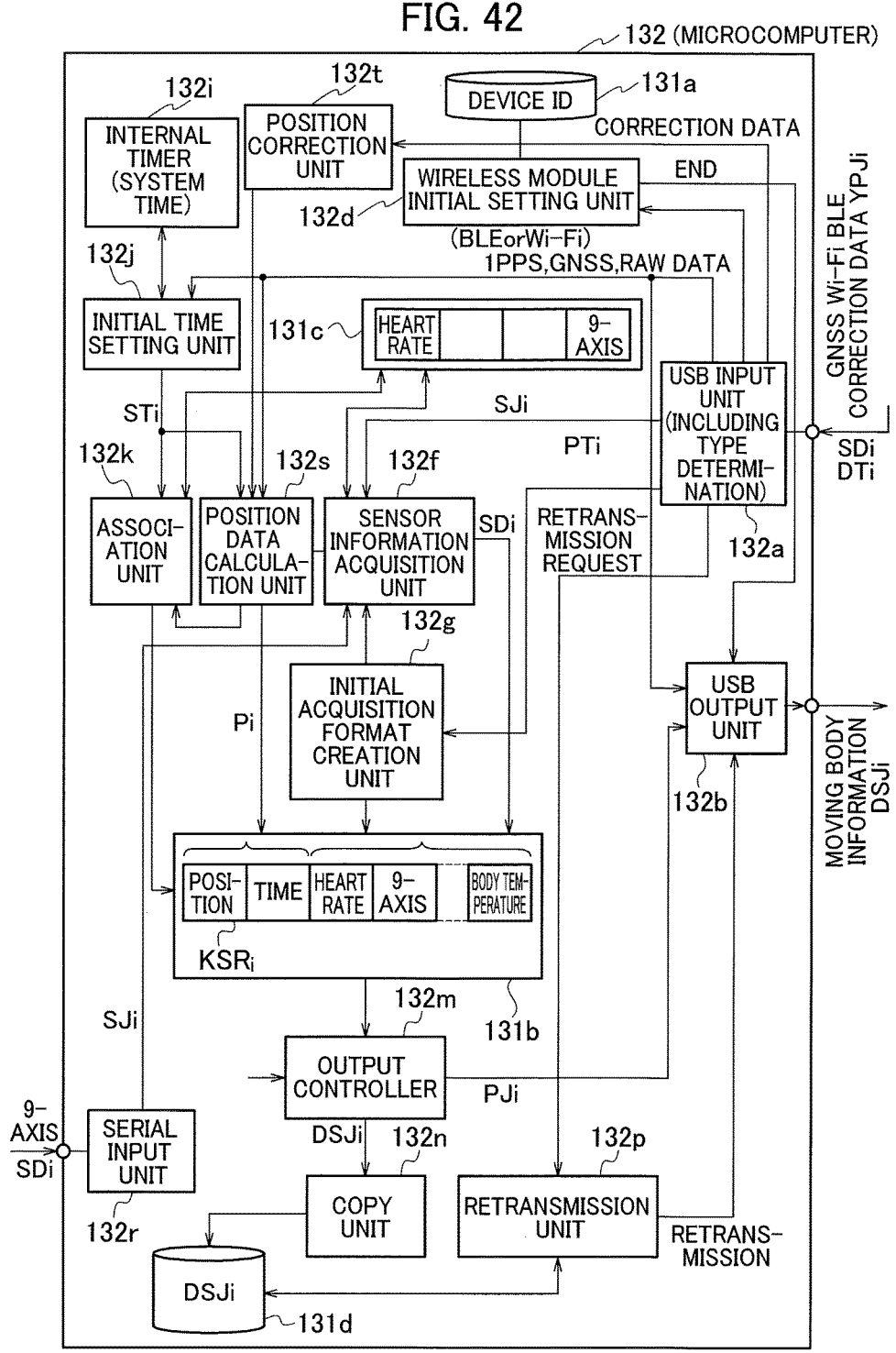
FIG. 42 is a schematic program configuration diagram of a controller of an RTK wearable device.

Using FIG. 42, a description is given of a case where the correction data from the RTK reference station 50 is used by the wearable device 1.

In FIG. 42, the description of the components given the same reference numerals as those in FIG. 38 is omitted.

The controller 132 of the main control module 13 further includes a position correction unit 132t as illustrated in FIG. 42. The position correction unit 132t incorporates the correction data from the RTK reference station 50 through the USB input unit 132a. The position calculation unit 132s corrects the calculated detection position Pi (latitude Ei, longitude Ni) of the wearable device 1 with the correction data received by the position correction unit 132t.

[[Analysis Result Providing Apparatus 3]]

Figure 43:
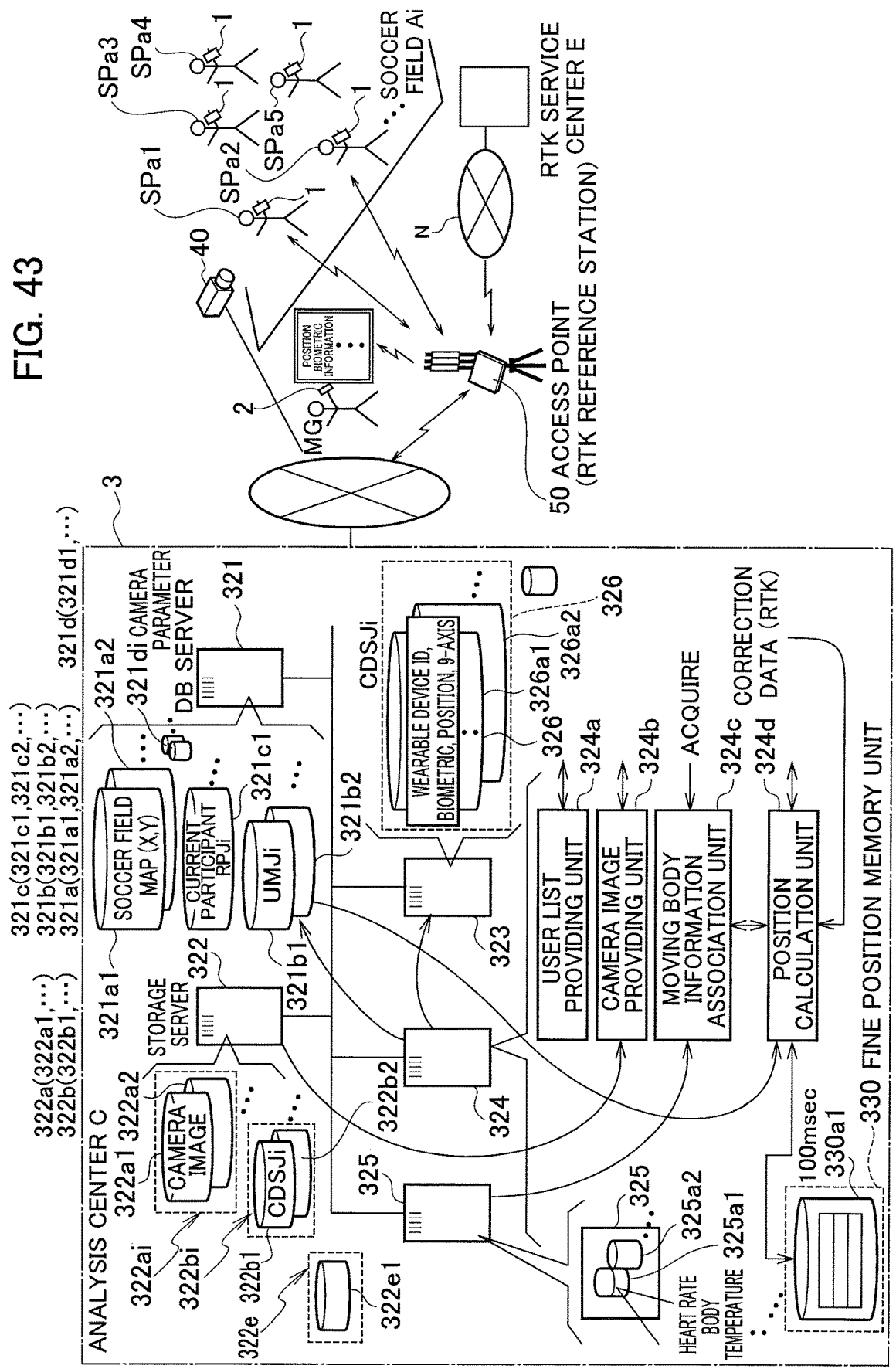
FIG. 43 is a schematic configuration diagram of an RTK analysis result providing apparatus.

FIG. 43 is an example of the case where the correction data from the RTK reference station 50 is transmitted to the analysis result providing apparatus 3. In FIG. 43, the description of the components given the same reference numerals as those in FIG. 24 is omitted.

The moving body position-related information creation server 324 incorporates the correction data from the RTK reference station 50 into the position calculation unit 324d as illustrated in FIG. 43. The position calculation unit 324d corrects the calculated detection position Pi (latitude Ei, longitude Ni) of the wearable device 1 with the received correction data.

In any of the above cases, using the correction data based on RTK positioning to correct the detection position Pi allows the fine position PWbi calculated by the analysis result providing apparatus 3 to be always obtained at a certain degree of accuracy.

Other Embodiments

Figure 44:
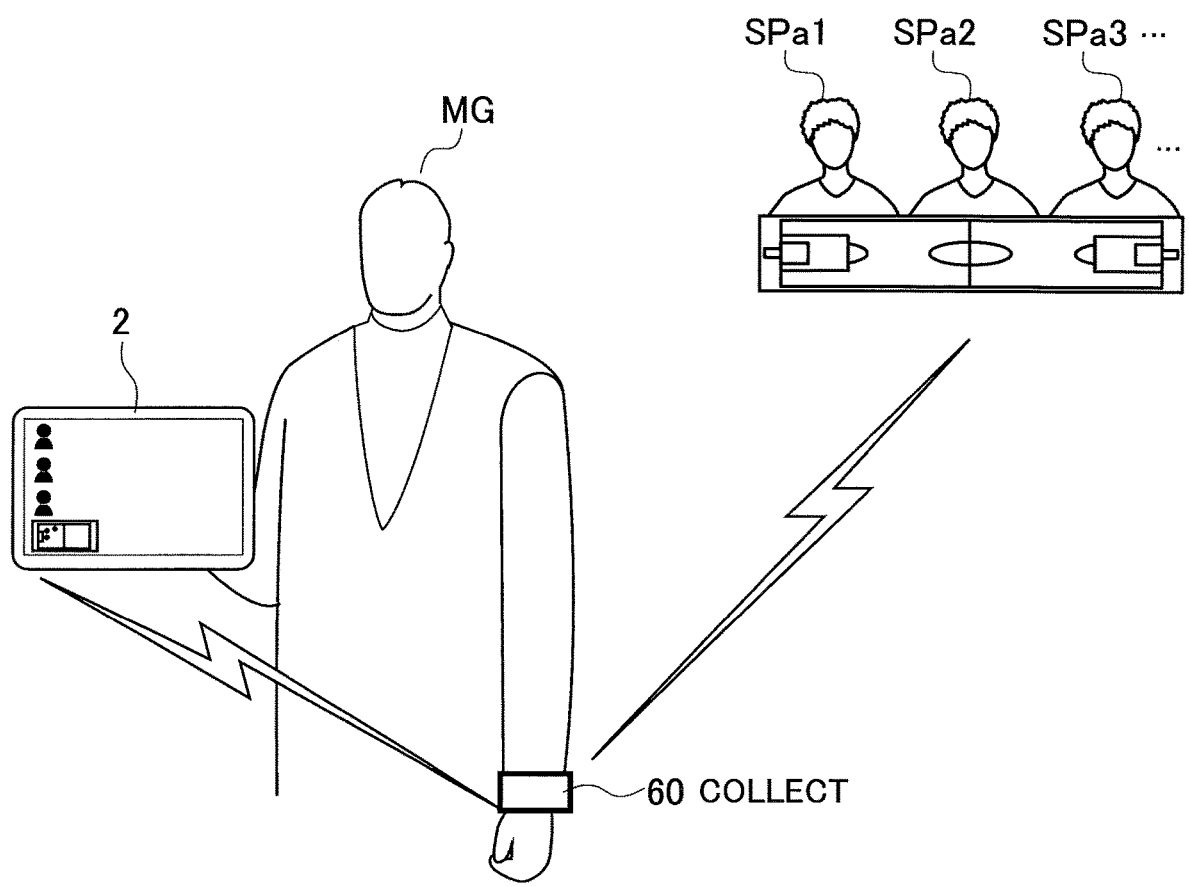
FIG. 44 is a diagram illustrating an attachment example of a collection apparatus applicable to the moving body information providing system.
Figure 45:
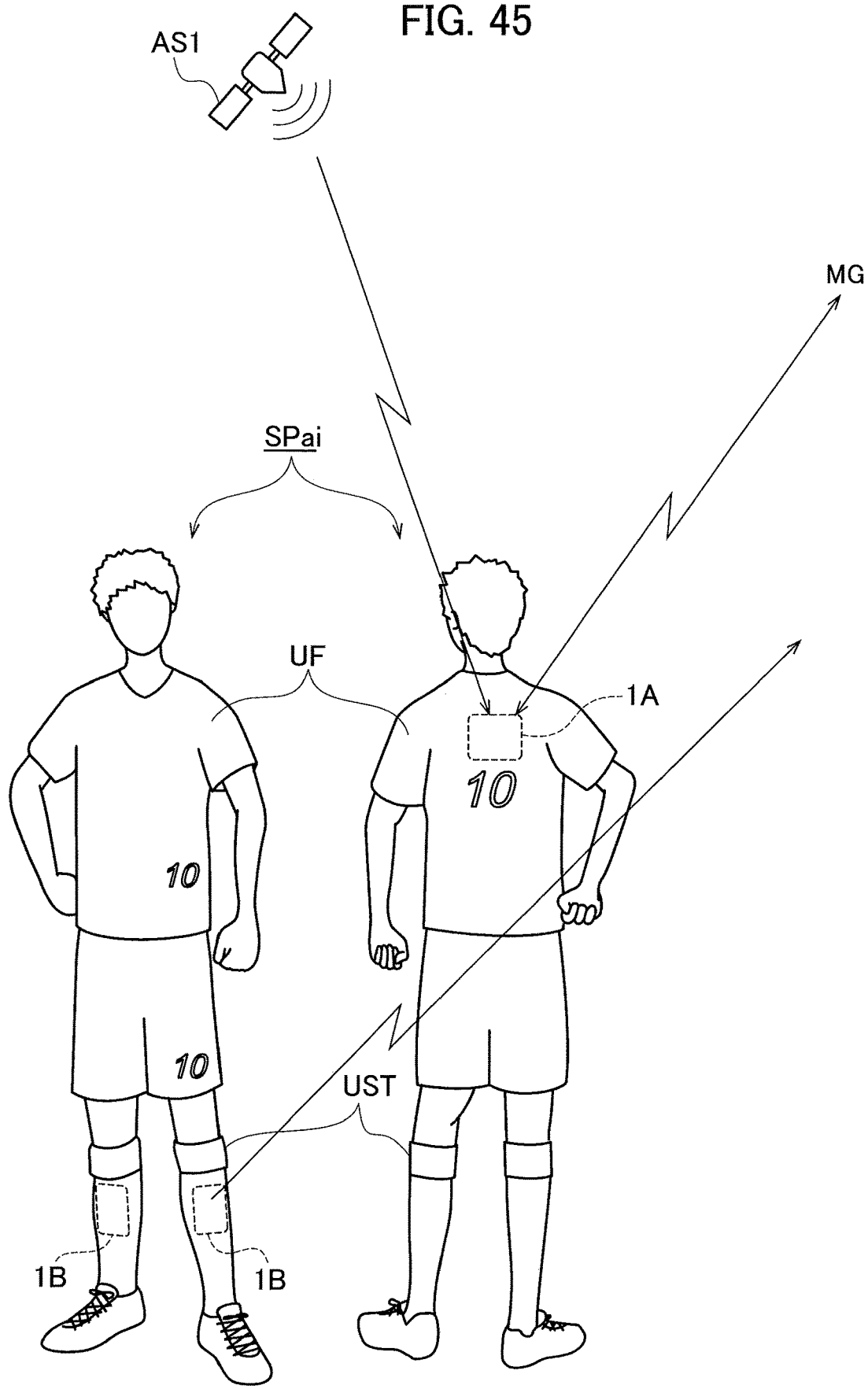
FIG. 45 is a schematic diagram illustrating another configuration example of the wearable device of the moving body information providing system.

The moving body information providing system may further include a collection apparatus 60 as illustrated in FIG. 44. The 60 may be provided near the soccer field Ai. In the example of FIG. 44, the 60 is worn on the wrist of the manager MG. Providing the 60 enables data collection from a larger number of wearable devices 1.

The collection apparatus 60 includes a collection function. The collection apparatus 60 collects the moving body information DSJi from plural wearable devices 1 at a time and transmits the collected information to the analysis result providing apparatus 3 or tablet 2.

In the description of above-described embodiments, the 9-axis sensor is provided for the wearable device 1. Instead, a back-wearable device 1A may be attached to a uniform UF of a soccer player SPai while a leg wearable device 1B is attached within a stocking UST (within a shin guard) of the uniform UF. The leg wearable device 1B is provided with the moving body state information detection sensor 18 (9-axis sensor) and the wireless module 11 and communicates with the tablet 2 of the manager MG. This allows for good understanding of movement of legs of the soccer player SPai, thus assisting coaching and analyses.

(Additional Explanation of Transmission Format KSRi)

During a soccer game or training, external persons (supporters, for example) sometimes intend to obtain information of soccer players SPai.

For safety communication in such a case, the aforementioned transmission format KSRi is preferably encrypted by the following method.

Generally, encryption increases the amount of data and sometimes reduces the transmission rate. The initial incorporation format creation unit 132g (see FIG. 38) therefore creates the transmission format KSRi in which the top part is for the position and system time and the following part is for sensor data, for example. The initial incorporation format creation unit 132g then waits for the sensor acquisition type ki from the tablet 2.

When receiving the sensor acquisition type ki, the initial incorporation format creation unit 132g creates the number of sensor data transmission regions corresponding to the sensor acquisition type ki in the latter part (the region for sensor data) of the transmission format KSRi according to the sensor acquisition type ki (the body temperature, 9-axis sensor data, heart rate, or a combination thereof, for example). The whole length of the transmission format KSRi varies on the sensor acquisition types ki from the tablet 2. The less the kinds of sensor data Di in the sensor acquisition type ki from the tablet 2, the smaller the amount of data to be transmitted.

It is assumed that the amount of data that can be transmitted at a time is 32 bytes. The data to be transmitted is designed to include only numerals as far as possible, and the number of bits used per character (per numeral) is set to 4 bits, for example. This virtually allows 64 bytes to be transmitted at a time. In addition, constituting transmission data with only numerals as far as possible makes it difficult to predict the contents.

The arrangement pattern of transmission data (a 64-byte numeral string, for example) may be configured to have a regularity. Specifically, data may be encrypted by rearranging the numerals at each transmission.

Instead of transmitting true time as the system time, the difference in time between the wearable device 1 and tablet 2 may be transmitted, for example.

The sensors of the sensor modules are not limited to the heart rate sensor and 9-axis sensor but may also include sensors for biometric information such as pulse rate and amount of sweating, and environment information such as illuminance, luminosity, humidity, wind speed, wind direction, and amount of rain. Alternatively, when the moving body is a non-living body, such as a drone, sensors for sensing vibration and the like are applicable. Use of (transfer of) commercially available sensors to constitute the sensors can reduce the price of the wearable device 1.

The moving body (living body) is not limited an athlete and may be a child or an elderly person. The moving body information providing system is applicable to watch over of children in a leisure land such as an amusement park or within a geo-fence such as a park or is applicable to care of caretakers or the like in a nursing home or hospital.

The moving body information providing system is not limited to a living body such as a player or an animal. The moving body information providing system is suitably used in monitoring of vibration, sound, height, water pressure, depth, weight, and the like of a non-living body, such as a heavy equipment including a farm machine and a construction machine or a drone, a robot, or the like which are put into a disaster site. Alternatively, the moving body information providing system is suitably used in sensing of water quality, gas concentration, and ad the like in locations that humans cannot enter.

Each of the above-described functions and processes can be implemented by one or more processing circuits. The processing circuit includes programmed processors, electric circuits, and the like and further includes a device such as an application specific integrated circuit (ASIC), circuitry elements arranged to execute the above-described functions, and the like.

The program of the present invention may be recorded in a non-transitory computer-readable medium (a recording medium in which information is recorded in an electrical or magnetic manner). The processor may be configured to execute instructions or a program stored in a non-transitory computer-readable medium to execute the procedures described in the embodiments.

As described above, the present invention is described with the embodiments. However, it should not be understood that the description and drawings constituting part of the disclosure limit the present invention. From the disclosure, those skilled in the art will know various substitutions, examples, and operation techniques.

It is obvious that the present invention includes various embodiments not described herein. The technical scope of the present invention is determined by only the features according to claims proper from the above description.

This application is based upon and claims the benefit of priority of the prior Japanese Patent Application No. 2016-193864, filed on Sep. 30, 2016, and the prior Japanese Patent Application No. 2017-156477, filed on Aug. 14, 2017, the entire contents of which are incorporated herein by reference

INDUSTRIAL APPLICABILITY

According to the present invention, the moving body information analysis apparatus displays finer interval positions than the positions detected by the GNSS module, on the screen, allowing the user watching the screen to understand in detail how the moving body is moving next. The fine position and position data are based on the correction data from the RTK reference station and are of high level of accuracy. Furthermore, the level of accuracy can be always maintained. When the moving body is a living body, the moving body information analysis apparatus displays biometric information in association with the fine interval positions. This allows the user watching the screen to understand the living body of the moving body at the fine interval position at a glance. When the moving body information from the moving body information detection terminal includes biometric information and moving body state information, such as posture and acceleration, the moving body information analysis apparatus displays the biometric information and moving body state information in association with each other on the screen. When the moving body is a soccer player, for example, the user (the manager or coach) of the moving body information analysis apparatus can understand the location and movement of the soccer player, and the situation at that moment at each detection position. Furthermore, if there are plural moving body information detection terminals, the analysis result providing apparatus can display the biometric information and moving body information of the moving body from a desired moving body information detection terminal in association with each other on the screen of the portable terminal. Accordingly, the analysis result providing apparatus is able to provide the situation (current situation), such as biometric information and moving body state information, of a lot of moving bodies in real time.

DESCRIPTION OF REFERENCE NUMERALS 1 wearable device
2 tablet
3 analysis result providing apparatus
13 main control module
15 position sensor
16 biometric information detection sensor
18 moving body state information detection sensor
22 collection and analysis application unit
30 moving body information analysis apparatus
31 application service unit
50 rtk reference station
132 controller
132i internal timer
132j initial time setting unit
132k association unit
132s position data calculation unit
132t position correction unit
225 moving body information transmission and reception unit
226 analysis result display processing unit
324 moving body position-related information creation server
324d position calculation unit
325 moving body information analysis server
330 position calculation data storage unit
spi player
spai (spa1, spa2, . . . ) soccer player
mg manager

The invention claimed is:

1. A moving body information providing system, comprising:
   a moving body information detection terminal that is attached to a moving body and detects the situation of the moving body; and
   a moving body information analysis controller, the moving body information analysis controller and the moving body information detection terminal performing wireless communication, wherein
   the moving body information detection terminal comprises:
   a time setting processor that performs initial time setting based on time of the moving body information analysis controller and creates as moving body information, raw data of global navigation satellite system (GNSS) data as the base of position detection and synchronized system time or position data that is obtained based on system data and the raw data;
   a transmitting circuit that transmits the moving body information to the moving body information analysis controller, and
   the moving body information analysis controller comprises:
   a position calculation data storage unit and further comprises:
   a processor (A) that, each time receiving the moving body information, reads the system time and position data included in the received moving body information as current fine position data information;
   a processor (B) that calculates a current fine position at the system time of the current fine position data information based on the system time and fine position of previous fine position data information stored in the position calculation data storage unit;
   a processor (C) that displays the calculated current fine position in association with the moving body on the screen; and
   a processor (D) that sets the calculated current fine position as a previous position and stores a pair of the previous fine position and the system time included in the current fine position data information, as the previous position data information in the position calculation data storage unit.

2. The moving body information providing system according to claim 1, wherein
   the moving body information analysis controller comprises a real-time kinematic (RTK) reference station, and
   the processor (A) comprises a correcting processor that, each time receiving the moving body information, corrects the position data based on correction data included in the received moving body information as the current fine position data information.

3. The moving body information providing system according to claim 1, wherein
   the moving body comprises a plurality of moving bodies, to each of them the moving body information detection terminal is attached, and
   each time receiving the moving body information, the processor (A) of the moving body information analysis controller stores the received moving body information in the position calculation data storage unit on a basis of identification information of the moving body information and sequentially reads the moving body information as the current fine position data information to execute the processors (B) to (D),
   wherein the identification information includes a moving body identifier and a moving body information detection terminal identifier.

4. The moving body information providing system according to claim 1, wherein
   the moving body information detection terminal calculates the position data each time acquiring a pulse-per-second (1 PPS) signal based on the GNSS signal.

5. The moving body information providing system according to claim 1, wherein
   the moving body information analysis controller comprises an area diagram storage unit storing an area diagram where the moving body moves, with coordinates of the area diagram, and the processor (B) further comprises a converting processor that, each time acquiring the current fine position, converts the current fine position to the coordinates of the area diagram, and the processor (C) comprises:

a display that displays the area diagram on the screen; and a fine position display that, each time that the obtained current fine position is converted to the coordinates of the area diagram, displays the current fine position on the area diagram.

6. The moving body information providing system according to claim 1, wherein the moving body information detection terminal comprises:

a position sensor module that receives the GNSS data, extracts the raw data, and outputs the raw data or a pulse-per-second (1 PPS) signal;

a moving body state detection module that detects movement information of the moving body at regular intervals;

an internal timer that outputs the system time;

a synchronizing processor that performs initial synchronization of the raw data and the system time;

a calculating processor that calculates the position data in synchronization with the 1 PPS signal or the raw data after the initial synchronization; and a generating processor that based on the system time or 1 PPS signal, creates a pair of a movement state of the moving body detected by the moving body state detection module at that moment and the position data as the moving body information.

7. The moving body information providing system according to claim 1, wherein the processor (C) comprises a display that displays information representing the movement state of the moving body on the screen in association with the current fine position.

8. The moving body information providing system according to claim 6, wherein the moving body state detection module comprises a biometric information detection sensor that detects biometric information of the moving body, the moving body information detection terminal comprises an information adding processor that adds to the system time, information of the movement state of the moving body detected by the moving body state detection module at that moment, the position data, and the biometric information to create the moving body information, and in the moving body information analysis controller, the processor (D) comprises a fine position adding processor that adds the biometric information to the current fine position and adds the system time included in the current moving body information to store the same as the previous moving body information in the position calculation data storage unit.

9. The moving body information providing system according to claim 1, wherein in the moving body information analysis controller, the processor (C) comprises a display that displays the information of the movement state of the moving body in association with the current fine position on the screen.

10. The moving body information providing system according to claim 1, wherein the moving body information analysis controller comprises:

a reading processor that upon reception of the moving body information, reads past biometric information a certain period before the received moving body information, from the position calculation data storage unit;

an analyzing processor that performs analysis processing based on the read biometric information and the biometric information included in the received moving body information; and a display that displays information of the result of the analysis processing in association with the current fine position.

11. The moving body information providing system according to claim 5, wherein the area diagram storage unit stores a camera image of a predetermined area taken by a camera, and the processor (C) calculates a fine position on the camera image based on the current fine position, the movement information of the moving body, the coordinates of the area, and a camera parameter of the camera for display.

12. The moving body information providing system according to claim 1, wherein the moving body information analysis controller comprises a display and an analysis result providing controller of an analysis center, the display and the analysis result providing controller communicate with each other through the Internet network while the display performs the wireless communication, the display comprises:

a moving body information processor that receives the moving body information through the wireless communication and each time receiving the moving body information, transmits the moving body information to the analysis result providing controller through the Internet network, and a control data processor that receives control data from the analysis result providing controller through the Internet network and based on the control data, displays the current fine position in association with the moving body on the screen, and the analysis result providing controller comprises:

the position calculation data storage unit and further comprises:

the processor (A) that each time receiving the moving body information from the display, reads system time included in the received moving body information and the position data as current fine position data information;

the processor (B) that calculates a current fine position at the system time of the current fine position data information based on the system time and system time and fine position of previous fine position data information stored in the position calculation data storage unit;

the processor (C) that transmits to the display, control data to display the calculated current fine position in association with the moving body on the screen; and the processor (D) that sets the calculated current fine position as a previous position and stores a pair of the previous fine position and the system time included in the current fine position data information, as the previous position data information in the position calculation data storage unit.

13. The moving body information providing system according to claim 12, wherein the display comprises:

a request transmitting circuit that sequentially transmits to the moving body information detection terminal, moving body information request information requesting the moving body information from the moving body information detection terminal in an inputted time range when the moving body information is to be acquired, and a moving body information transmitting circuit that transmits the moving body information to the analysis result providing controller each time receiving the moving body information in response to the moving body information request information from the display.

14. The moving body information providing system according to claim 12, wherein the analysis result providing controller further comprises:

an analyzing processor that upon receiving the moving body information, performs analysis processing based on past moving body information and the received moving body information, and an information transmitting circuit that transmits in the control data, information to display the analysis result on the screen of the display.

15. The moving body information providing system according to claim 12, wherein the analysis result providing controller comprises:

an area diagram storage unit storing an area diagram where the moving body moves, with coordinates of the area diagram, and a diagraming processor that reads the area diagram from the area diagram storage unit and displays the area diagram in the control data on the screen of the display.

16. The moving body information providing system according to claim 15, wherein the area diagram storage unit stores a camera image of a predetermined area where the moving body moves, captured by a camera, and the analysis result providing controller comprises:

a camera imaging processor that reads the camera image and transmits to the display, control data to display the read camera image on the screen;

a calculating processor that calculates a fine position on the camera image based on the fine position, information representing a movement state of the moving body, coordinates of the area diagram, and a camera parameter of the camera; and a data transmitting circuit that transmits the calculated fine position and control data to display the fine position on the camera image.

17. The moving body information providing system according to claim 12, wherein any one of the display and the analysis result providing controller comprises:

a correction receiving processor that receives correction data that is a difference between the GNSS data from a reference position providing station and reference position; and a correcting processor that corrects the position data or system time included in the current moving body information, based on the correction data.

18. A moving body information providing program that is a moving body information providing system comprising:

a moving body information detection terminal that is attached to a moving body and detects the situation of the moving body; and a moving body information analysis controller, the moving body information analysis controller and moving body information detection terminal performing wireless communication, the program causing a computer to execute the functions as:

a time setting processor that performs initial time setting based on time of the moving body information analysis controller and creates as moving body information, raw data of global navigation satellite system (GNSS) data as the base of position detection and synchronized system time or position data that is obtained based on system data and the raw data;

a processor (A) that each time receiving the moving body information from the moving body information detection terminal, reads system time and position data included in the received moving body information as current fine position data information;

a processor (B) that calculates a current fine position at the system time of the current fine position data information based on the system time and the system time and fine position of previous fine position data information stored in a position calculation data storage unit;

a processor (C) that displays the calculated current fine position in association with the moving body on the screen; and a processor (D) that sets the calculated current fine position as a previous fine position and stores a pair of the previous fine position and the system time included in the current fine position data information, as the previous fine position data information in the position calculation data storage unit.

19. The moving body information providing program according to claim 18, further causing the computer to execute the function as a correcting processor that each time receiving the moving body information, corrects position data included in the received moving body information based on correction data from a real-time kinematic (RTK) reference station as the current fine position data info nation.

* * * * *